(12) United States Patent
Deiman et al.

(10) Patent No.: US 7,794,986 B2
(45) Date of Patent: Sep. 14, 2010

(54) METHOD FOR AMPLIFICATION OF RNA SEQUENCES

(75) Inventors: Birgit Alberta Louisa Maria Deiman, Oisterwijk (NL); Arnoldina Margaretha Wilhelmina Strijp, 's Hertogenbosch (NL)

(73) Assignee: Biomerieux B.V., Boxtel (NL)

( * ) Notice: Subject to any disclaimer, the term of this patent is extended or adjusted under 35 U.S.C. 154(b) by 460 days.

(21) Appl. No.: 10/578,552

(22) PCT Filed: Oct. 27, 2004

(86) PCT No.: PCT/EP2004/012190

§ 371 (c)(1),
(2), (4) Date: May 8, 2007

(87) PCT Pub. No.: WO2005/047535

PCT Pub. Date: May 26, 2005

(65) Prior Publication Data

US 2008/0176294 A1 Jul. 24, 2008

(30) Foreign Application Priority Data

Nov. 14, 2003 (EP) ................... 03078568

(51) Int. Cl.
*C12P 19/34* (2006.01)
*C07H 21/04* (2006.01)
(52) U.S. Cl. ................. 435/91.21; 536/24.33
(58) Field of Classification Search ............. 435/92.1, 435/91.21; 536/24.33
See application file for complete search history.

(56) References Cited

U.S. PATENT DOCUMENTS 5,891,681 A 4/1999 Mallet et al.
6,117,631 A 9/2000 Nilsen et al.

FOREIGN PATENT DOCUMENTS

WO WO 97/10364 A1 3/1997

OTHER PUBLICATIONS

International Search Report for PCT/EP2004/012190, mailed Dec. 4, 2005.
Fahy et al. "Self-sustained Sequence Replication (3SR): An Isothermal Transcription based Amplification System Alternative to PCR" *PCR Methods and Applications* 1(1):25-33 (1991).
Gambari et al. "Peptide-Nucleic Acids (PNAs): A Tool for the Development of Gene Expression Modifiers" *Current Pharmaceutical Design* 7:1839-1862 (2001).
Kievits et al. "NASBA™ isothermal enzymatic in vitro nucleic acid amplification optimized for the diagnosis of HIV-1 infection" *Journal of Virological Methods* 35:273-286 (1991).
Liu et al. "Transcription Activation by a PNA-Peptide Chimera in a Mammalian Cell Extract" *Chemistry & Biology* 10:909-916 (2003).

*Primary Examiner*—Gary Benzion
*Assistant Examiner*—Cynthia B Wilder
(74) *Attorney, Agent, or Firm*—Myers Bigel Sibley & Sajovec, P.A.

(57) ABSTRACT

The invention relates to a method for amplification of a target RNA sequence, wherein the first primer comprises a hybridizing sequence of 7 to 14 nucleotides, which is capable of binding to a first segment of the target RNA sequence, a transcription enhancing sequence, and an anchor which is capable of binding to a second segment of the target RNA sequence, and/or wherein the second primer comprises a hybridizing sequence of 7 to 14 nucleotides, an amplification enhancing sequence and an anchor which is capable of binding to a second segment of the first single stranded cDNA. The invention further relates to primers for the amplification of target RNA sequences and to a kit comprising one or more of the primers.

28 Claims, 53 Drawing Sheets

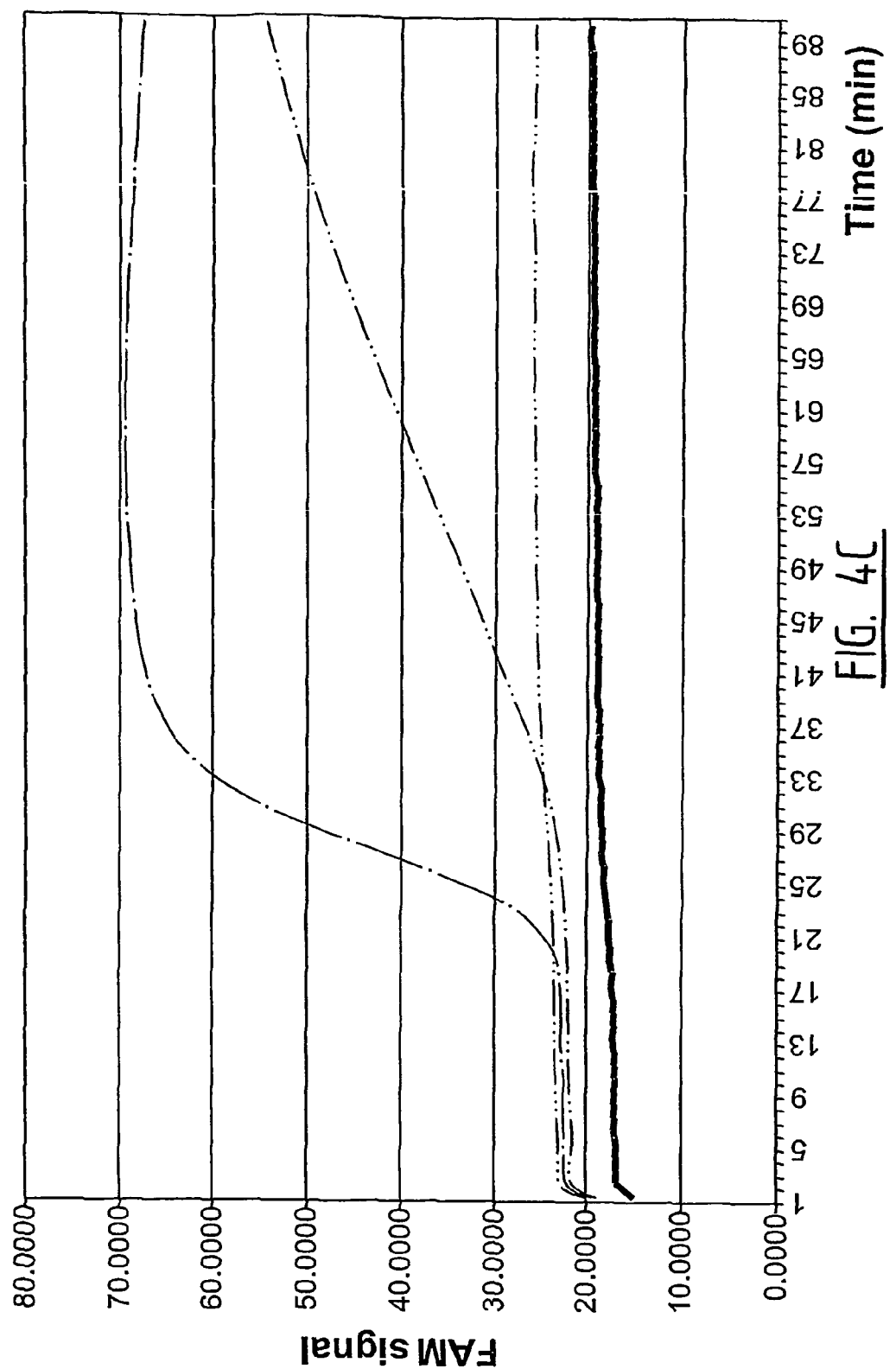

SEQUENCE LISTING

<160> NUMBER OF SEQ ID NOS: 40

<210> SEQ ID NO 1
<211> LENGTH: 54
<212> TYPE: DNA
<213> ORGANISM: Artificial
<220> FEATURE:
<223> OTHER INFORMATION: Synthetic oligonucleotide primer

<400> SEQUENCE: 1
aattctaata cgactcacta tagggtgcta tgtcacttcc ccttggttct ctca                54

<210> SEQ ID NO 2
<211> LENGTH: 29
<212> TYPE: DNA
<213> ORGANISM: Artificial
<220> FEATURE:
<223> OTHER INFORMATION: Synthetic oligonucleotide primer

<400> SEQUENCE: 2
agtgggggga catcaagcag ccatgcaaa                                            29

<210> SEQ ID NO 3
<211> LENGTH: 21
<212> TYPE: DNA
<213> ORGANISM: Artificial
<220> FEATURE:
<223> OTHER INFORMATION: Synthetic oligonucleotide primer

<400> SEQUENCE: 3
agtgggggga catcaagcag c                                                    21

<210> SEQ ID NO 4
<211> LENGTH: 46
<212> TYPE: DNA
<213> ORGANISM: Artificial
<220> FEATURE:
<223> OTHER INFORMATION: Synthetic oligonucleotide primer

<400> SEQUENCE: 4
aattctaata cgactcacta tagggaaacg ggcacgagct ctctca                         46

<210> SEQ ID NO 5
<211> LENGTH: 68
<212> TYPE: DNA
<213> ORGANISM: Artificial
<220> FEATURE:
<223> OTHER INFORMATION: Synthetic oligonucleotide primer

<400> SEQUENCE: 5
tgctatgtca cttccccttg gtaattctaa tacgactcac tatagggaaa cgggcacgag          60
ctctctca                                                                   68

<210> SEQ ID NO 6
<211> LENGTH: 66
<212> TYPE: DNA
<213> ORGANISM: Artificial
<220> FEATURE:
<223> OTHER INFORMATION: Synthetic oligonucleotide primer

<400> SEQUENCE: 6
ctatgtcact tccccttggt aattctaata cgactcacta tagggaaacg ggcacgagct          60
ctctca                                                                     66

<210> SEQ ID NO 7
<211> LENGTH: 63
<212> TYPE: DNA
<213> ORGANISM: Artificial
<220> FEATURE:
<223> OTHER INFORMATION: Synthetic oliogonucleotide primer

<400> SEQUENCE: 7
tgtcacttcc ccttggtaat tctaatacga ctcactatag ggaaacgggc acgagctctc    60
tca                                                                 63

<210> SEQ ID NO 8
<211> LENGTH: 60
<212> TYPE: DNA
<213> ORGANISM: Artificial
<220> FEATURE:
<223> OTHER INFORMATION: Synthetic oligonucleotide primer

<400> SEQUENCE: 8
cacttcccct tggtaattct aatacgactc actataggga acgggcacg agctctctca    60

<210> SEQ ID NO 9
<211> LENGTH: 58
<212> TYPE: DNA
<213> ORGANISM: Artificial
<220> FEATURE:
<223> OTHER INFORMATION: Synthetic oligonucleotide primer

<400> SEQUENCE: 9 cttcccttg gtaattctaa tacgactcac tagggaaa cgggcacgag ctctctca         58

<210> SEQ ID NO 10
<211> LENGTH: 55
<212> TYPE: DNA
<213> ORGANISM: Artificial
<220> FEATURE:
<223> OTHER INFORMATION: Synthetic oligonucleotide primer

<400> SEQUENCE: 10
ccccttggta attctaatac gactcactat agggaaacgg gcacgagctc tctca         55

<210> SEQ ID NO 11
<211> LENGTH: 53
<212> TYPE: DNA
<213> ORGANISM: Artificial
<220> FEATURE:
<223> OTHER INFORMATION: Synthetic oligonucleotide primer

<400> SEQUENCE: 11
ccttggtaat tctaatacga ctcactatag ggaaacgggc acgagctctc tca           53

<210> SEQ ID NO 12
<211> LENGTH: 60
<212> TYPE: DNA
<213> ORGANISM: Artificial
<220> FEATURE:
<223> OTHER INFORMATION: Synthetic oligoncleotide primer
<220> FEATURE:
<221> NAME/KEY: misc_feature
<222> LOCATION: (6)..(9)
<223> OTHER INFORMATION: 2'-O-Methyl nucleotides
<220> FEATURE:
<221> NAME/KEY: misc_feature
<222> LOCATION: (11)..(14)
<223> OTHER INFORMATION: 2'-O-Methyl nucleotides

```
<400> SEQUENCE: 12
cacttcccct tggtaattct aatacgactc actataggga aacgggcacg agctctctca      60

<210> SEQ ID NO 13
<211> LENGTH: 58
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (4)..(7)
<223> OTHER INFORMATION: 2'-O-Methyl nucleotides
<220> FEATURE:
<221> NAME/KEY: misc_feature
<222> LOCATION: (9)..(12)
<223> OTHER INFORMATION: 2'-O-Methyl nucleotides

<400> SEQUENCE: 13
cttccccttg gtaattctaa tacgactcac tagggaaa cgggcacgag ctctctca      58

<210> SEQ ID NO 14
<211> LENGTH: 58
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(1)
<223> OTHER INFORMATION: 2'-O-Methyl oligonucleotide
<220> FEATURE:
<221> NAME/KEY: misc_feature
<222> LOCATION: (4)..(7)
<223> OTHER INFORMATION: 2'-O-Methyl oligonucleotides
<220> FEATURE:
<221> NAME/KEY: misc_feature
<222> LOCATION: (10)..(11)
<223> OTHER INFORMATION: 2'-O-Methyl oligonucleotides

<400> SEQUENCE: 14
cttccccttg gtaattctaa tacgactcac tagggaaa cgggcacgag ctctctca      58

<210> SEQ ID NO 15
<211> LENGTH: 55
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(4)
<223> OTHER INFORMATION: 2'-O-Methyl nucleotides
<220> FEATURE:
<221> NAME/KEY: misc_feature
<222> LOCATION: (6)..(6)
<223> OTHER INFORMATION: 2'-O-Methyl nucleotides

<400> SEQUENCE: 15
ccccttggta attctaatac gactcactat agggaaacgg gcacgagctc tctca      55

<210> SEQ ID NO 16
<211> LENGTH: 55
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(4)
<223> OTHER INFORMATION: 2'-O-methyl nucleotides
```

<220> FEATURE:
<221> NAME/KEY: misc_feature
<222> LOCATION: (7)..(8)
<223> OTHER INFORMATION: 2'-O-methyl nucleotides

<400> SEQUENCE: 16
ccccttggta attctaatac gactcactat agggaaacgg gcacgagctc tctca        55

<210> SEQ ID NO 17
<211> LENGTH: 53
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(7)
<223> OTHER INFORMATION: 2'-O-Methyl nucleotides

<400> SEQUENCE: 17
ccttggtaat tctaatacga ctcactatag ggaaacgggc acgagctctc tca          53

<210> SEQ ID NO 18
<211> LENGTH: 53
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(2)
<223> OTHER INFORMATION: 2'-O-Methyl nucleotides
<220> FEATURE:
<221> NAME/KEY: misc_feature
<222> LOCATION: (4)..(7)
<223> OTHER INFORMATION: 2'-O-Methyl nucleotides

<400> SEQUENCE: 18
ccttggtaat tctaatacga ctcactatag ggaaacgggc acgagctctc tca          53

<210> SEQ ID NO 19
<211> LENGTH: 53
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(4)
<223> OTHER INFORMATION: LNA nucleotides
<220> FEATURE:
<221> NAME/KEY: misc_feature
<222> LOCATION: (7)..(7)
<223> OTHER INFORMATION: LNA nucleotide

<400> SEQUENCE: 19
ccttggtaat tctaatacga ctcactatag ggaaacgggc acgagctctc tca          53

<210> SEQ ID NO 20
<211> LENGTH: 53
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (3)..(7)
<223> OTHER INFORMATION: LNA nucleotides

<400> SEQUENCE: 20
ccttggtaat tctaatacga ctcactatag ggaaacgggc acgagctctc tca          53

<210> SEQ ID NO 21
<211> LENGTH: 53
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(2)
<223> OTHER INFORMATION: LNA nucleotides
<220> FEATURE:
<221> NAME/KEY: misc_feature
<222> LOCATION: (5)..(6)
<223> OTHER INFORMATION: LNA nucleotides

<400> SEQUENCE: 21
ccttggtaat tctaatacga ctcactatag ggaaacgggc acgagctctc tca          53

<210> SEQ ID NO 22
<211> LENGTH: 53
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(1)
<223> OTHER INFORMATION: LNA nucleotide
<220> FEATURE:
<221> NAME/KEY: misc_feature
<222> LOCATION: (3)..(3)
<223> OTHER INFORMATION: LNA nucleotide
<220> FEATURE:
<221> NAME/KEY: misc_feature
<222> LOCATION: (5)..(5)
<223> OTHER INFORMATION: LNA nucleotide
<220> FEATURE:
<221> NAME/KEY: misc_feature
<222> LOCATION: (7)..(7)
<223> OTHER INFORMATION: LNA nucleotide

<400> SEQUENCE: 22
ccttggtaat tctaatacga ctcactatag ggaaacgggc acgagctctc tca          53

<210> SEQ ID NO 23
<211> LENGTH: 60
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(14)
<223> OTHER INFORMATION: PNA anchor

<400> SEQUENCE: 23 cacttccct tggtaattct aatacgactc actataggga aacgggcacg agctctctca    60

<210> SEQ ID NO 24
<211> LENGTH: 58
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(12)
<223> OTHER INFORMATION: PNA anchor

<400> SEQUENCE: 24

```
cttccccttg gtaattctaa tacgactcac tatagggaaa cgggcacgag ctctctca        58

<210> SEQ ID NO 25
<211> LENGTH: 55
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(9)
<223> OTHER INFORMATION: PNA anchor

<400> SEQUENCE: 25
ccccttggta attctaatac gactcactat agggaaacgg gcacgagctc tctca           55

<210> SEQ ID NO 26
<211> LENGTH: 53
<212> TYPE: DNA
<213> ORGANISM: Artificial
<220> FEATURE:
<223> OTHER INFORMATION: Synthetic oligonucleotide primer
<220> FEATURE:
<221> NAME/KEY: misc_feature
<222> LOCATION: (1)..(7)
<223> OTHER INFORMATION: PNA anchor

<400> SEQUENCE: 26
ccttggtaat tctaatacga ctcactatag ggaaacgggc acgagctctc tca             53

<210> SEQ ID NO 27
<211> LENGTH: 46
<212> TYPE: DNA
<213> ORGANISM: Artificial
<220> FEATURE:
<223> OTHER INFORMATION: Synthetic oligonucleotide primer

<400> SEQUENCE: 27
agtgggggga catcaagcag ccgacttcag gacttcagga tgcaaa                     46

<210> SEQ ID NO 28
<211> LENGTH: 42
<212> TYPE: DNA
<213> ORGANISM: Artificial
<220> FEATURE:
<223> OTHER INFORMATION: Synthetic oligonucleotide primer

<400> SEQUENCE: 28
gggggacatc aagcagccga cttcaggact tcaggatgca aa                         42

<210> SEQ ID NO 29
<211> LENGTH: 40
<212> TYPE: DNA
<213> ORGANISM: Artificial
<220> FEATURE:
<223> OTHER INFORMATION: Synthetic oligonucleotide primer

<400> SEQUENCE: 29
gggacatcaa gcagccgact tcaggacttc aggatgcaaa                            40

<210> SEQ ID NO 30
<211> LENGTH: 38
<212> TYPE: DNA
<213> ORGANISM: Artificial
<220> FEATURE:
<223> OTHER INFORMATION: Synthetic oligonucleotide primer
```

```
<400> SEQUENCE: 30
gacatcaagc agccgacttc aggacttcag gatgcaaa                                    38

<210> SEQ ID NO 31
<211> LENGTH: 38
<212> TYPE: DNA
<213> ORGANISM: Artificial
<220> FEATURE:
<223> OTHER INFORMATION: Synthetic oligonucleotide primer

<400> SEQUENCE: 31
agtgggggga catcgacttc aggacttcag gaagcagc                                    38

<210> SEQ ID NO 32
<211> LENGTH: 38
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: 5' FAM label
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (27)..(27)
<223> OTHER INFORMATION: n is inosine
<220> FEATURE:
<221> NAME/KEY: misc_feature
<222> LOCATION: (38)..(38)
<223> OTHER INFORMATION: 3' dabcyl label

<400> SEQUENCE: 32
gcatgcatca atgaggangc tgcagantgg gagcatgc                                    38

<210> SEQ ID NO 33
<211> LENGTH: 46
<212> TYPE: DNA
<213> ORGANISM: Artificial
<220> FEATURE:
<223> OTHER INFORMATION: Synthetic oligonucleotide primer

<400> SEQUENCE: 33
aattctaata cgactcacta tagggcaagc accctatcag gcagta                           46

<210> SEQ ID NO 34
<211> LENGTH: 20
<212> TYPE: DNA
<213> ORGANISM: Artificial
<220> FEATURE:
<223> OTHER INFORMATION: Synthetic oligonucleotide primer

<400> SEQUENCE: 34
gtctagccat ggcgttagta                                                        20

<210> SEQ ID NO 35
<211> LENGTH: 60
<212> TYPE: DNA
<213> ORGANISM: Artificial
<220> FEATURE:
<223> OTHER INFORMATION: Synthetic oligonucleotide primer

<400> SEQUENCE: 35
caagcaccct atcaaattct aatacgactc actataggga agagggcacg agcggcagta            60
```

```
<210> SEQ ID NO 36
<211> LENGTH: 60
<212> TYPE: DNA
<213> ORGANISM: Artificial
<220> FEATURE:
<223> OTHER INFORMATION: Synthetic oligonucleotide primer

<400> SEQUENCE: 36
tcgcaagcac cctaaattct aatacgactc actataggga agagggcacg agcggcagta        60

<210> SEQ ID NO 37
<211> LENGTH: 60
<212> TYPE: DNA
<213> ORGANISM: Artificial
<220> FEATURE:
<223> OTHER INFORMATION: Synthetic oligonucleotide primer

<400> SEQUENCE: 37
caagcaccct atcaaattct aatacgactc actataggga agagggcacg agcggcagta        60

<210> SEQ ID NO 38
<211> LENGTH: 34
<212> TYPE: DNA
<213> ORGANISM: Artificial
<220> FEATURE:
<223> OTHER INFORMATION: Synthetic oligonucleotide probe
<220> FEATURE:
<221> NAME/KEY: misc_feature
<222> LOCATION: (1)..(1)
<223> OTHER INFORMATION: 5" FAM label
<220> FEATURE:
<221> NAME/KEY: misc_feature
<222> LOCATION: (25)..(25)
<223> OTHER INFORMATION: n is inosine
<220> FEATURE:
<221> NAME/KEY: misc_feature
<222> LOCATION: (34)..(34)
<223> OTHER INFORMATION: 3' dabcyl label

<400> SEQUENCE: 38
gctagcattt gggcgtgccc ccgcnagagc tagc                                    34

<210> SEQ ID NO 39
<211> LENGTH: 14
<212> TYPE: DNA
<213> ORGANISM: Artificial
<220> FEATURE:
<223> OTHER INFORMATION: Synthetic primer transcription enhancing
      sequence

<400> SEQUENCE: 39
aaacgggcac gagc                                                          14

<210> SEQ ID NO 40
<211> LENGTH: 17
<212> TYPE: DNA
<213> ORGANISM: Artificial
<220> FEATURE:
<223> OTHER INFORMATION: Synthetic primer amplification enhancing
      sequence

<400> SEQUENCE: 40
gacttcagga cttcagg                                                       17
```

METHOD FOR AMPLIFICATION OF RNA SEQUENCES

Figure 1:
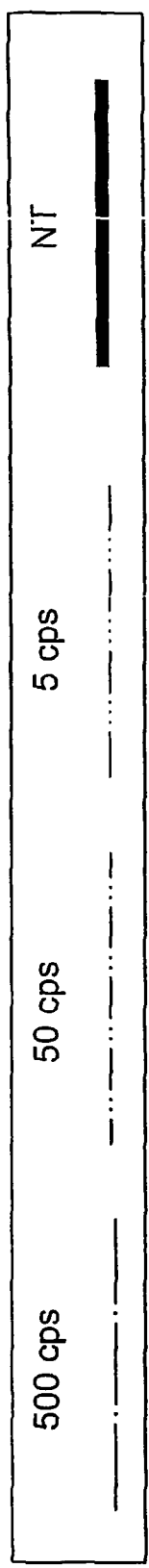

The present invention relates to a method for amplification of target RNA sequences, to primers for the amplification of target RNA sequences and to a kit comprising one or more of the primers.

Nucleic acid amplification methods, wherein target RNA or DNA sequences are amplified, are generally applied in the field of molecular biology, biochemistry and biotechnology and the possible applications are numerous and still increasing. The amplification methods increase the number of copies of a particular target nucleic acid sequence, which often is present in small amounts and in an environment in which a wide variety of other nucleic acids, both RNA and DNA, are present.

Nucleic acid amplification methods are in particular used to facilitate the detection and quantification of specific target nucleic acid sequences present in samples such as blood, sperm, tissue, hair, microorganisms, cells, tumors etc., in diagnosing, for example, infectious diseases, inherited diseases, and various types of cancer. In addition, nucleic acid amplification methods have found their applications in other fields where samples are investigated in which informative target nucleic acids may be present in minute amounts, such as in forensic sciences and in archeology or to establish paternity.

Several nucleic acid amplification techniques are known, like Polymerase Chain Reaction (PCR) and Transcription Based Amplification (TBA), which are based on different mechanisms of action, but all depend on the annealing of one or more primers to the boundaries of the target nucleic acid sequence or its complementary sequence. The annealing of a primer to the boundary of the target nucleic acid sequence is provided by the hybridization of a contiguous number of nucleotides comprised in the primer, to a contiguous number of complementary nucleotides in the target nucleic acid sequence.

Efficient hybridization of the primer generally requires at least 15 continuous complimentary nucleotides. If less nucleotides are present, the ratio between specific and non-specific annealing of the primer decreases below a point where no longer effective amplification of the target nucleic acid can occur. The requirement of at least 15 contiguous complementary nucleotides, however, limits the possibility of for example amplification of target nucleic acids in case only a consensus sequence of the target sequence can be used, especially in cases when all genotypes from target nucleic acids derived from organisms like viruses, bacteria, and yeast, or from tissue specimens like blood, cells, tumors, and lymphoid fluids are to be amplified. When, due to genetic variation, the consensus sequence may vary among individual species, inefficient hybridization of the primers as a consequence of the presence of non-complementary nucleotides may occur.

If several "genetic variations" of a target nucleotide sequence are known, conserved stretches of nucleotides can be identified and used for primer design. However, preferred conserved stretches in some species, like RNA viruses, such as parts of the coding region of the human hepatitis C virus, are sometimes too small to be used to design efficient primers. In addition, even these conserved segments have a tendency to mutate, which is most pronounced in fast dividing organisms like viruses and bacteria, resulting in a reduced efficiency of hybridization of the primer. As a consequence, amplification may not occur, which is highly undesirable in for example routine diagnostics since a false negative amplification result can have severe consequences for the patient concerned.

Therefore there is a clear need for an amplification method which allows for amplification using small stretches of target RNA sequences and which method is less prone n mutations or genetic variations in the hybridizing segment of the target sequence.

In the research that led to the present invention it has been found that the above-mentioned problems can be obviated by an amplification method comprising the steps of:
(a) annealing a first primer to the target RNA sequence, said first primer comprising a hybridizing sequence, which is complementary to and hybridizes to at least a first segment of the target RNA sequence, operatively associated with a promoter sequence;
(b) extending said first primer in a reaction catalyzed by a DNA polymerase, forming a first RNA/cDNA hybrid nucleic acid molecule;
(c) selectively removing the target RNA sequence of the first RNA/cDNA hybrid nucleic acid molecule forming a first single stranded cDNA sequence;
(d) annealing a second primer to the obtained first single stranded cDNA sequence, said second primer comprising a hybridizing sequence which is complementary to and hybridizes to a first segment of the first single stranded cDNA sequence;
(e) extending said second primer in a reaction catalyzed by a DNA polymerase to form a first double stranded DNA molecule; and
(f) employing the first double stranded DNA molecule of step (e) in the preparation of a plurality of RNA transcripts that are complementary to the target RNA sequence in a reaction catalyzed by a DNA-dependent RNA polymerase with specificity for the promoter sequence comprised in the first primer;

wherein the first primer comprises a hybridizing sequence of 7 to 14 nucleotides, a transcription enhancing sequence, and an anchor which is capable of binding to a second segment of the target RNA sequence, and/or wherein the second primer comprises a hybridizing sequence of 7 to 14 nucleotides, an amplification enhancing sequence and an anchor which is capable of binding to a second segment of the first single stranded cDNA.

According to the present invention it has surprisingly been found that a reduction of the number of contiguous hybridizing nucleotides in at least one of the primers still allows for a reliable amplification method if said primer additionally comprises an anchor which binds to a second segment of the target RNA sequence, which is not the hybridizing nucleotide sequence, in such a way that the anchor exposes the hybridising sequence to the first segment.

The use of an anchor in addition to a hybridizing sequence thus results in a two-step annealing process: 1) binding of the anchor to a segment of the target RNA sequence, designated as the second segment, and 2) hybridization of the hybridizing sequence of the primer to the contiguous complementary nucleotides of the target RNA sequence, designated as the first segment, which steps can occur simultaneously or sequentially (i.e. first step 1 and then step 2 or first step 2 and then step 1). The anchor may bind specifically, but the anchor and hybridizing sequence may also together be responsible for the specific interaction of the primer to the target RNA, for example in case the anchor is 7-14 nucleotides in length and the hybridizing sequence is 13-7 nucleotides in length, by which the anchor and hybridizing sequence independently do not bind specifically, but the combination is specific.

According to the invention, the number of nucleotides in the hybridizing sequence of the primers can be reduced to 14, 13, 12, 11, 10, 9, 8, or 7 nucleotides. Due to the presence of the anchor in the primer, specific binding of the primer to the target nucleotide sequence will occur, regardless of the fact that the hybridizing part only contains maximally 14 nucleotides, and in itself would not be able to hybridize specifically. Thus, by the combination of the anchor and the hybridizing sequence specific binding of the primer to the target sequence is accomplished.

Figure 16A:
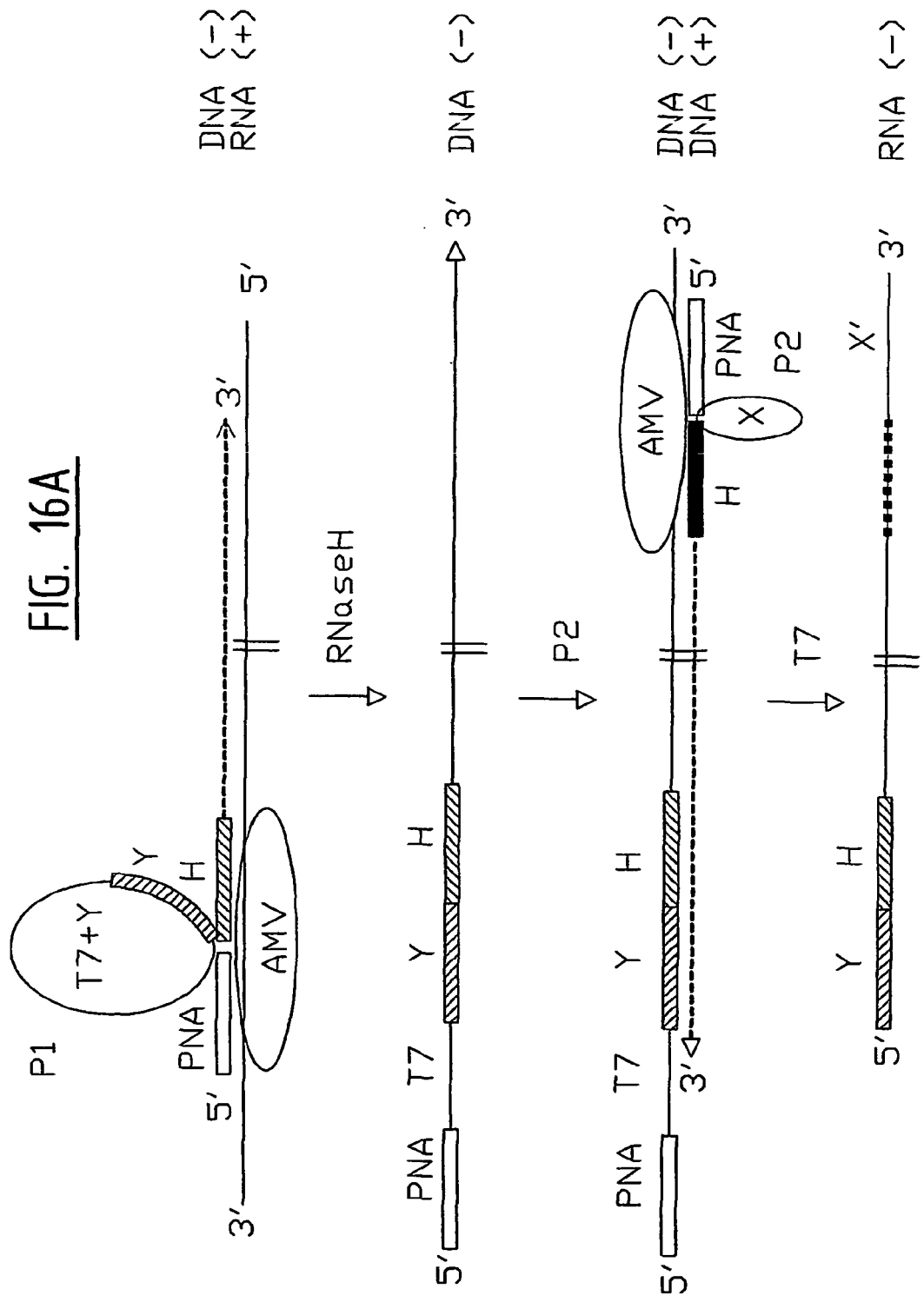

The method according to the invention is further explained referring to FIG. 16, wherein a preferred embodiment of the method is shown. During the first step the PNA anchor present in the first primer (P1), usually designated as the forward primer, binds to a segment of the target RNA sequence (RNA+). Subsequently, the hybridizing sequence (H) of the first primer hybridizes to the first segment of the target RNA sequence.

After annealing of the first primer to the target RNA sequence, the primer is extended using a DNA polymerase, such as the avian myeloblastosis virus (AMV) reverse transcriptase polymerase. The DNA polymerase will copy the target RNA sequence forming a first RNA/cDNA hybrid molecule.

Simultaneously, or subsequently the target RNA sequence is selectively removed, preferably by enzymatic digestion with for example an RNase. The resulting first single stranded cDNA sequence (DNA-) is used as a template for the subsequent step in the amplification process.

This subsequent step requires the annealing of a second primer (P2), usually designated the reverse primer, to the formed first single stranded cDNA. According to the shown embodiment, the second primer also comprises a hybridizing sequence (H) which is complementary to and hybridizes to a first segment of the single stranded cDNA, an amplification enhancing sequence (X) and a PNA anchor which is capable of specific binding to a second segment of the first single stranded cDNA sequence.

According to the present invention, both the first and second primer, or only the first or second primer, may comprise a short hybridizing sequence and an anchor.

In a subsequent step of the amplification method, the second primer is extended by the AMV reverse transcriptase polymerase using the first single stranded CDNA sequence as a template resulting in a first double stranded DNA molecule including a double stranded promotor sequence derived from the first primer.

This first double stranded DNA molecule is subsequently used for the preparation of a plurality of RNA transcripts (RNA-) by a DNA-dependent RNA polymerase. The sequence downstream of the promotor site is used as template meaning that the RNA transcripts will not include the anchor sequence of the forward primer.

It will be obvious for the person skilled in the art that the choice of the DNA-dependent RNA polymerase is dependent on the choice of the promoter sequence in the first primer. In a preferred embodiment of the present invention, the promoter sequence is the T7 promoter sequence and the DNA-dependent RNA polymerase is the T7 polymerase.

In a further preferred embodiment, the method according to the invention further comprises the following steps:

(g) annealing of the second primer to the RNA transcripts produced in step (f);

(h) extending the second primer in a reaction catalyzed by the DNA polymerase to form a second RNA/cDNA hybrid nucleic acid molecule;

(i) selectively removing the RNA of the second RNA/cDNA hybrid molecule to obtain a second single stranded cDNA molecule;

(j) annealing the first primer to the obtained second single stranded cDNA sequence;

(k) extending the 3' end of the second single stranded cDNA molecule in a reaction catalyzed by the DNA polymerase using the first primer as a template to form a second partly double stranded DNA molecule comprising a double stranded promotor site;

(l) employing the second partly double stranded DNA molecule of step (k) in the preparation of a plurality of RNA transcripts complementary to the target RNA sequence in a reaction catalyzed by the DNA-dependent RNA polymerase with specificity for the promotor sequence in the first primer.

Figure 16B:
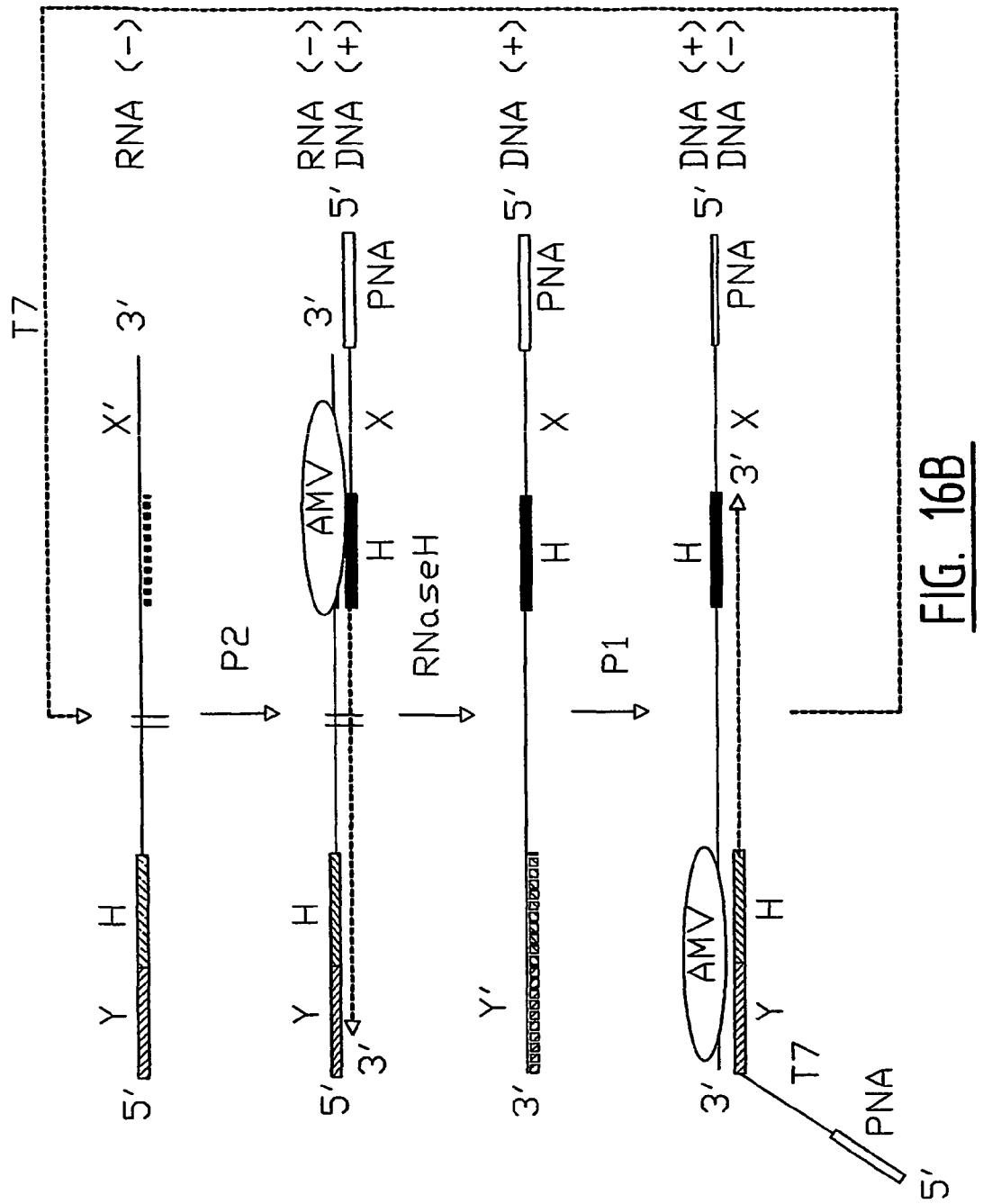

These additional steps of the amplification method according to the present invention result in a self-sustained (or cyclic) amplification of the target RNA sequence, which is also schematically represented in FIG. 16B.

In a preferred embodiment of the present invention, the first primer comprises, going from the 5' end to the 3' end, an anchor, a transcription enhancing sequence, and a hybridizing sequence consisting of 7 to 14 nucleotides which are complementary to a first segment of the target RNA sequence of 7 to 14 contiguous nucleotides.

In a further preferred embodiment, the second primer comprises of, going from the 5' end to the 3' end, an anchor, an amplification enhancing sequence, and a hybridizing sequence consisting of 7 to 14 nucleotides which are complementary to a the first segment of the first single stranded cDNA sequence of 7 to 14 contiguous nucleotides.

Preferably, the hybridizing sequence of the first and second primer comprises 7 to 10 nucleotides which are complementary to a the first segment of the RNA target sequence or the first single stranded cDNA sequence of 7 to 10 contiguous nucleotides, respectively.

Due to the presence of the anchor, the primer is able to bind specifically to the target RNA sequence. The hybridizing sequence alone would not be able to bind specifically, due to its short length.

According to the invention, the anchor can be any compound which is capable of binding to a second segment of the target RNA sequence. The anchor preferably is an, optionally modified, oligonucleotide or a protein. Preferred is an, optionally modified, oligonucleotide which comprises 7-22, optionally modified, nucleotides, more preferably 7-14 , most preferably 9-14 nucleotides, whichs bind to the second segment of the target RNA sequence or the second segment of the single stranded cDNA sequence. The person skilled in the art will understand that for binding of the anchor it is not required that all nucleotides in the anchor are complementary to the corresponding sequence in the second segment of the target RNA sequence. Thus, for specific binding of the primer to the target RNA sequence approximately at least 90% of the nucleotides of the anchor should be complementary. This allows for a more flexible selection of the second segment without influencing the efficiency of the amplification process.

The nucleotides of the anchor can be both RNA and DNA, or modified nucleotides, such as locked nucleic acids (LNA) or 2'-O-methyl modified nucleotides, or peptide nucleic acids (PNA). Such modifications provide either a more stable anchor or enhance the specific binding characteristics of the primer.

Proteins, or fragments derived thereof, which display specific binding to nucleic acid sequences can also be used as the anchor. Proteins, or fragments derived thereof, which are capable of binding to the second segment of the target RNA sequence or the second segment of the first single stranded cDNA sequence can be selected or designed by for example protein engineering. Examples of such proteins are polyC-binding proteins, polyA-binding proteins, proteins comprising one or more zinc-finger, restriction enzymes, and/or antibodies and fragments thereof such as scFvs, Fabs etc.

The first and second segment of the target nucleic acid sequence preferably are separated by 0, 1, 2, 3, 4, 5 or 6 nucleotides, more preferably by 0, 1, 2, 3 or 4 nucleotides, and most preferably by 0, 1, 2 or 3 nucleotides. When more than 6 nucleotides are present between the two segments, the efficiency of the two-step annealing of the primer and thus of the amplification is reduced.

The single stranded RNA transcripts produced during amplification are extremely suitable for the use of hybridization-based detection systems with sequence-specific probes. The detection may take place at the end of the amplification using electro-chemiluminescence (ECL). A specific capture probe, attached to magnetic beads via streptavidin-biotin interaction, is used to immobilize the RNA transcript and a ruthenium-labeled detection probe hybridizes with the transcript. Also other currently known detecion methods may be used, such as for example "enzyme linked gel assay" (ELGA) or fluorescence spectroscopy.

A very elegant detection method is the use of molecular beacons. Molecular beacons are DNA oligonucleotides labeled with a fluorophore at the 5'-end. The last part of the 3'-end of the sequence is complementary to the first part of the 5'-end and a hairpin stem is formed in such as way that a quencher at the 3'-end absorbs the emitted light of the fluorophore. The hairpin loop sequence is complimentary to the target sequence of the RNA transcript. Because of the binding of the loop sequence to the target sequence, the hairpin stem opens up and the quencher becomes separated from the fluorophore. The increase in light emitted can be detected by a fluorometer. Hybridization with the RNA transcript takes place during amplification enabling "real-time" detection. To quantify the amount of target nucleic acid in a sample, a calibrator may be included, which is added prior to the isolation of the nucleic acid and is co-extracted and co-amplified with the target nucleic acid.

The detection probe may be a target-specific probe or may be a generic probe, i.e. directed against a generic sequence incorporated in the RNA transcript, such as a sequence identical to the amplification enhancing sequence.

Thus, in a preferred embodiment of the method according to the invention, the target-specific probe hybridizes to the RNA transcript, complementary to the target RNA sequence. According to another preferred embodiment, the generic probe hybridizes to the sequence identical to the amplification sequence of the second primer, enabling the use of one sequence-specific probe for the detection of a wide variety of different amplified target RNA sequences. This results in a cost effective detection method (detection probes are in general relatively expensive to synthesize), and increases the chances for reproducible and quantitative detection, since the binding characteristics of the probe could be comparable in every amplification method regardless of the starting materials or the target RNA sequence.

The amplification method of the present invention is preferably used for the amplification of viral target RNA sequences, such as RNA isolated from the human immunodeficiency virus (HIV) or RNA isolated from the human hepatitis C virus, which viruses have only partially conserved nucleic acid sequences.

The invention further relates to primers comprising an anchor and a hybridizing sequence. The primers according to the invention preferably comprise, going from the 5' end to the 3' end, an anchor, as defined above, a transcription enhancing sequence or an amplification enhancing sequence, as defined below, and a hybridizing sequence of 7 to 14 nucleotides, preferably 7 to 10 nucleotides, as defined above.

The use of the primers comprising an anchor and a hybridizing sequence is not limited to Transcription Based Amplification (TBA), but these primers can also be used in other amplification methods like the Reverse Transcriptase Polymerase Chain Reaction (RT-PCR).

According to another aspect of the present invention, the invention relates to a kit for the amplification and/or detection of a target RNA sequence comprising at least one or more primers according to the invention.

The kit according to the invention may further comprise one or more sequence-specific probes, an amplification buffer, and/or one or more enzymes, such as a DNA polymerase, RNAse H, and a DNA-dependent RNA polymerase.

Definitions

According to the present invention a target RNA sequence is defined as a specific segment of RNA which is to be amplified by an amplification method.

Hybridization is defined as the binding of a contiguous number of nucleotides, present in for example a primer, to the complementary nucleotides of for example a target RNA sequence. The hybridization results in the formation of a double stranded nucleic acid molecule.

Annealing is defined as the association of a primer with a target nucleic acid sequence by for example hybridization.

Specific binding is defined as the preference for binding of a compound (such as a primer, or part of a primer) to a specific oligonucleotide sequence, as compared to the binding of said compound to a random nucleotide sequence under the used conditions. Thus a compound binds specifically if the compound only binds to one and the same nucleotide sequence.

A nucleic acid sequence is designated complementary if all individual nucleotides of the nucleic acid sequence are complementary, for example, a oligonucleotide sequence reads 5'-ATG ACC TGG-3' and the complementary oligonucleotide sequence reads 3'-TAC TGG ACC-5'.

A template is defined as a nucleic acid molecule that is to be transcribed by a polymerase. The synthesized transcript is complementary to the nucleic acid molecule, or at least to one strand of the nucleic acid molecule. Both RNA and DNA are usually synthesized in the 5' to 3' direction.

A transcription enhancing sequence is a nucleic acid sequence comprising a promotor, for example T7, which is a non-specific sequence vis-à-vis the target sequence. The transcription enhancing sequence may optionally comprise a purine stretch (mainly composed by G and/or A). It creates a loop between the anchor and the hybridizing sequence.

An amplification enhancing sequence is a non-specific nucleic acid vis-à-vis the target sequence, but it comprises no promotor, i.e. only a random sequence that generates a loop between the anchor and the hybridizing sequence.

The invention will be further exemplified by the following Figures and Examples. These Figures and Examples are not intended to limit the present invention in any way.

FIGURES

FIG. 1 shows the legend used in the graphs of the subsequent figures.

Figure 2A:
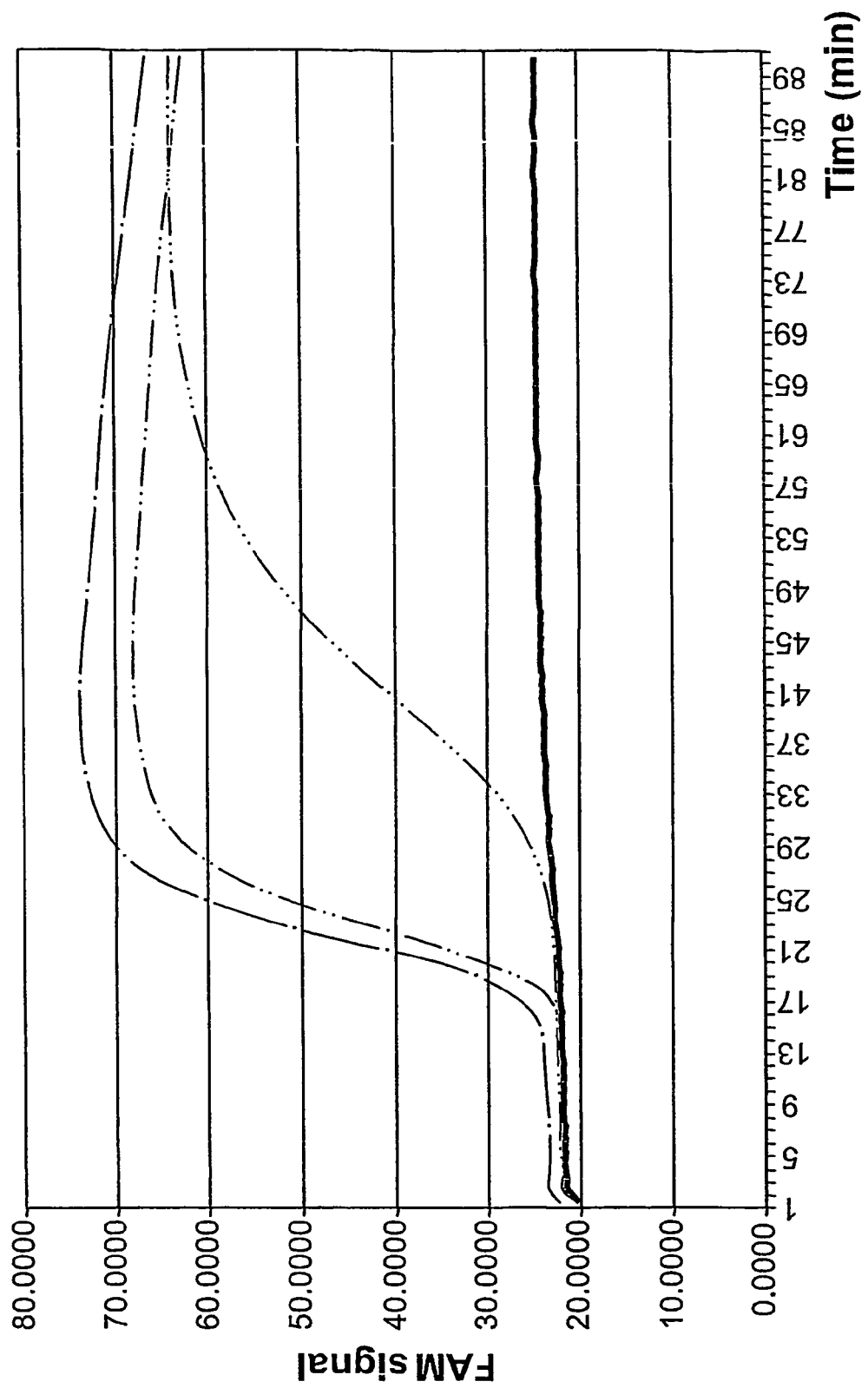
Figure 2B:
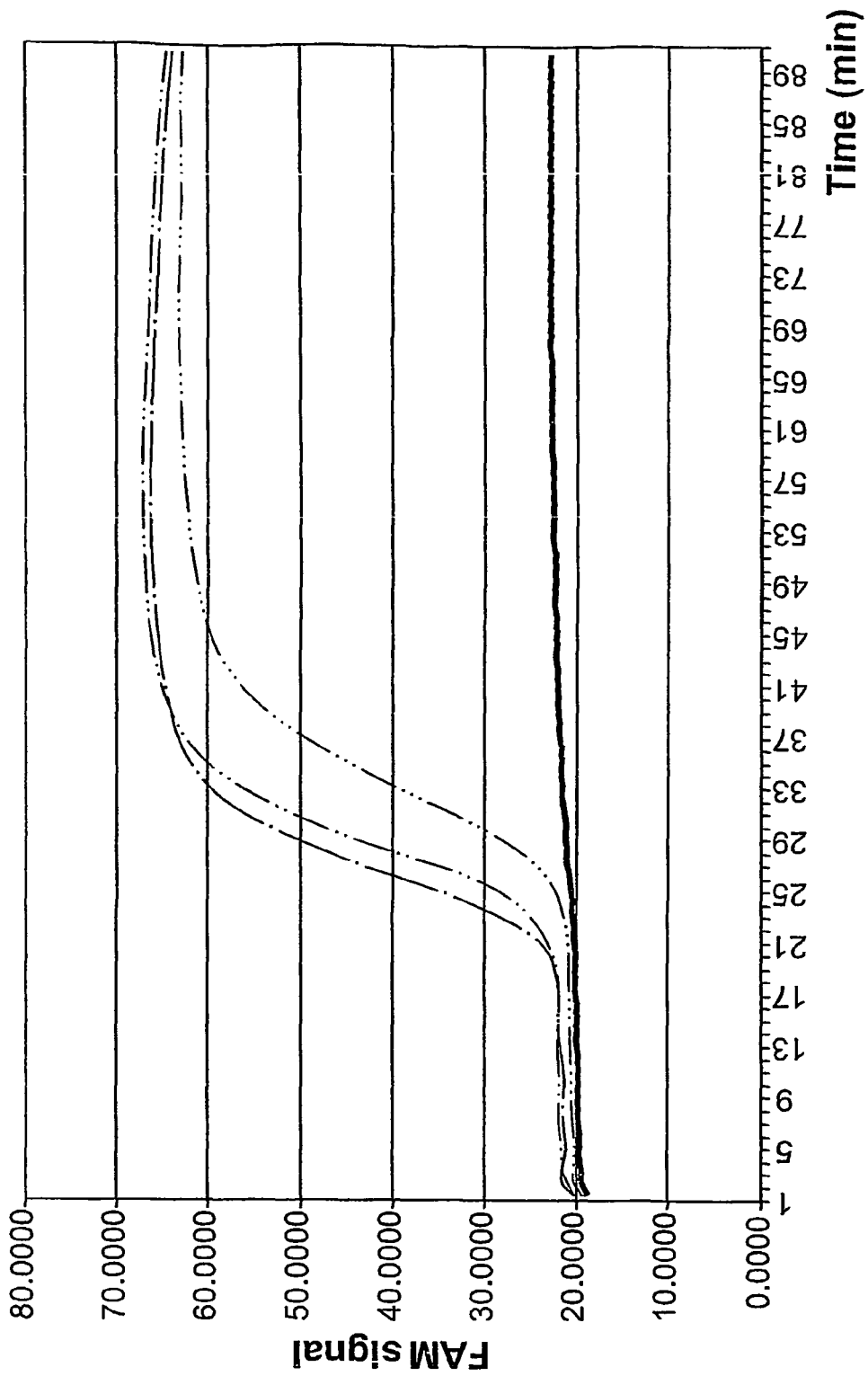

FIG. 2: Amplification of HIV RNA (RNA transcript, 500, 50 and 5 cps) with an anchor p1 primer (FIG. 2B: HIV12, table 1) or a standard p1 primer (FIG. 2A: HIV11, table 1), both in combination with a standard p2 primer (HIV2, table 1) and a molecular beacon (HIV-MB-WT, table 1) as probe. A sample without template (NT) is used as negative control.

Figure 3:
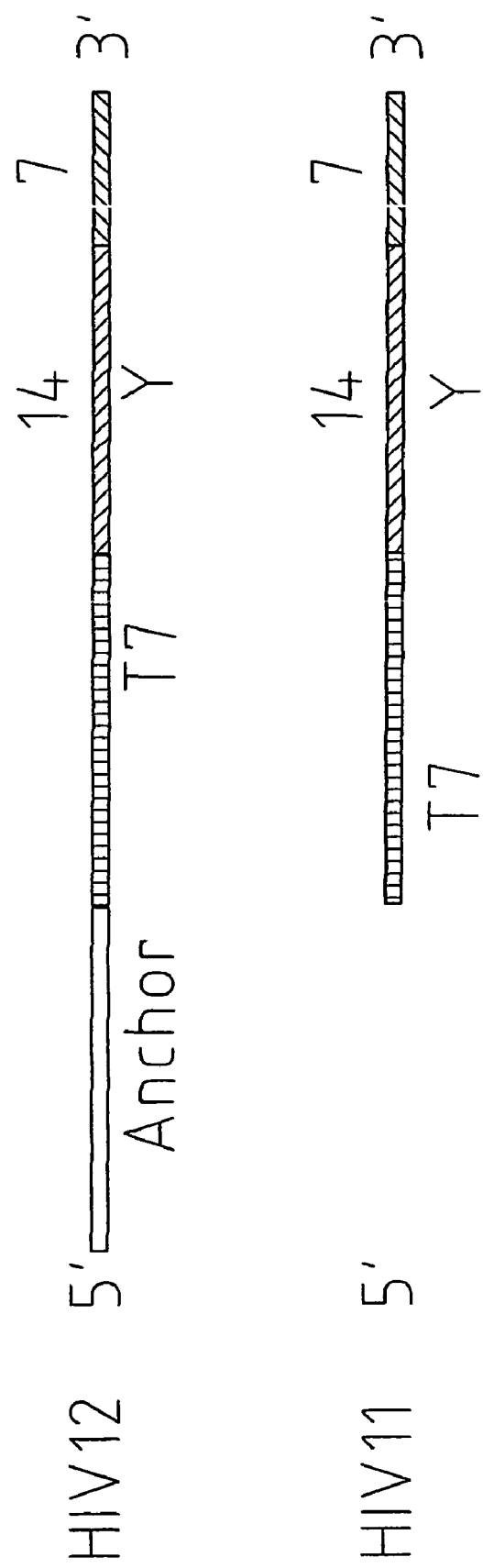

FIG. 3: Schematic representation of anchor p1 primer HIV12 (table 1) and primer HIV11 (table 1) without anchor.

Figure 4A:
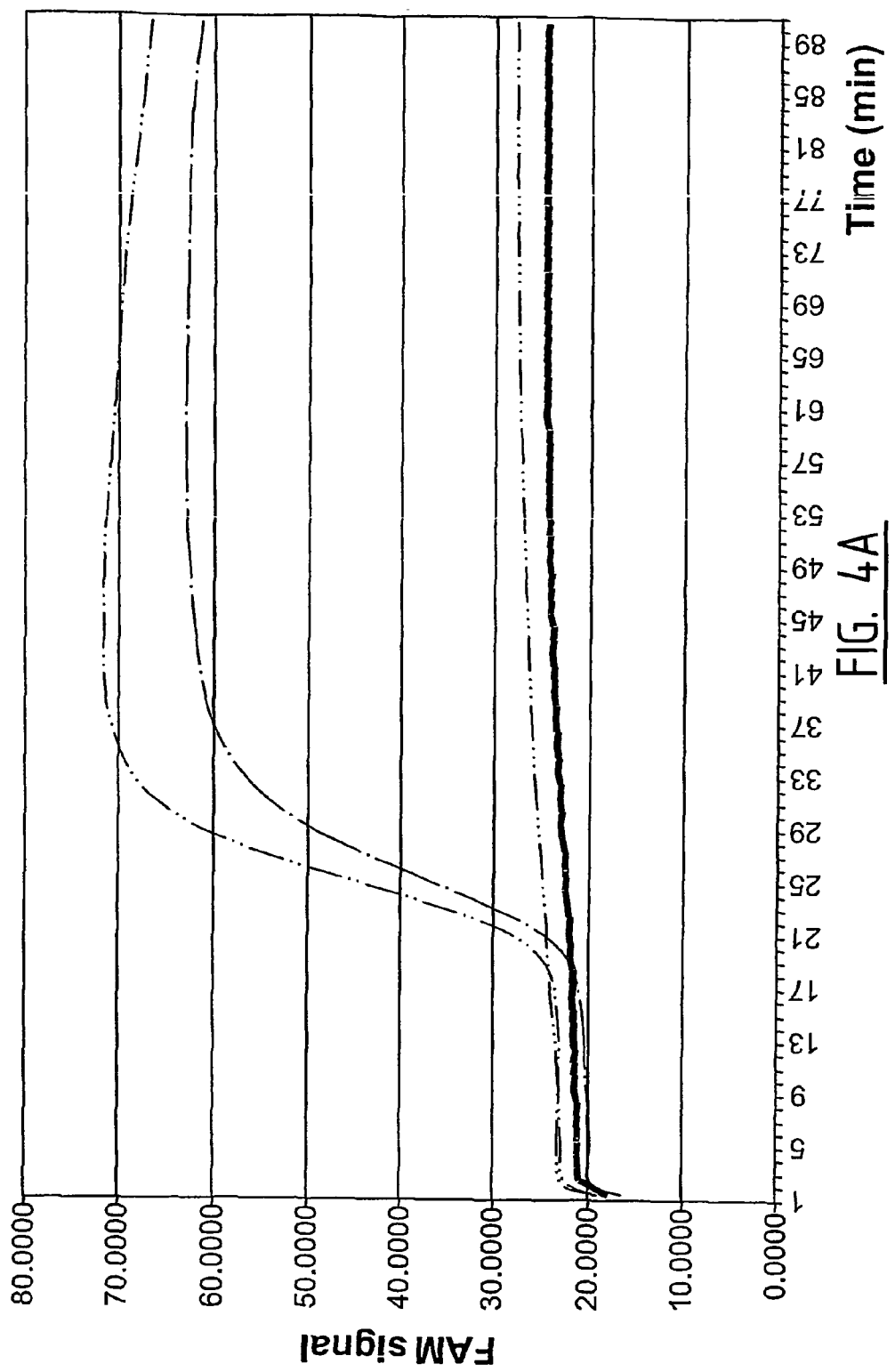
Figure 4B:
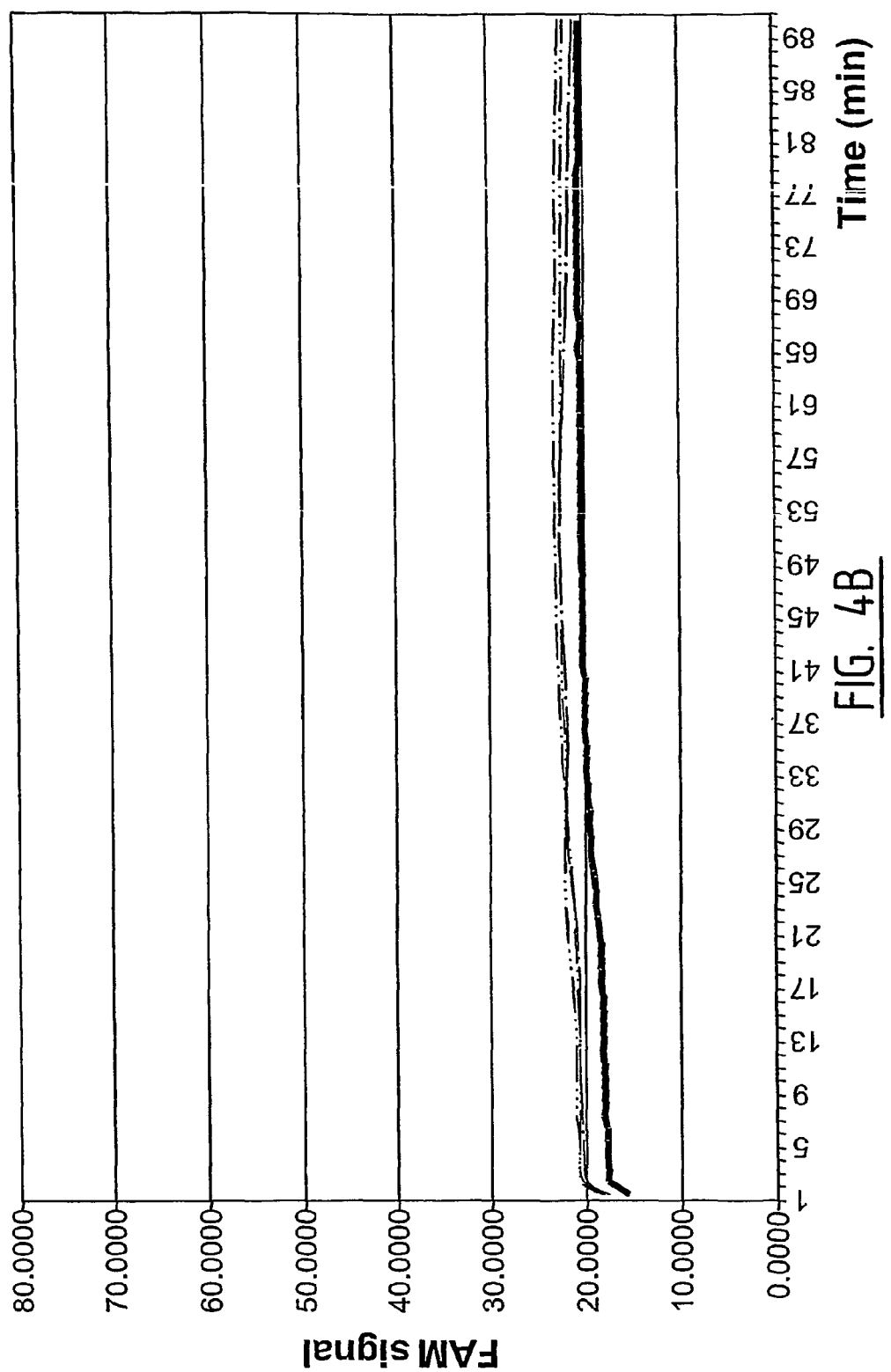
Figure 4D:
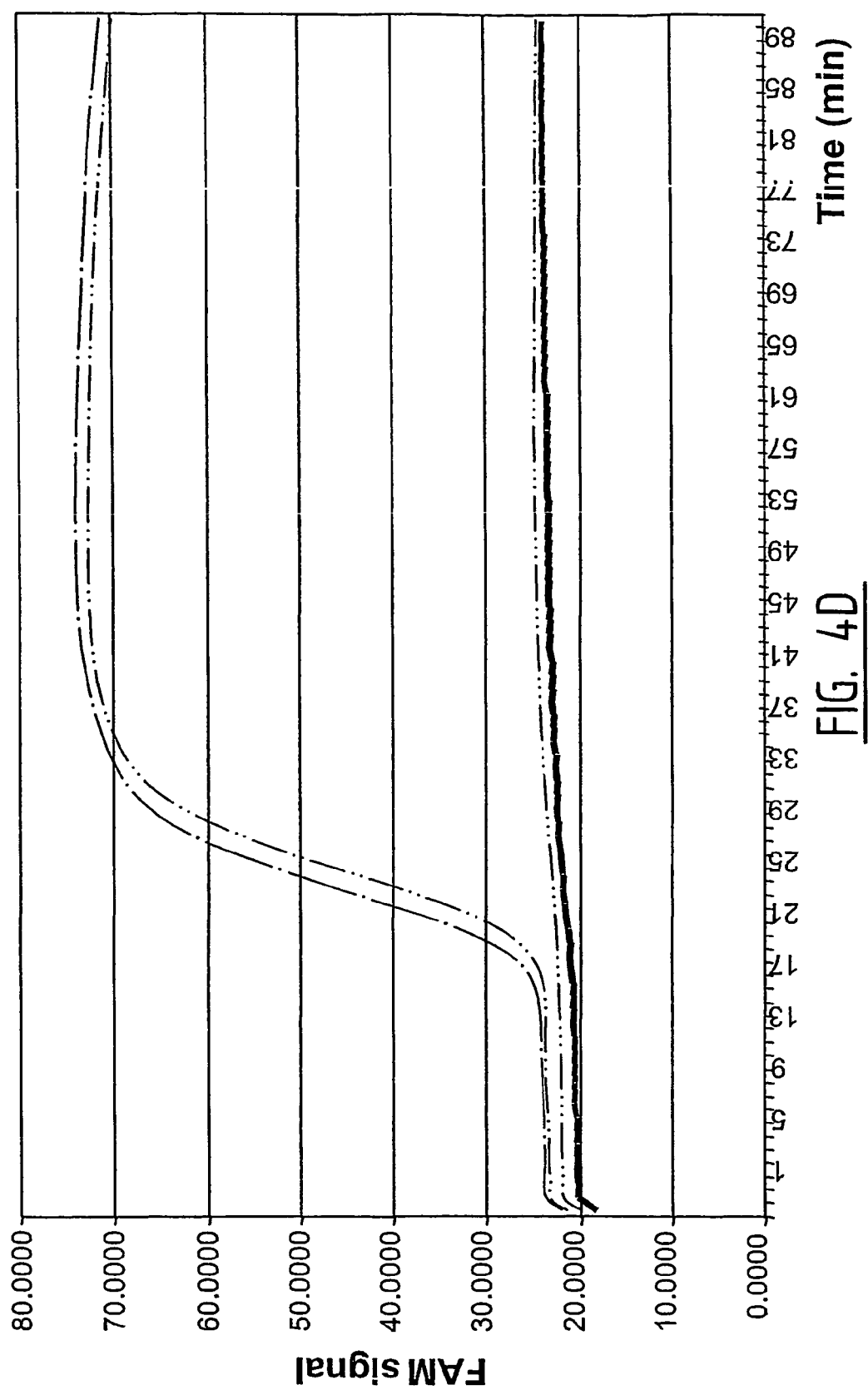
Figure 5A:
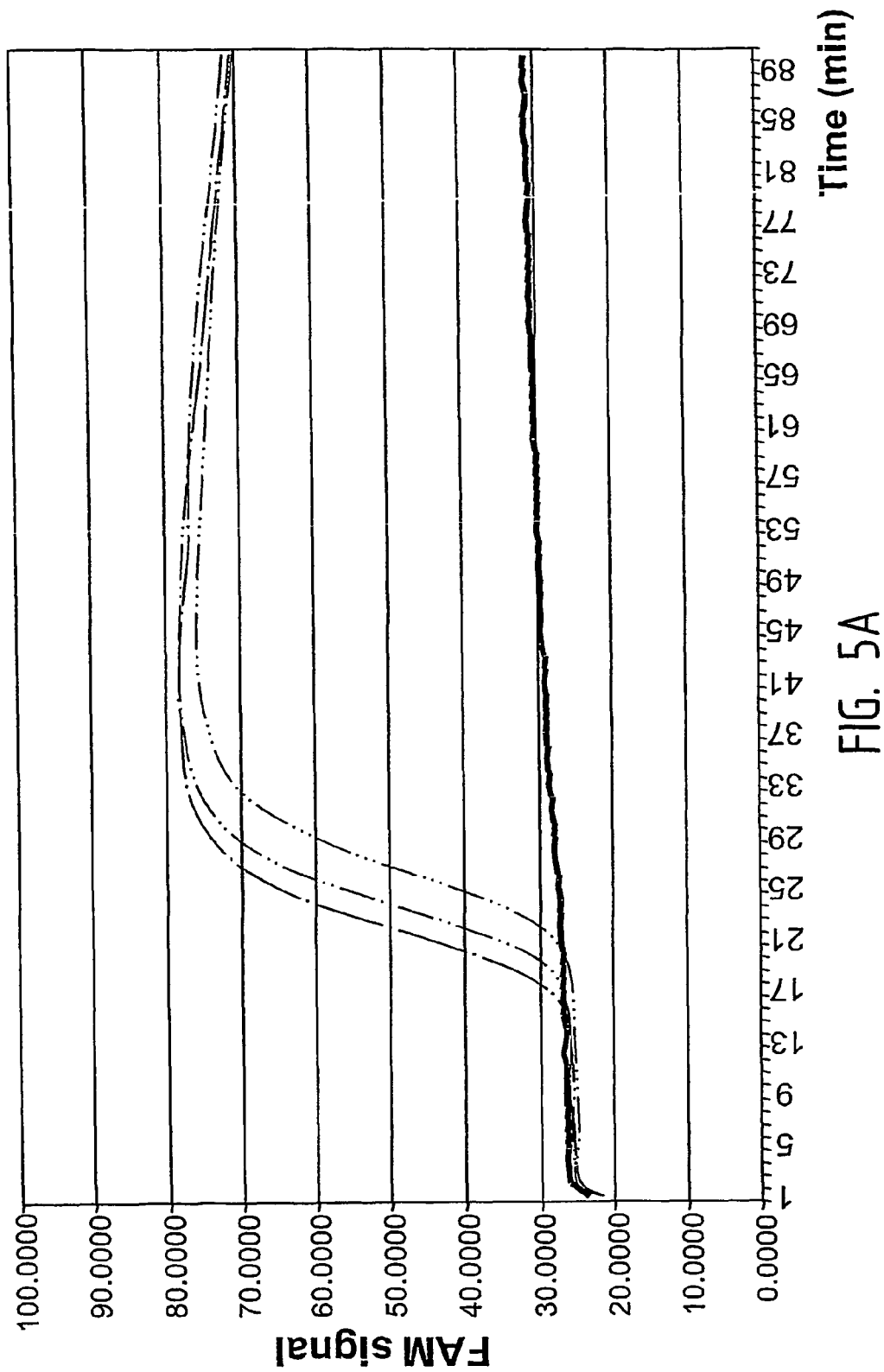
Figure 5B:
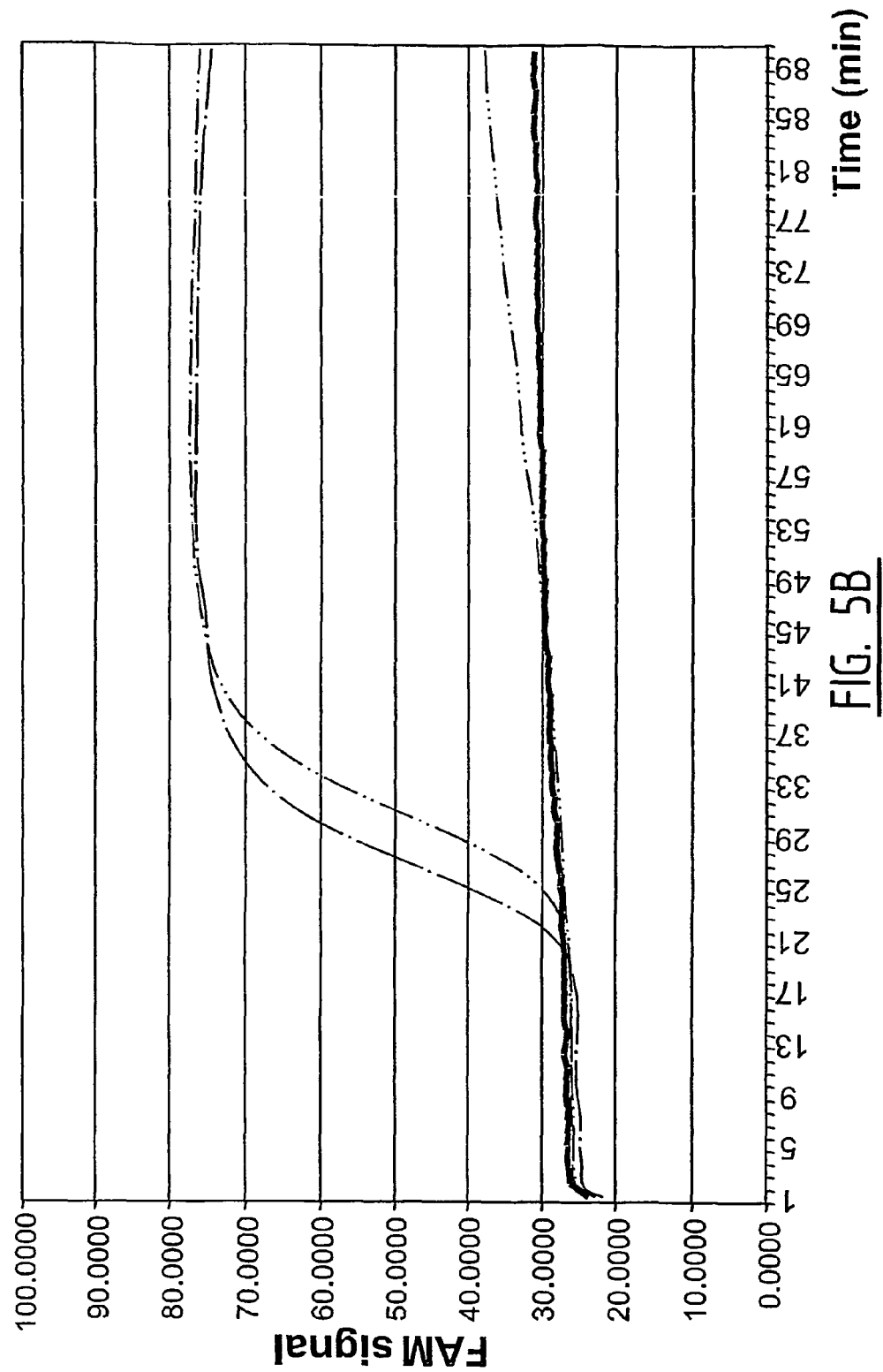
Figure 5C:
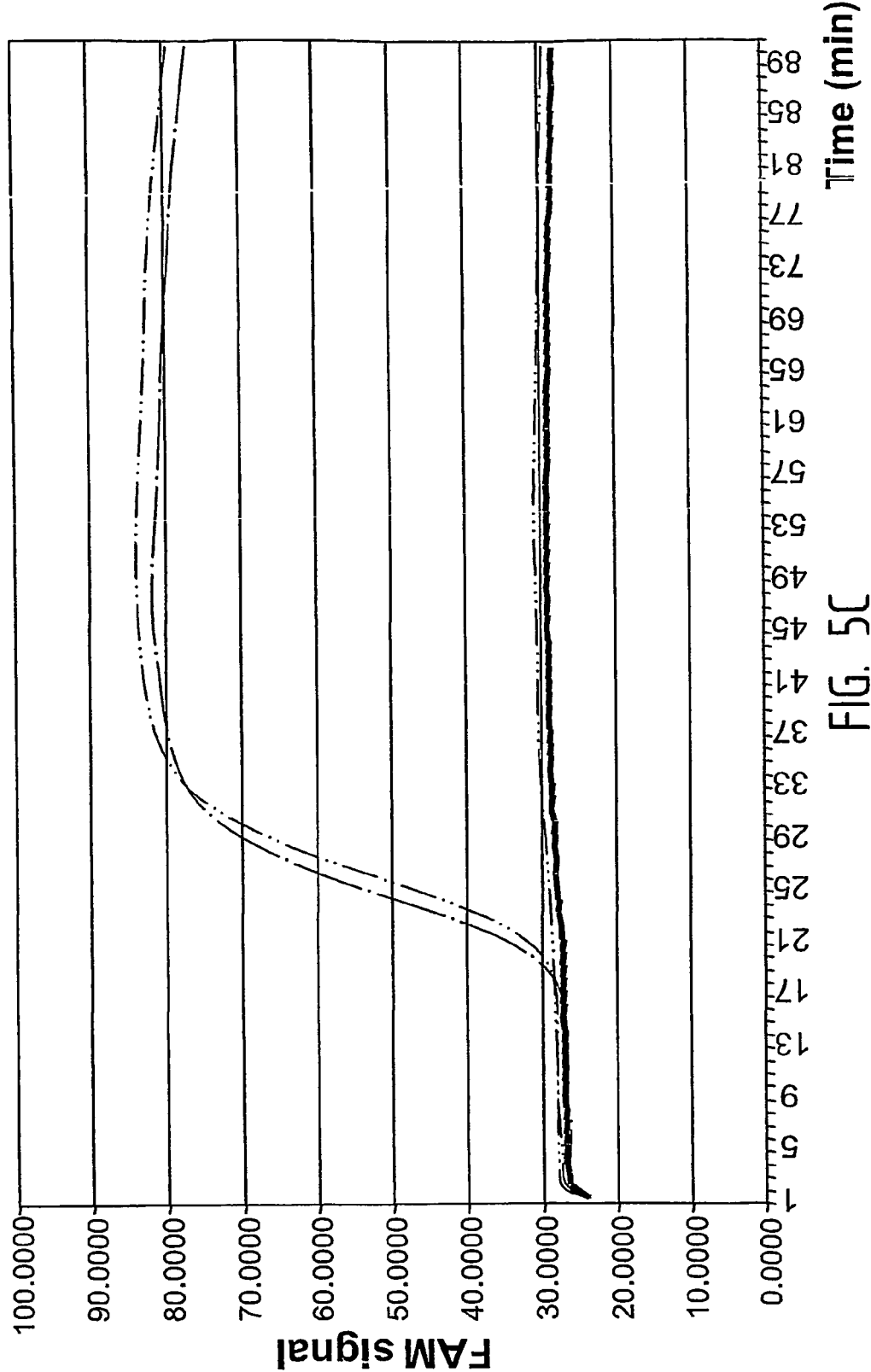
Figure 5D:
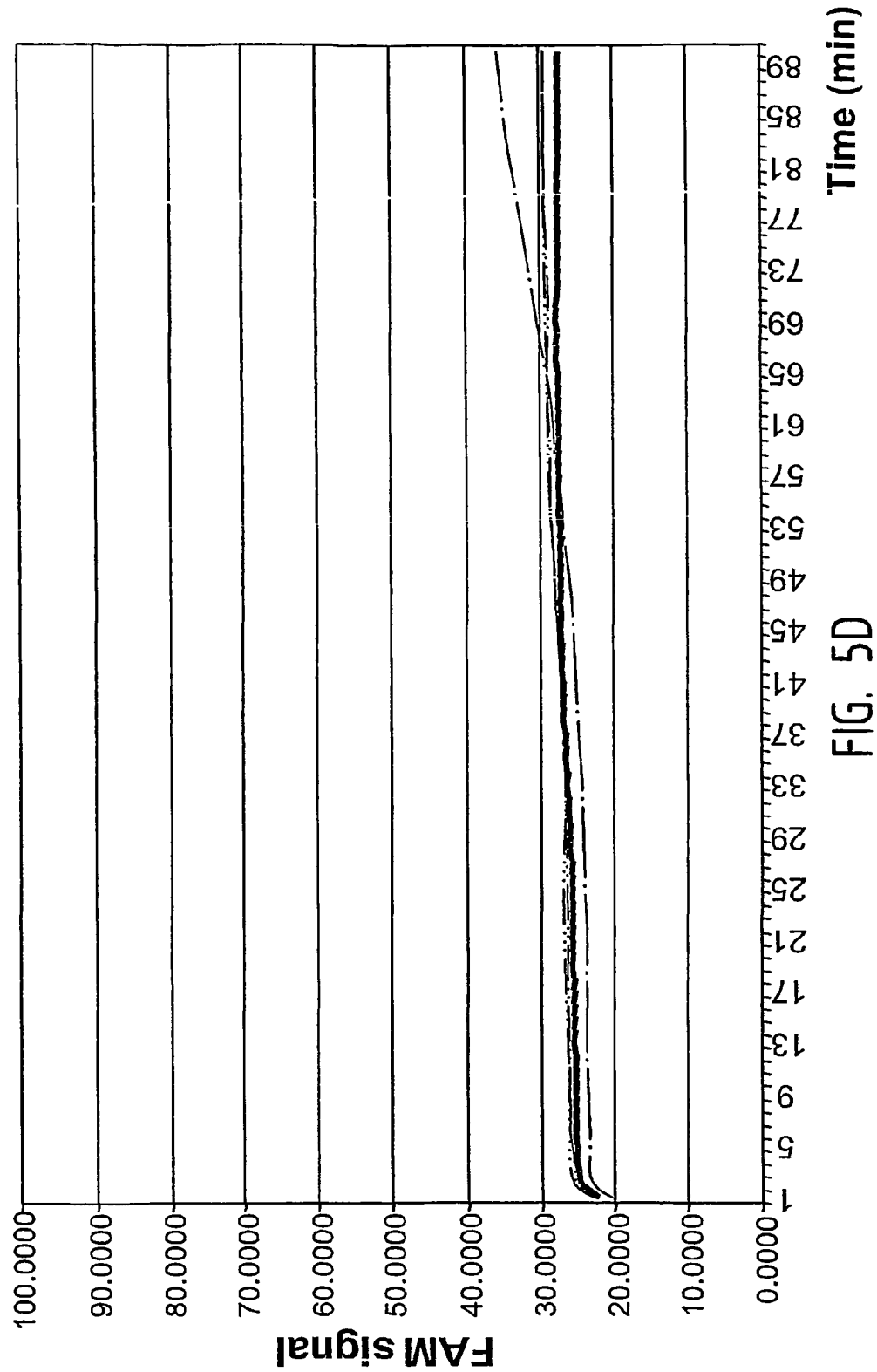
Figure 5E:
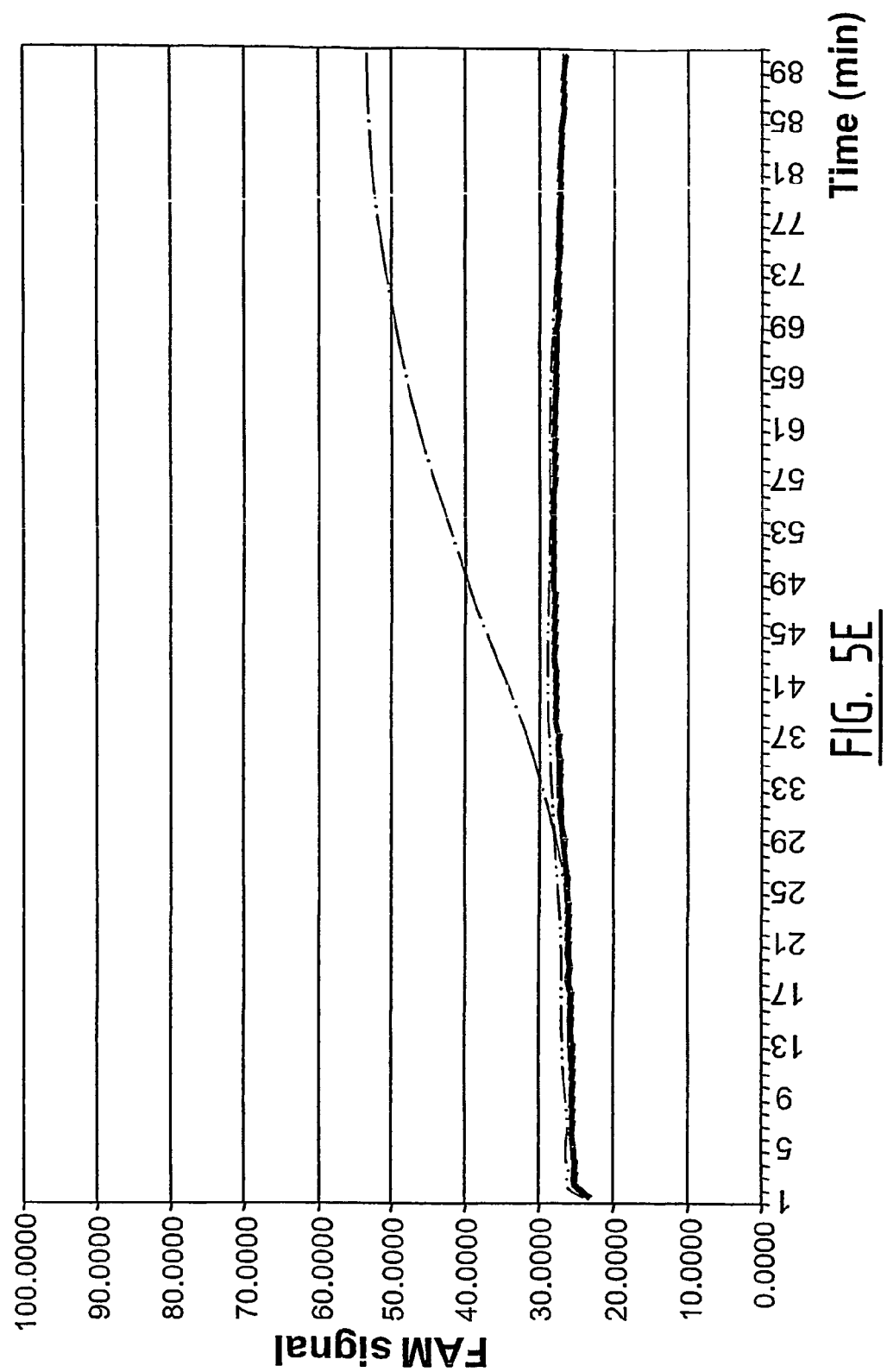
Figure 5F:
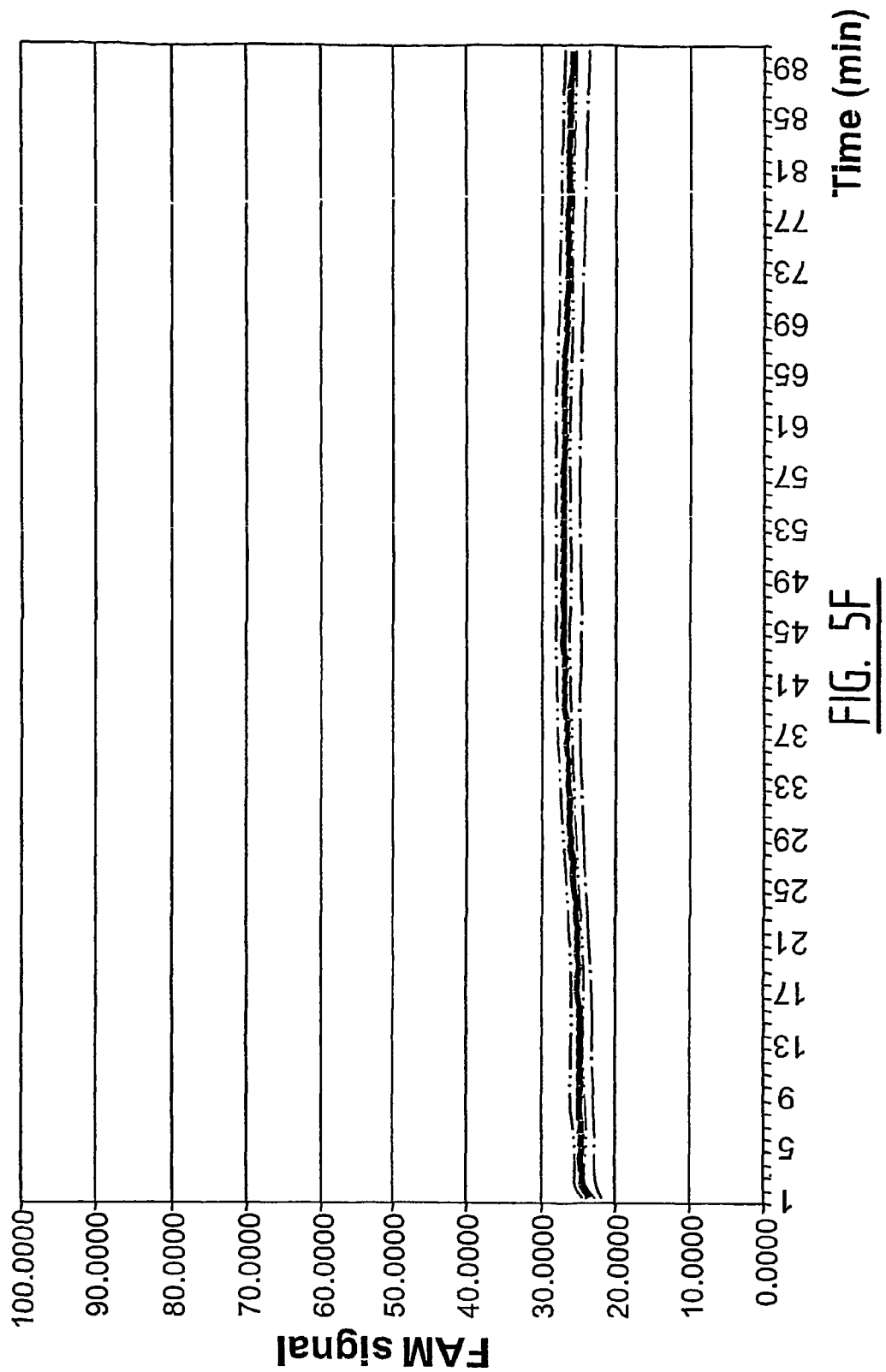

FIG. 4: Amplification of HIV RNA (RNA transcript, 500, 50 and 5 cps) with a standard p1 primer (FIG. 4A: HIV11, table 1), an anchor p1 primer (FIG. 4C: HIV12, table 1), a p1 primer without anchor (FIG. 4B: HIV11, table 1) or a combination of primer HIV12 and HIV11 (FIG. 4D). All in combination with a standard p2 primer (HIV2, table 1) and a molecular beacon (HIV-MB-WT, table 1) as probe. A sample without template (NT) is used as negative control.

FIG. 5: Amplification of HIV RNA (Total viral RNA, 500, 50 and 5 cps) with a standard p1 primer (FIG. 5A: HIV11, table 1), anchor primers with different anchor lengths varying from 22 to 7 nucleotides (HIV12 (FIG. 5B), 17 (FIG. 5C), 20 (FIG. 5D), 21 (FIG. 5E), 22 (FIG. 5F), table 1). All in combination with a standard p2 primer (HIV2, table 1) and a molecular beacon (HIV-MB-WT, table 1) as probe. A sample without template (NT) is used as negative control.

Figure 6A:
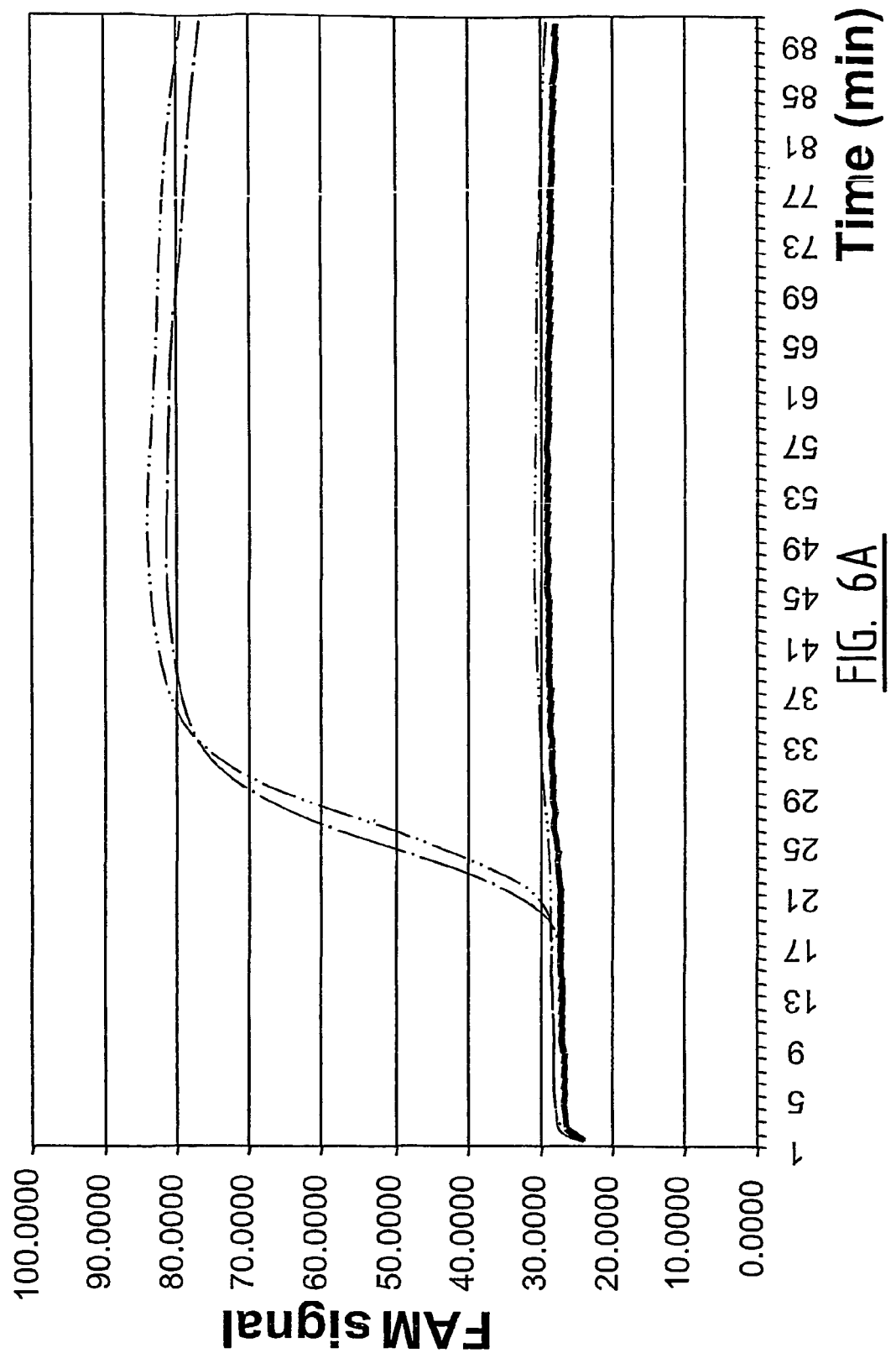
Figure 6B:
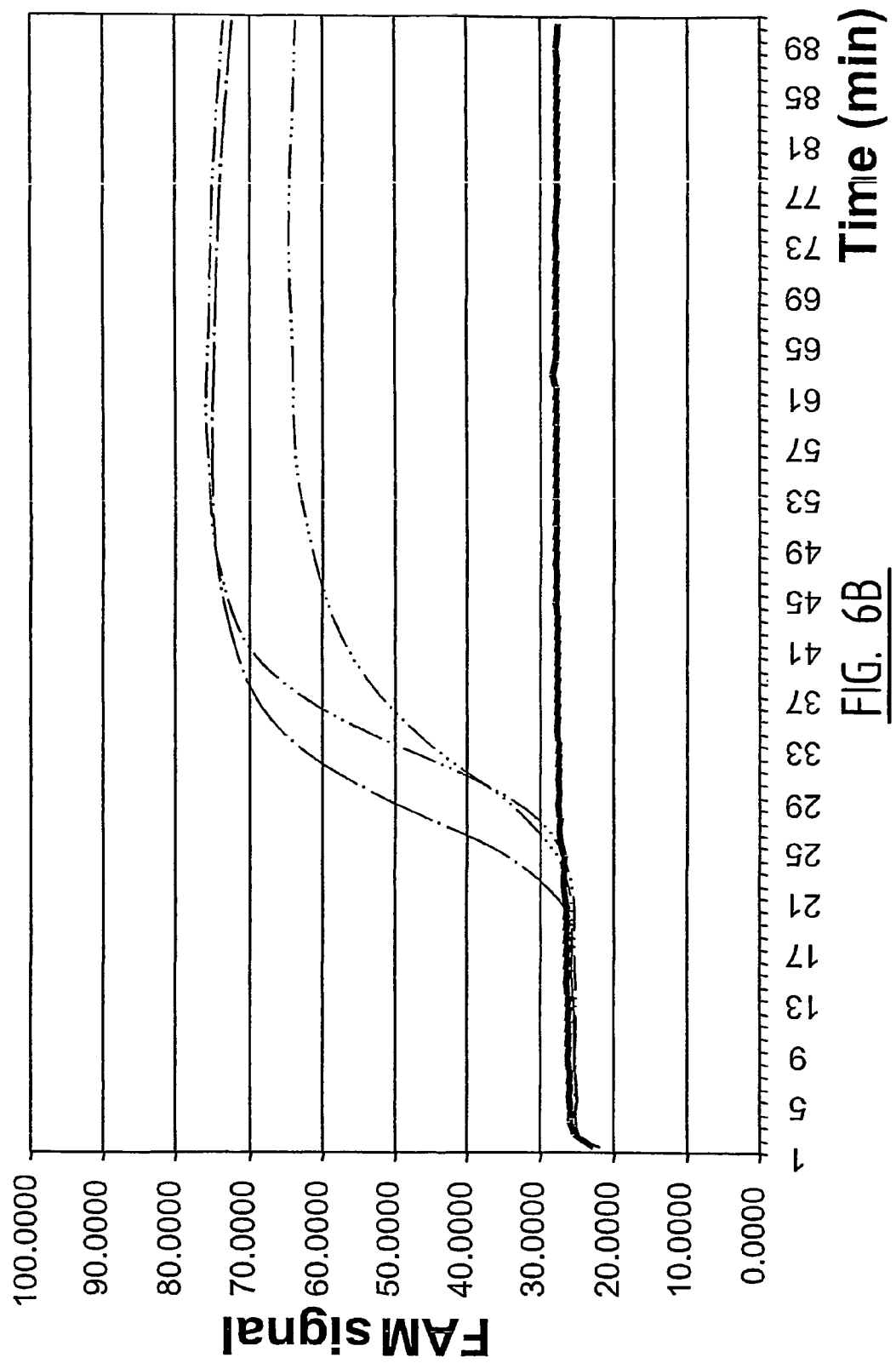
Figure 7A:
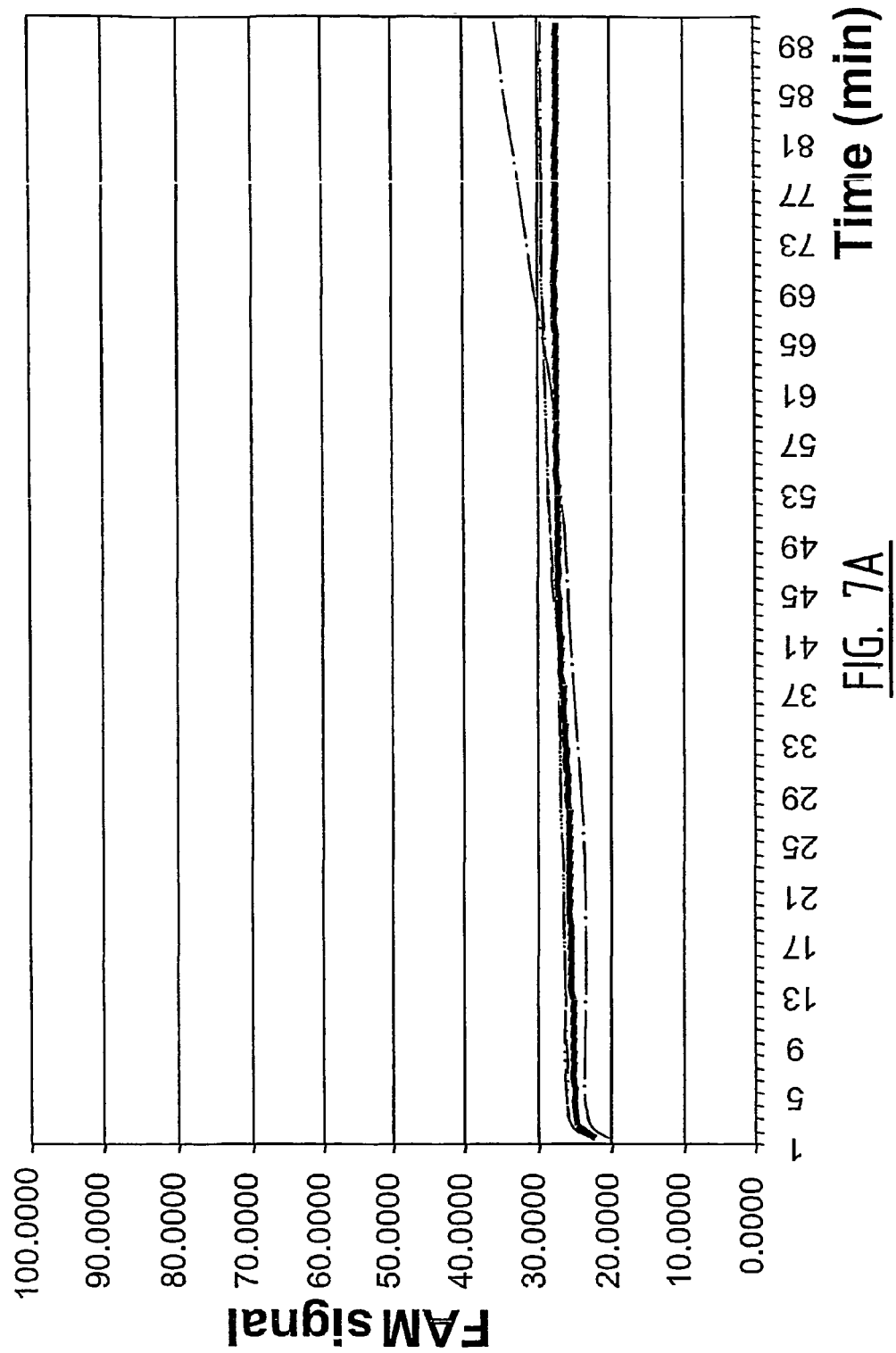
Figure 7B:
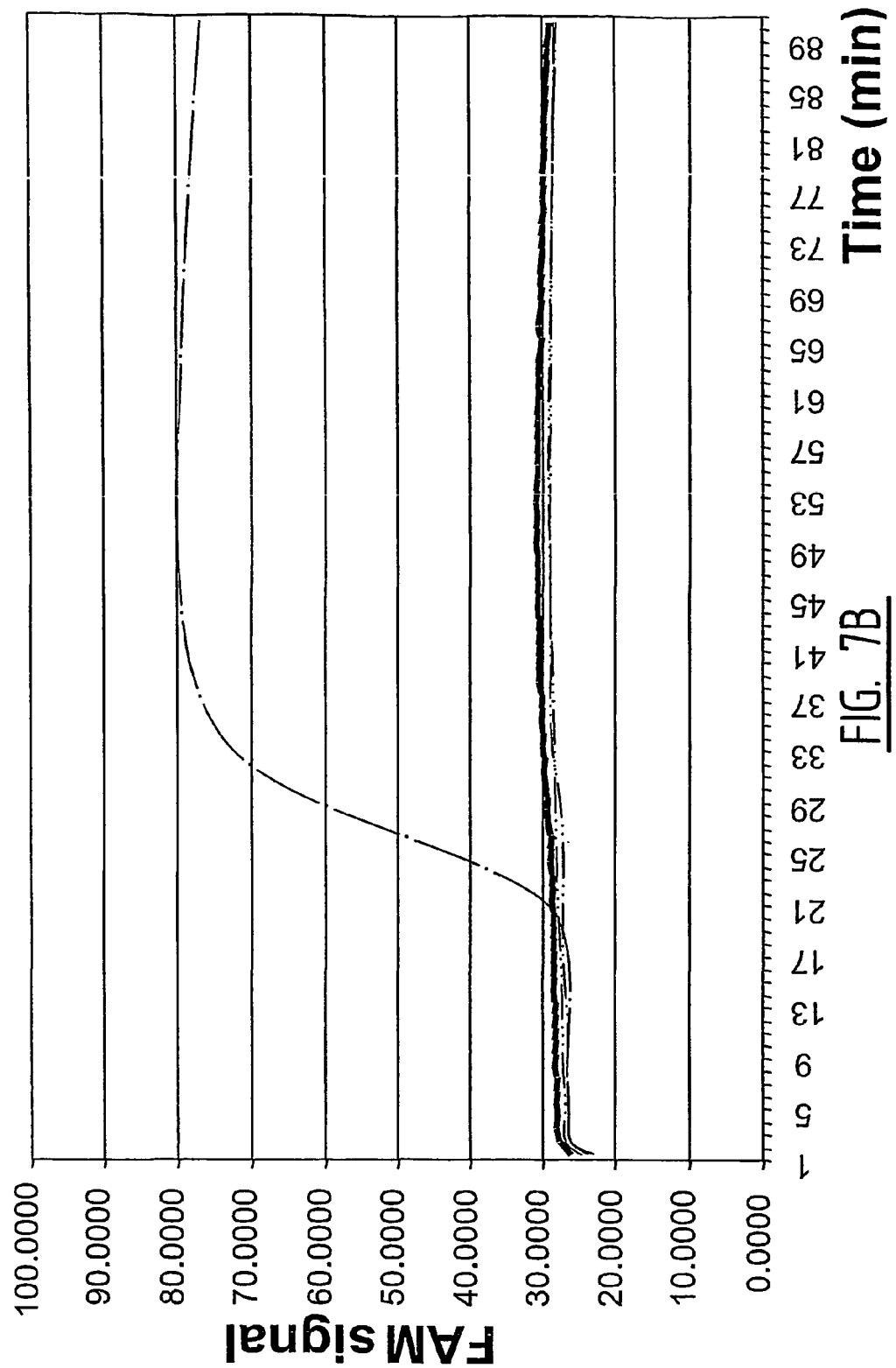
Figure 7C:
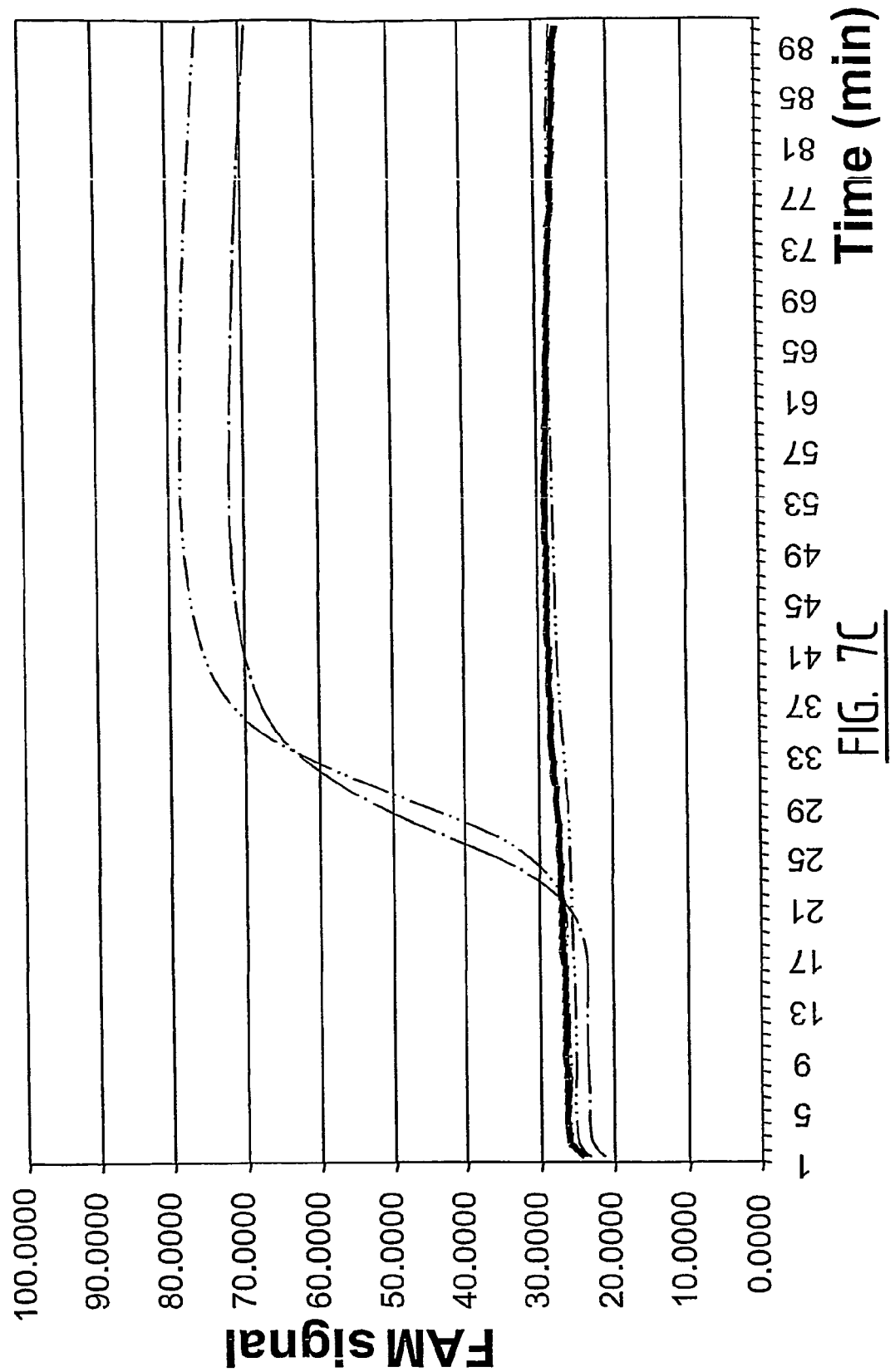
Figure 8A:
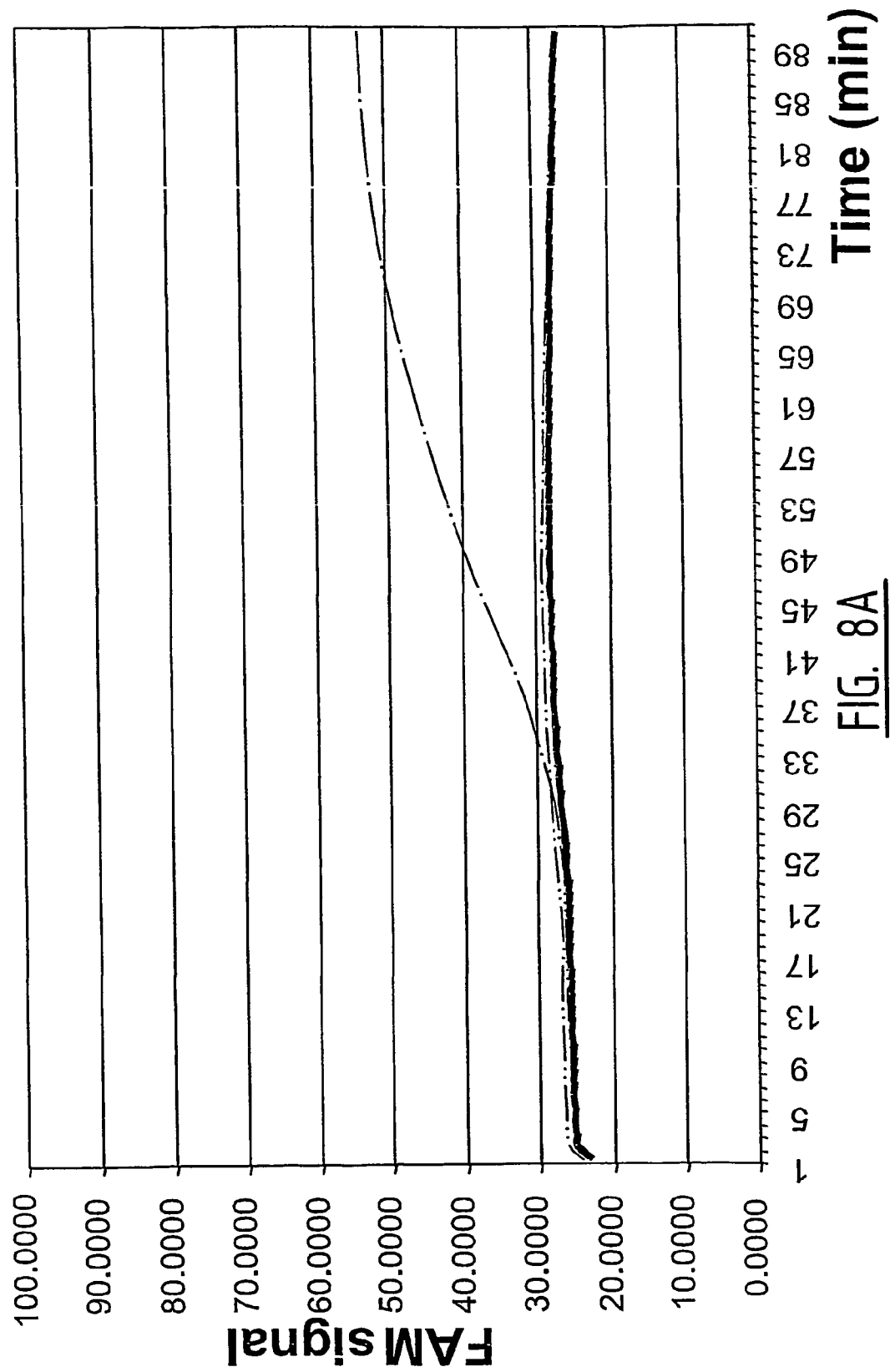
Figure 8B:
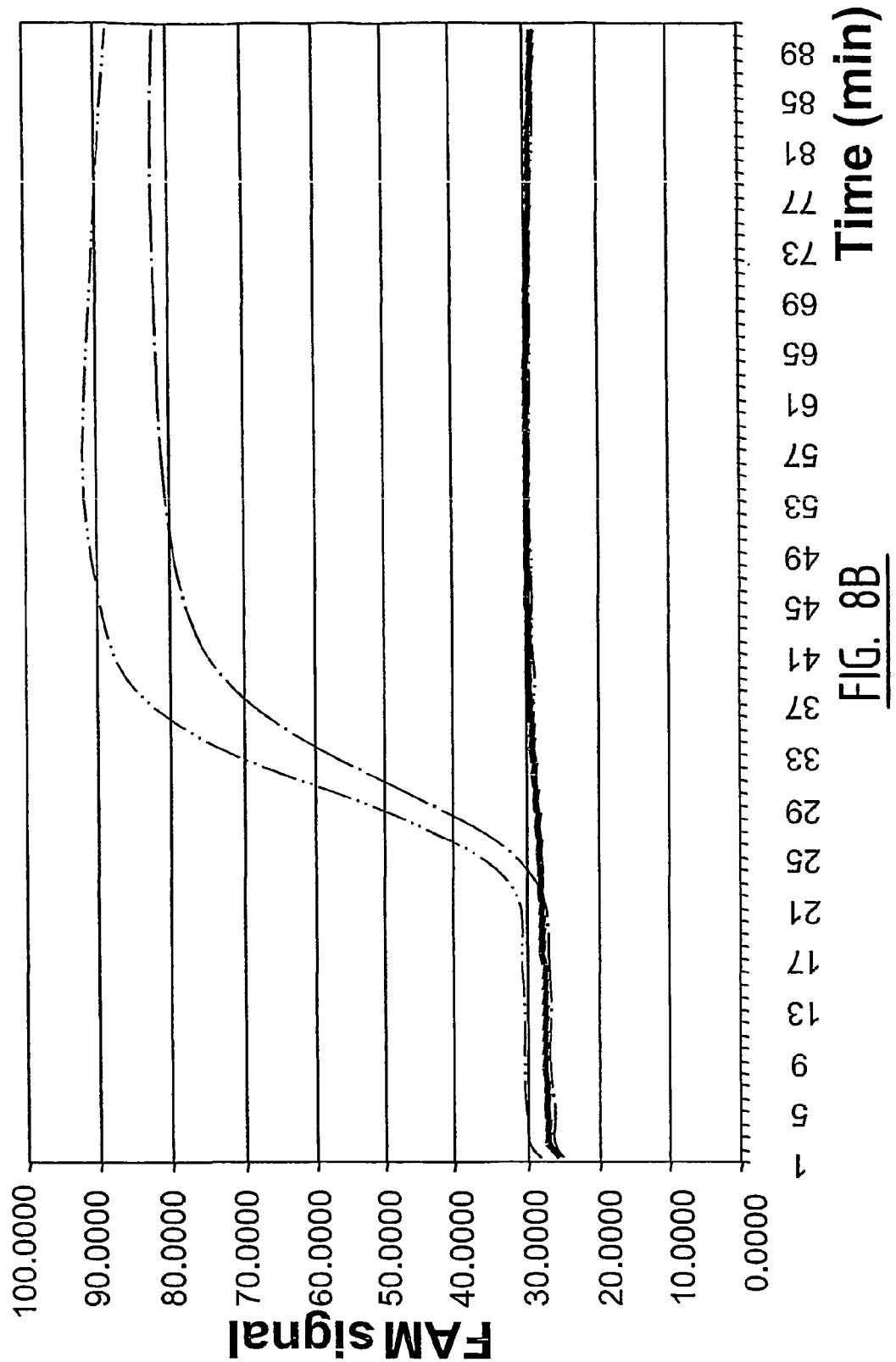
Figure 8C:
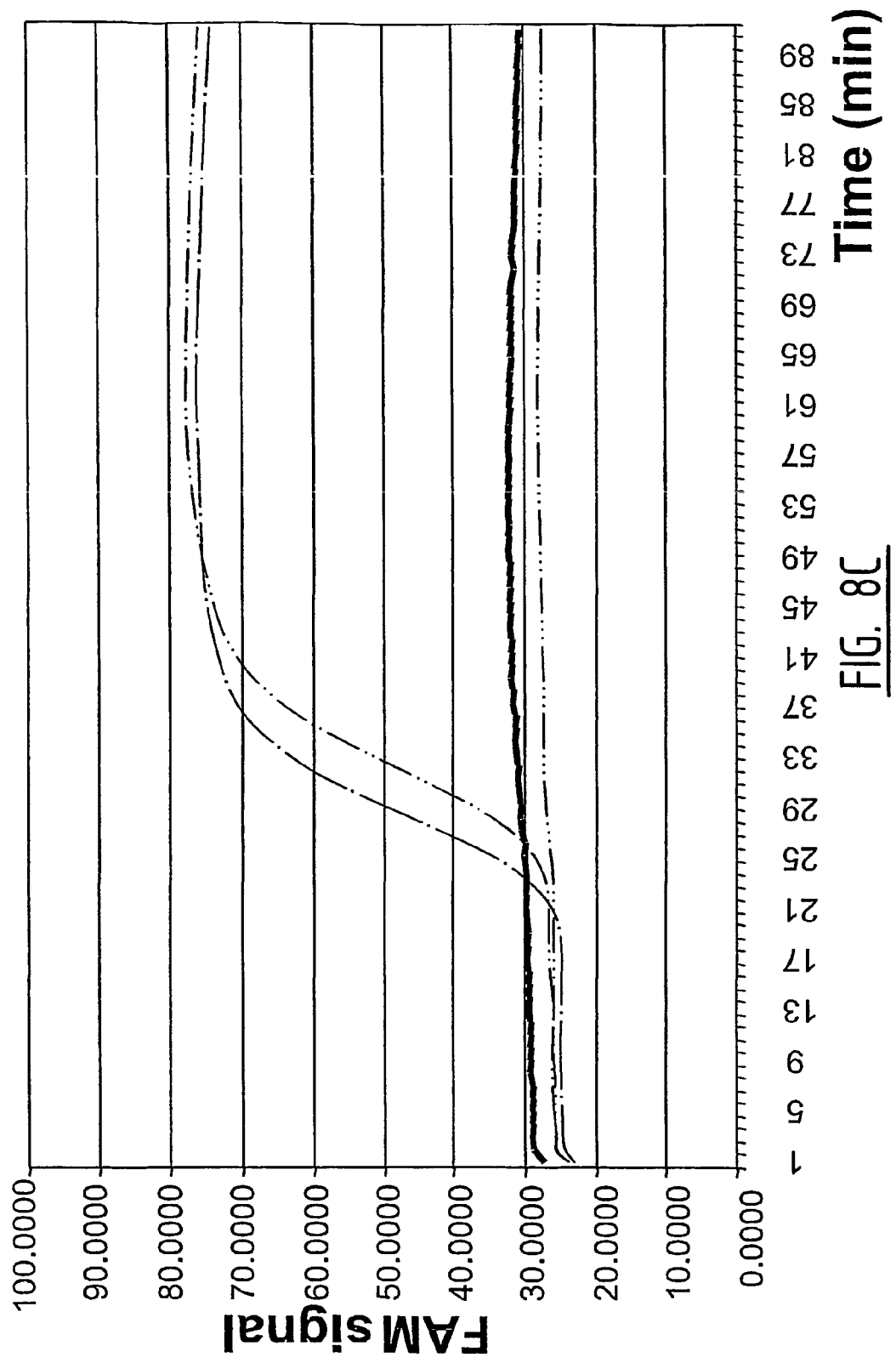
Figure 9A:
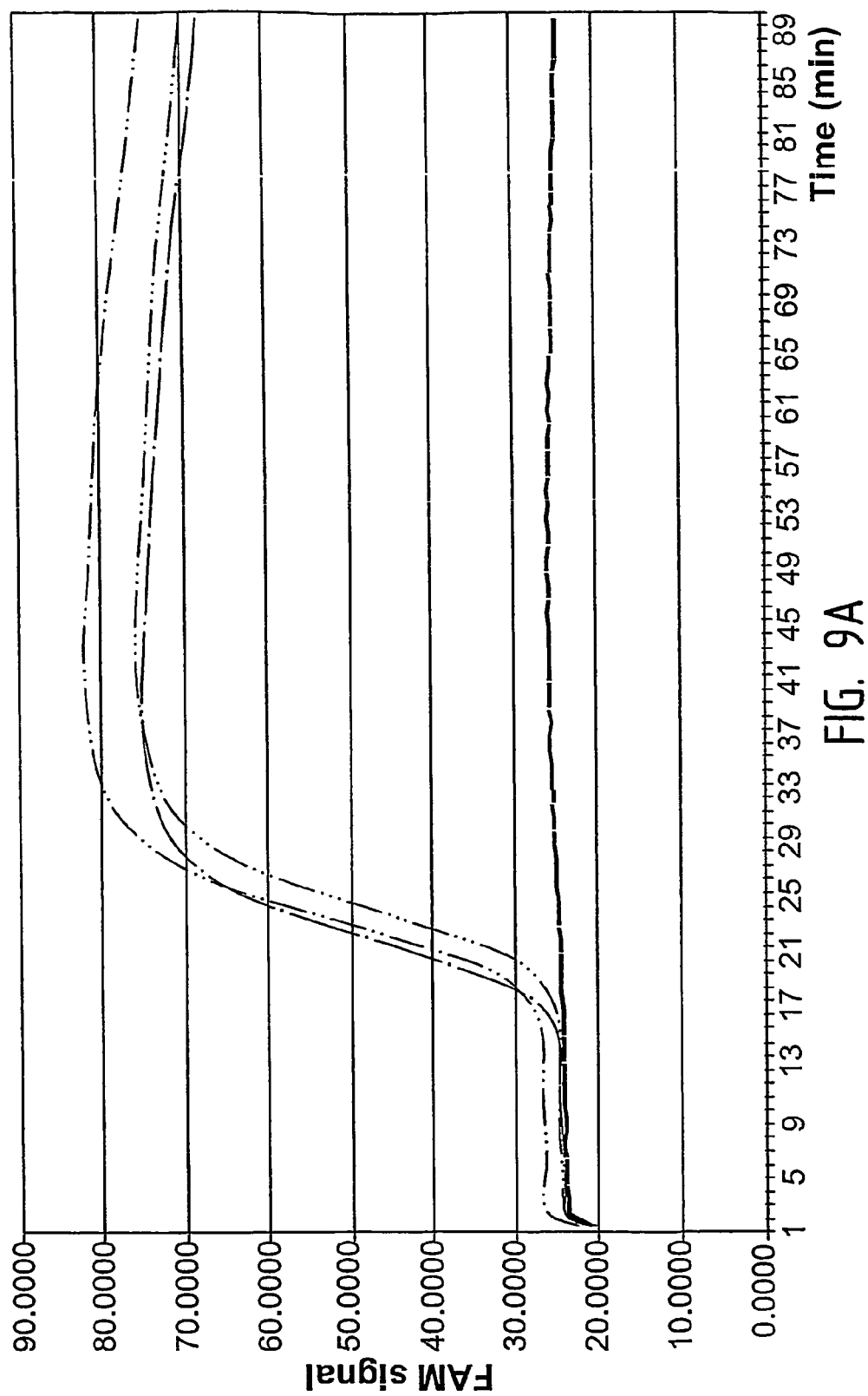
Figure 9B:
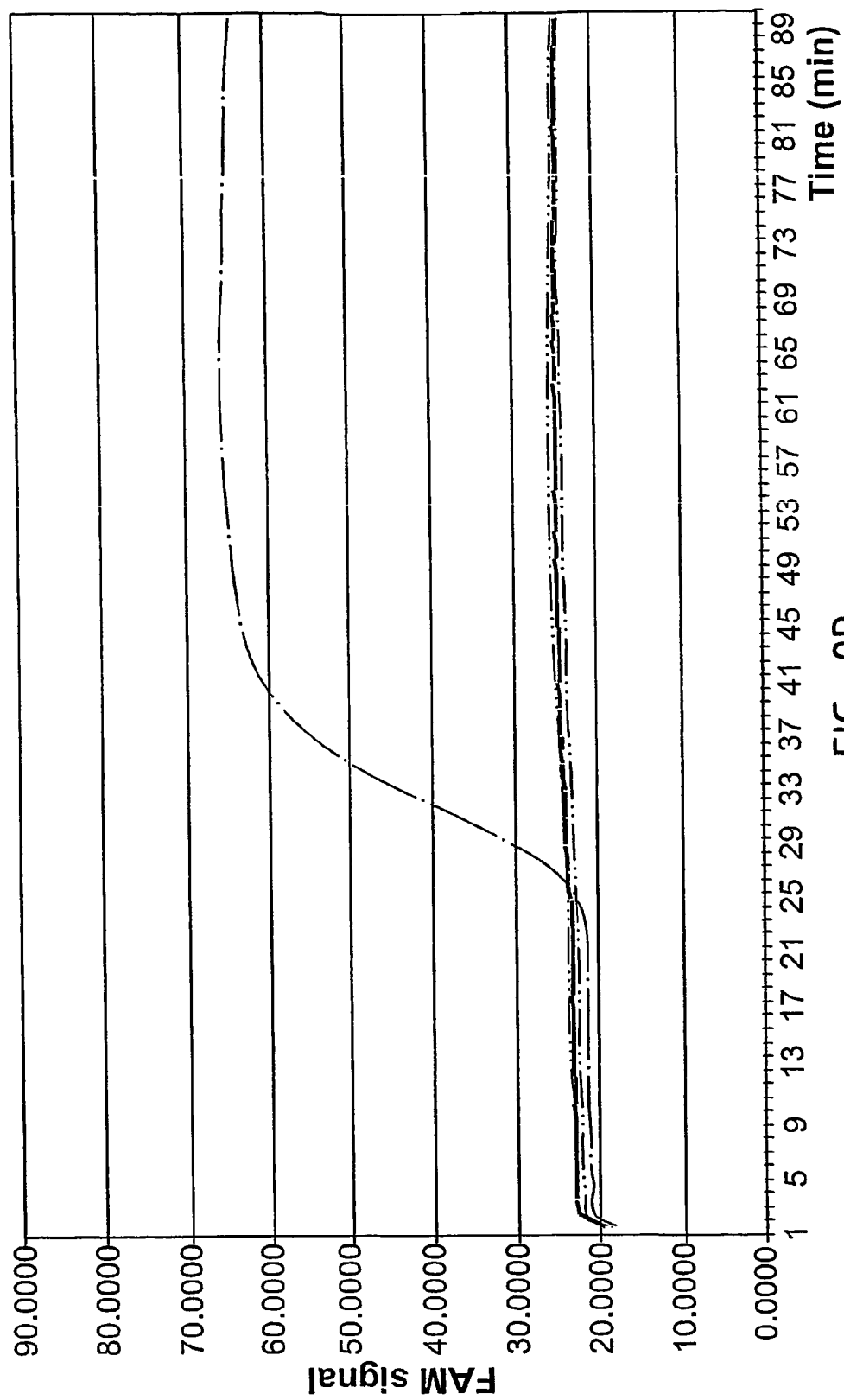
Figure 9C:
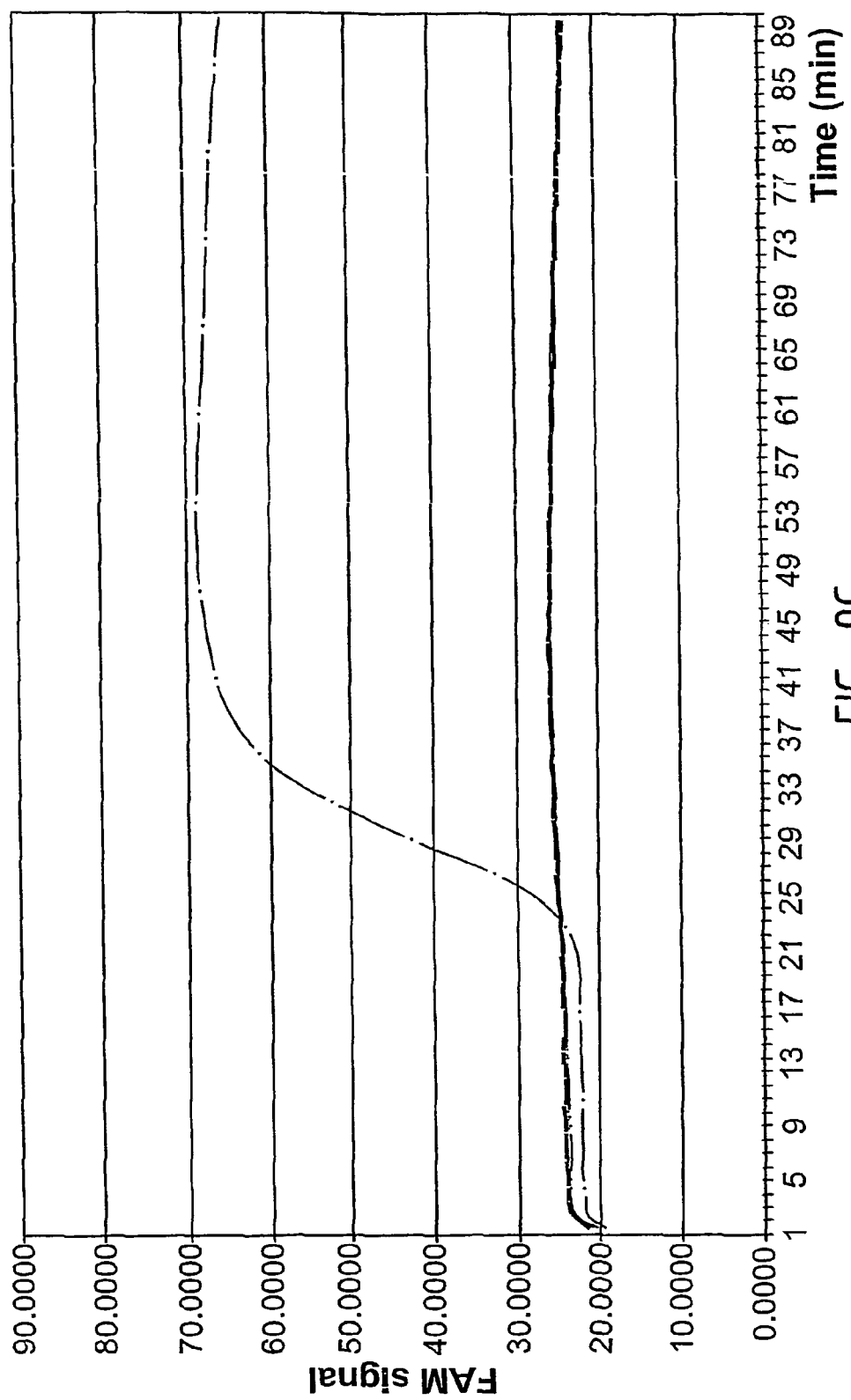
Figure 9D:
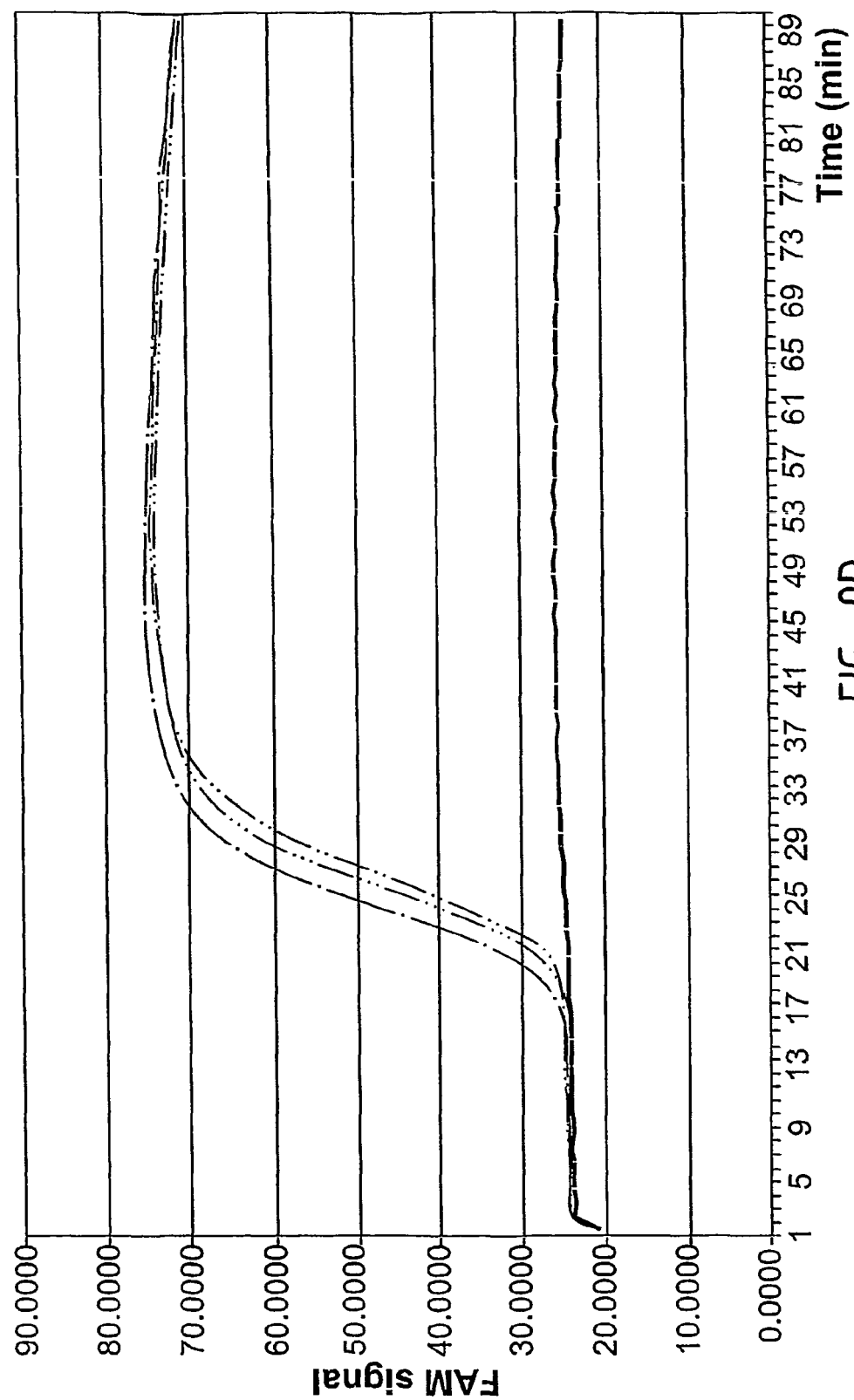
Figure 9E:
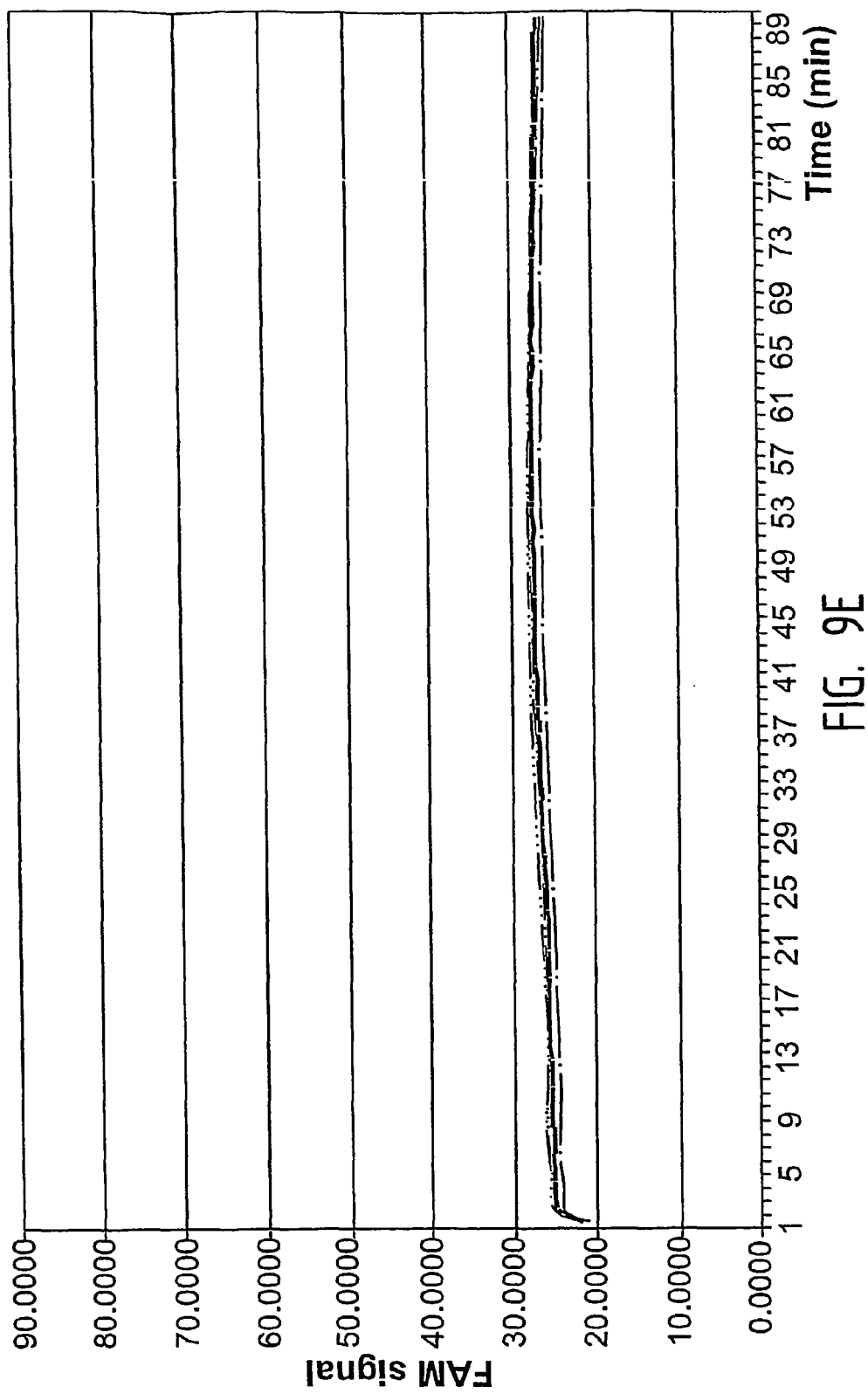
Figure 9F:
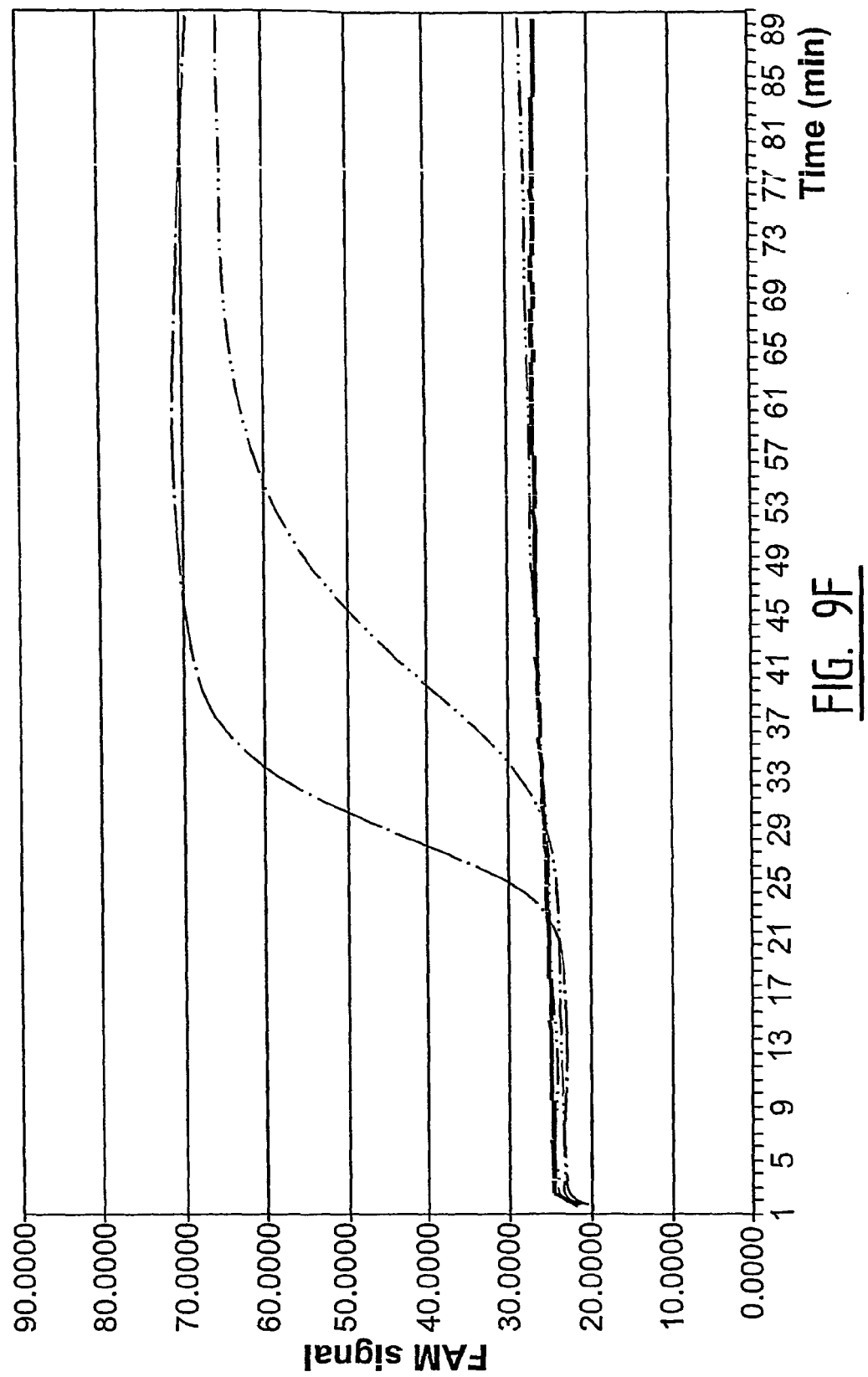
Figure 9G:
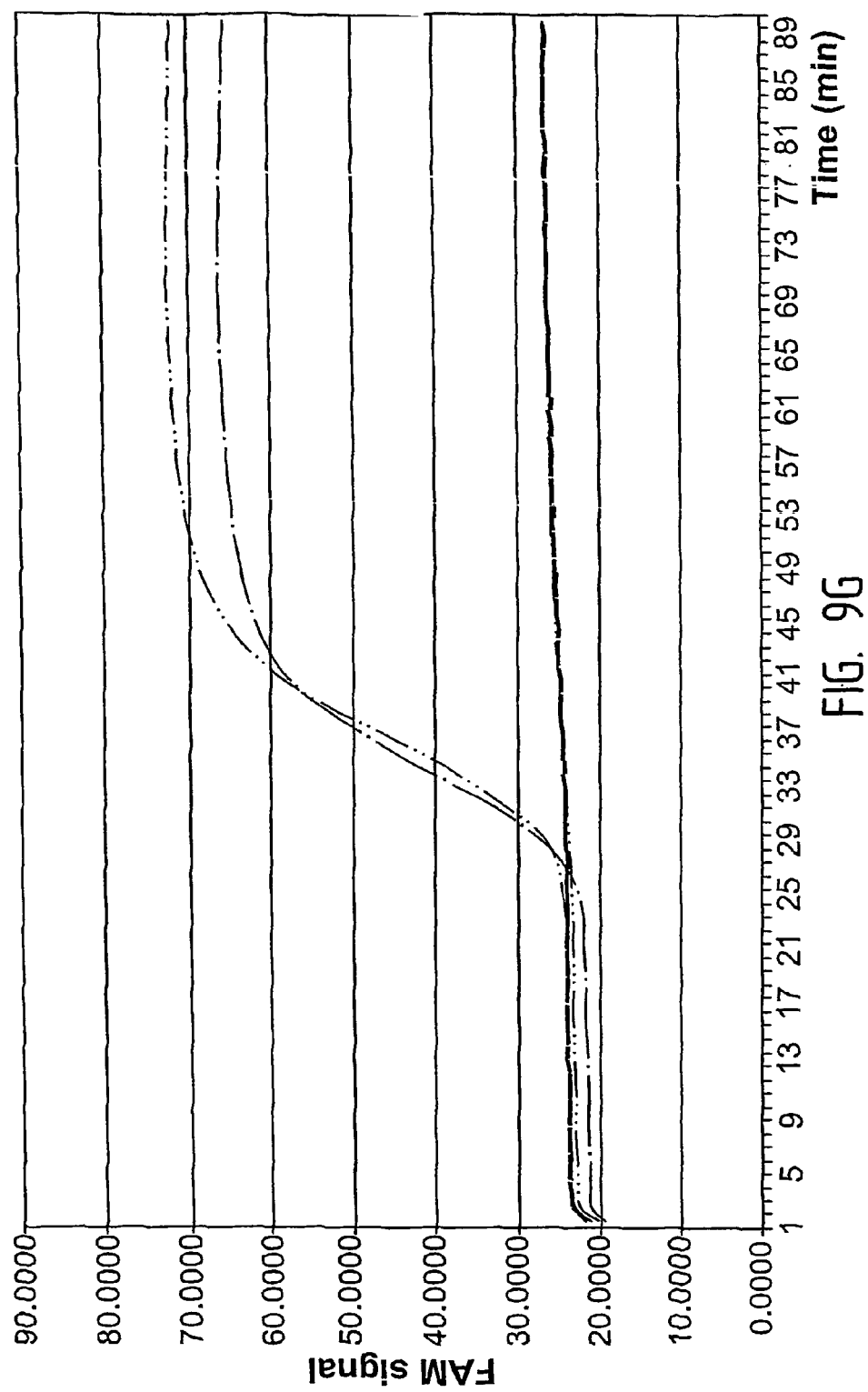
Figure 10A:
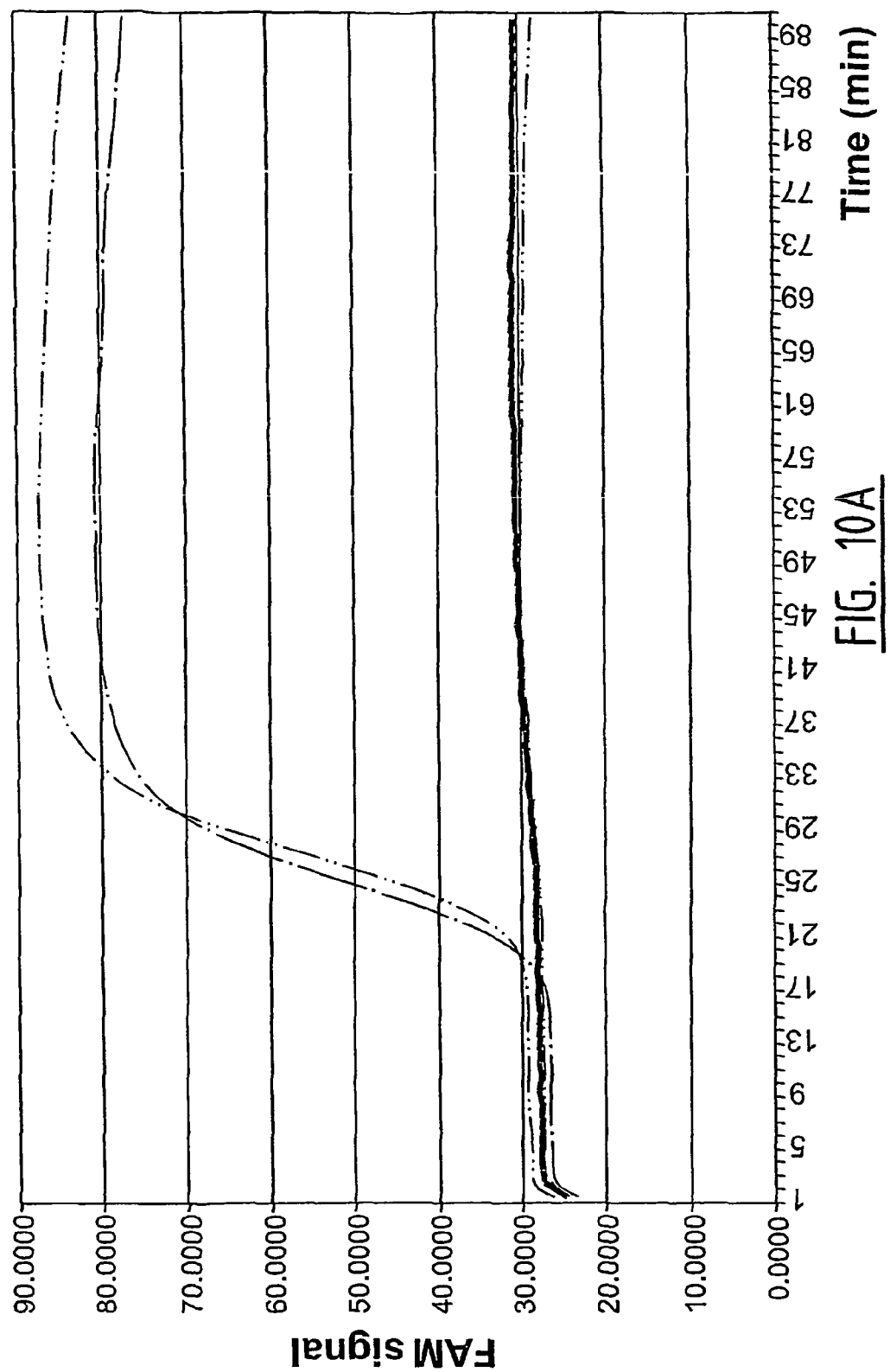
Figure 10B:
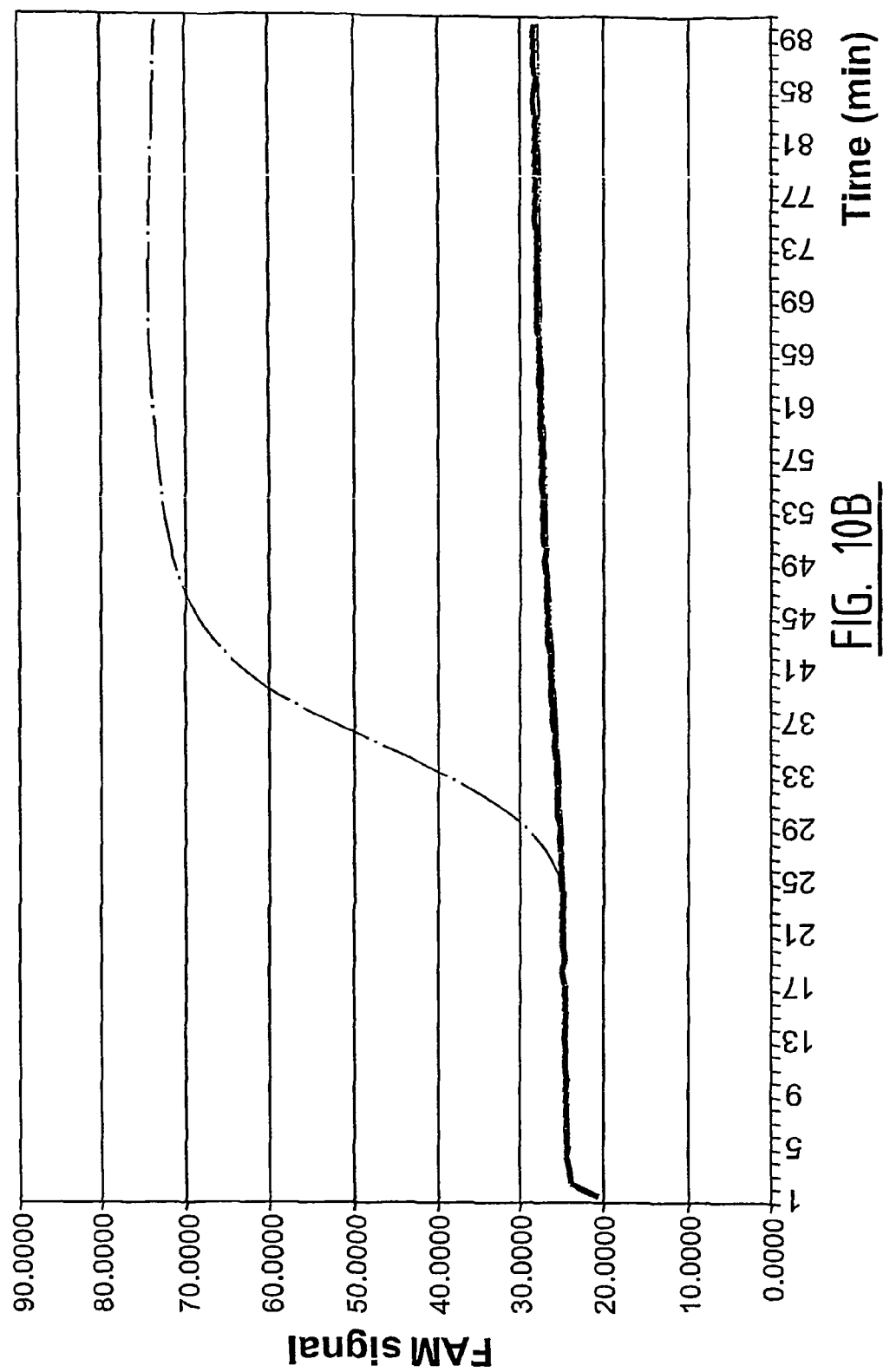
Figure 10C:
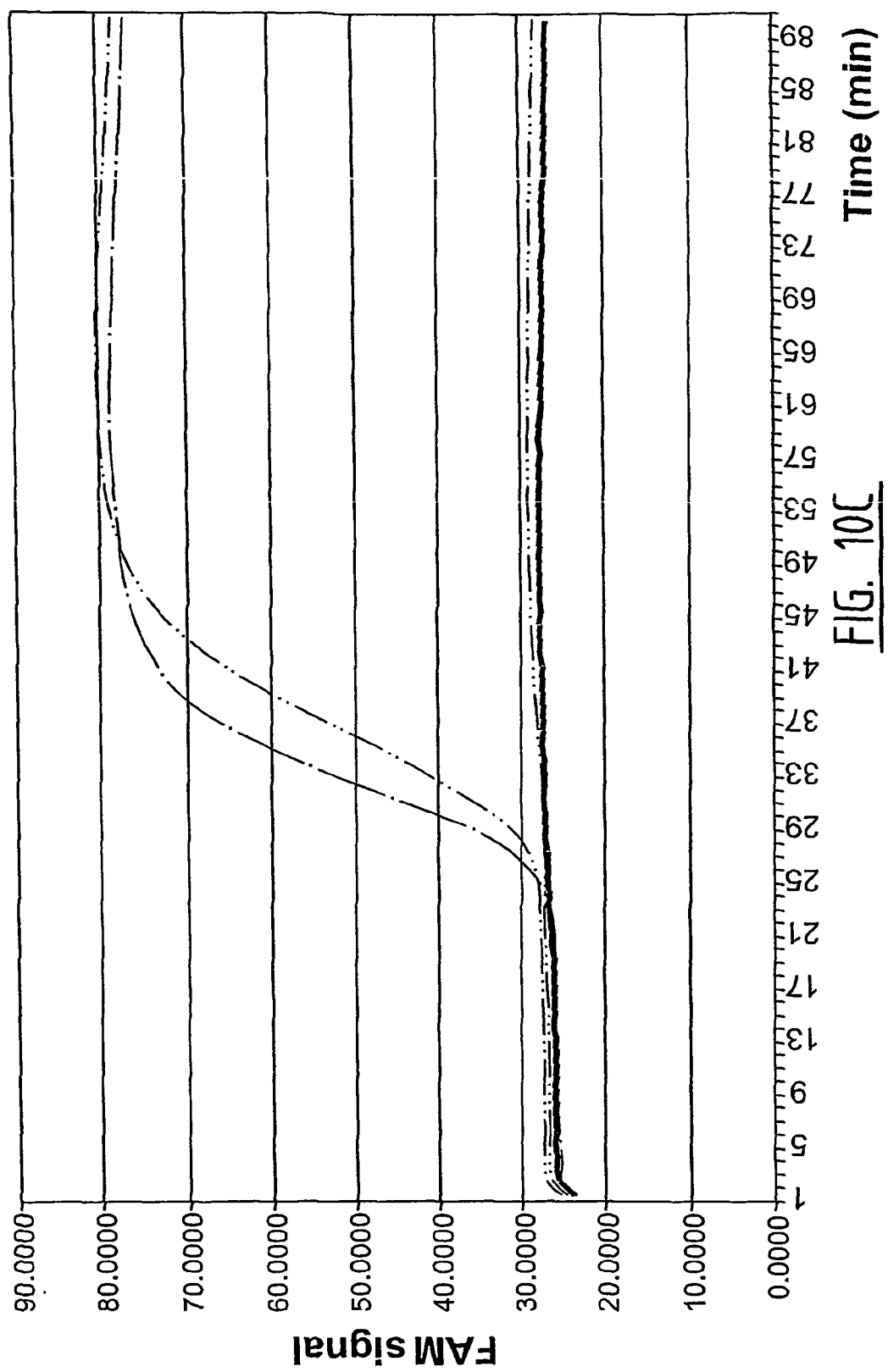
Figure 10D:
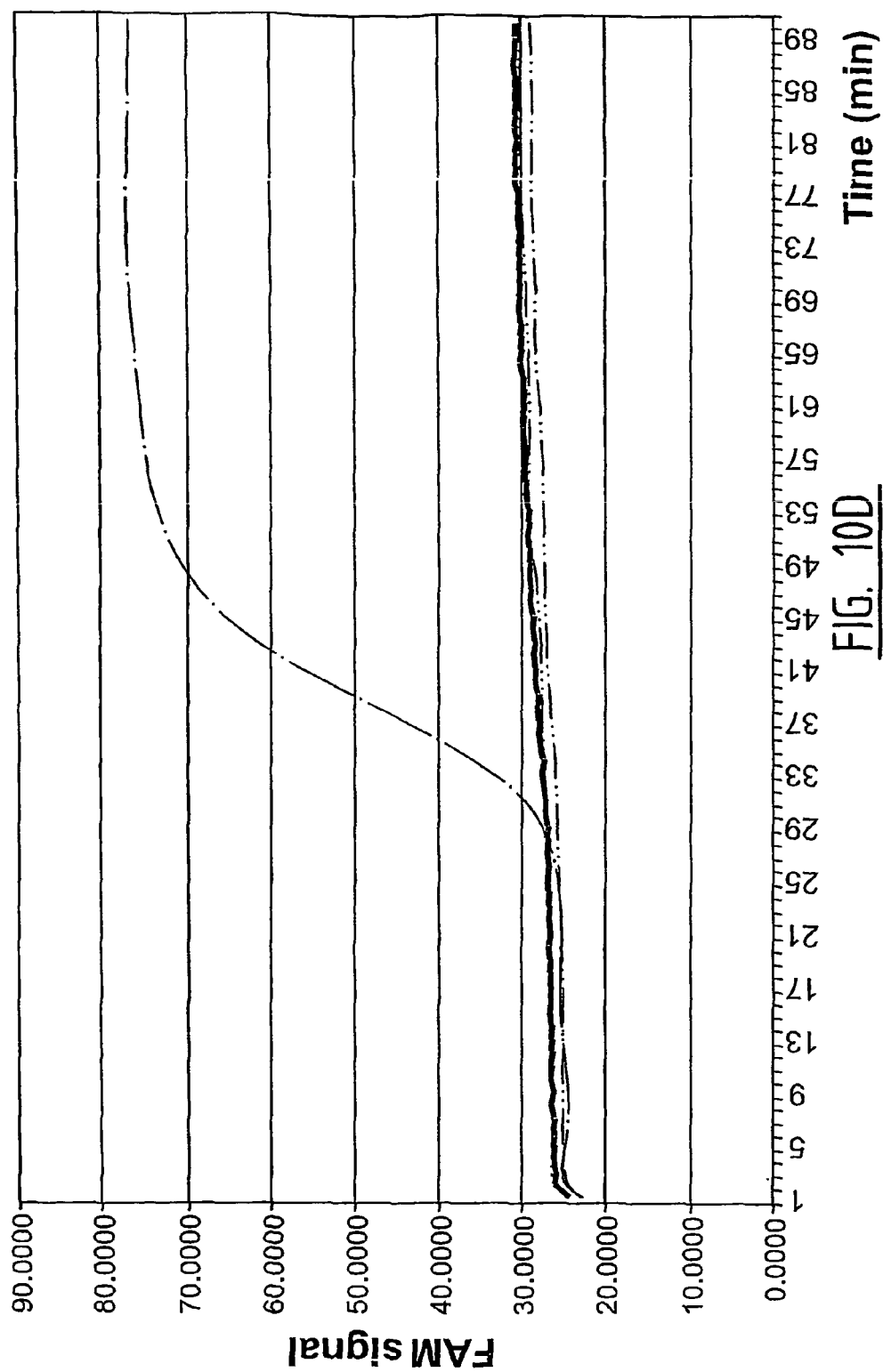
Figure 11A:
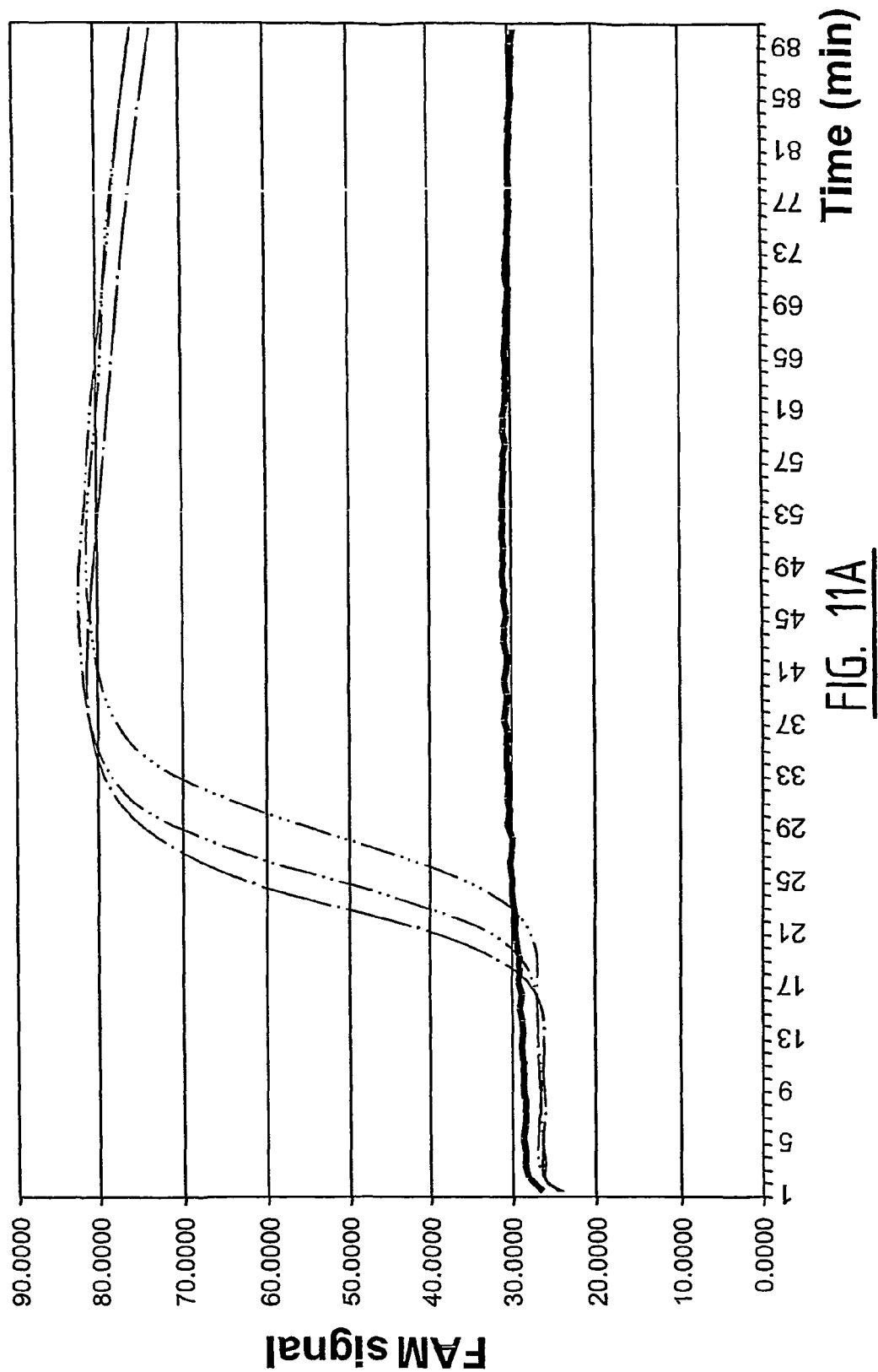
Figure 11B:
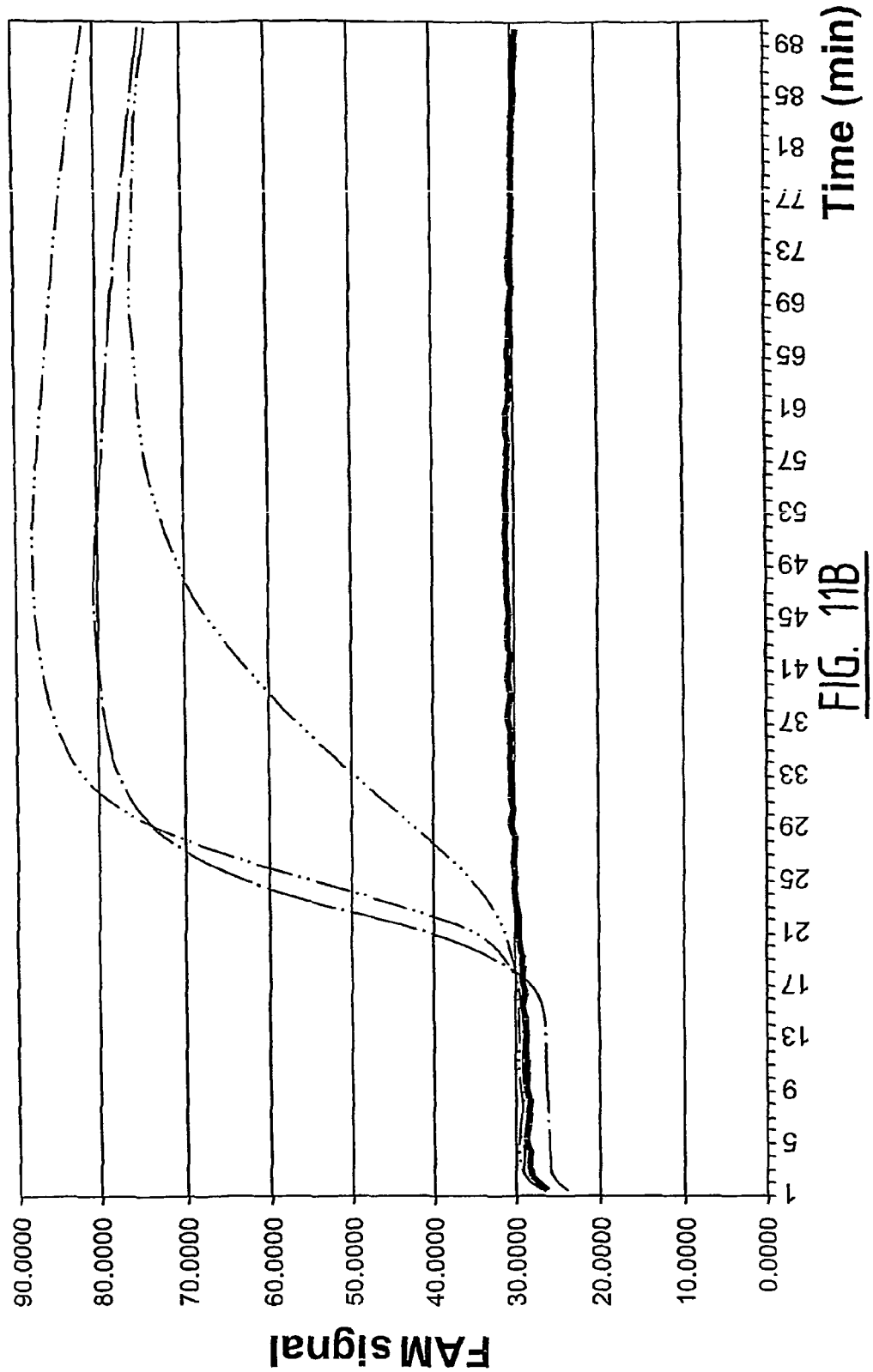
Figure 11C:
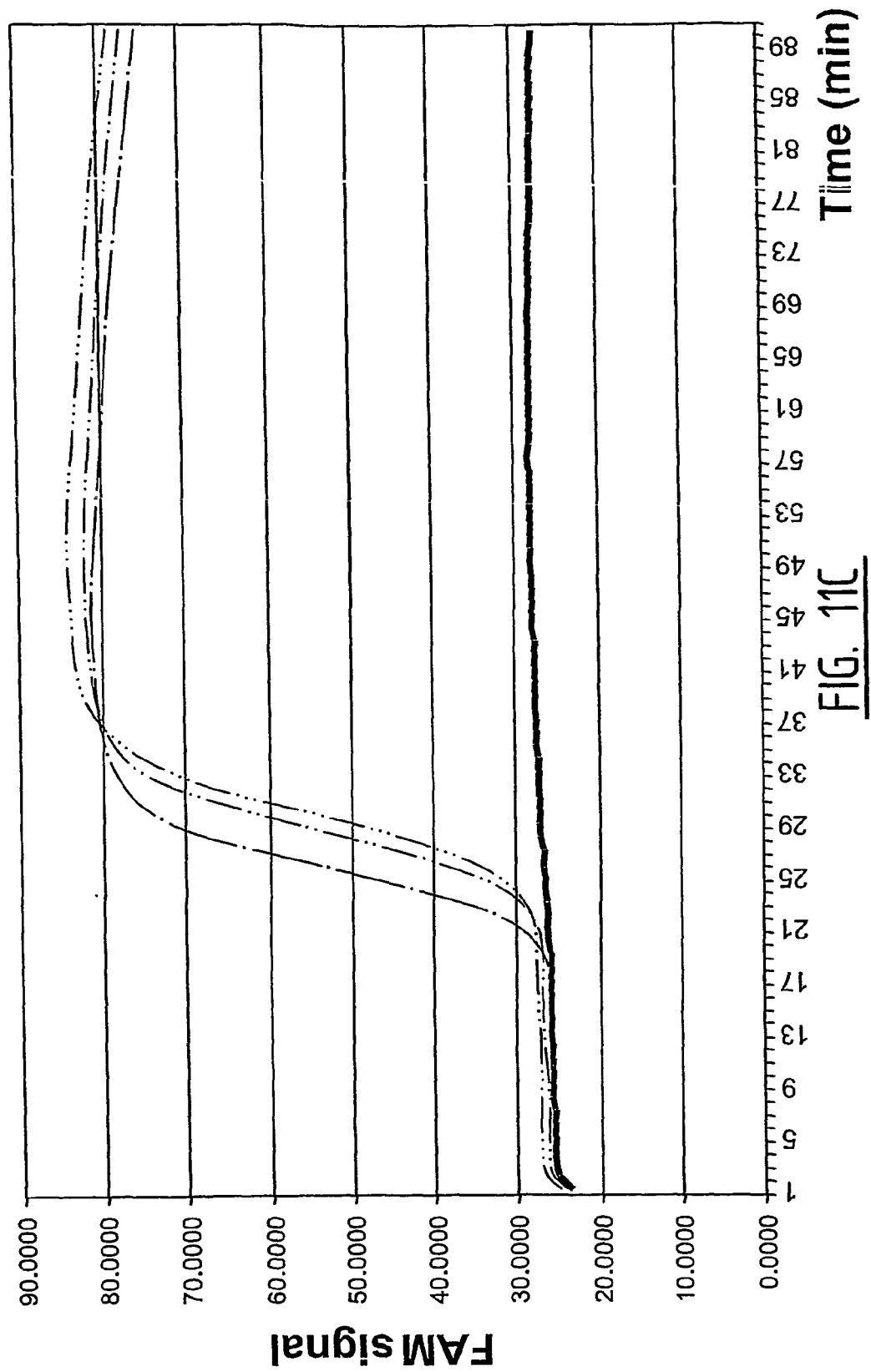
Figure 11D:
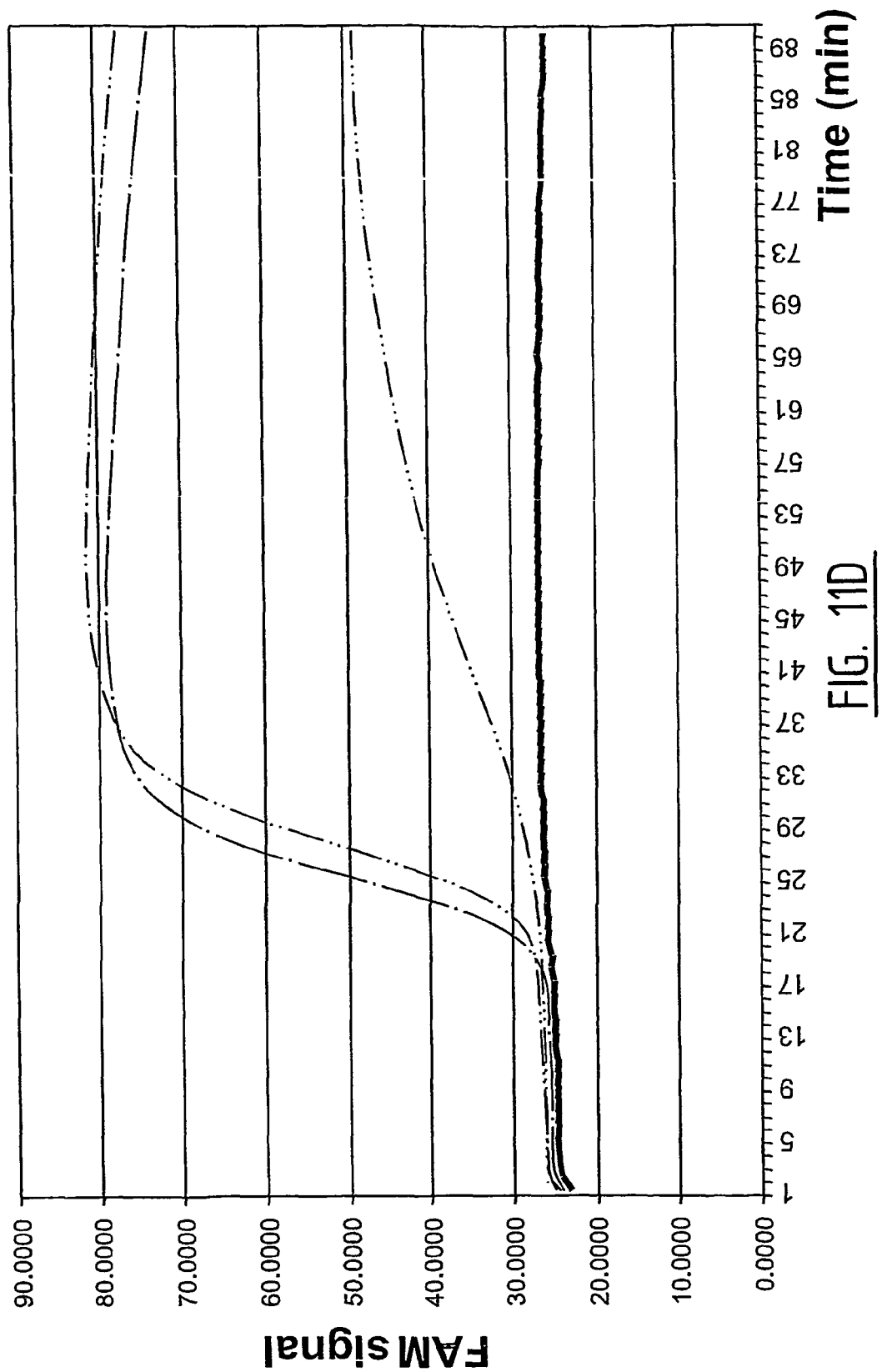
Figure 12A:
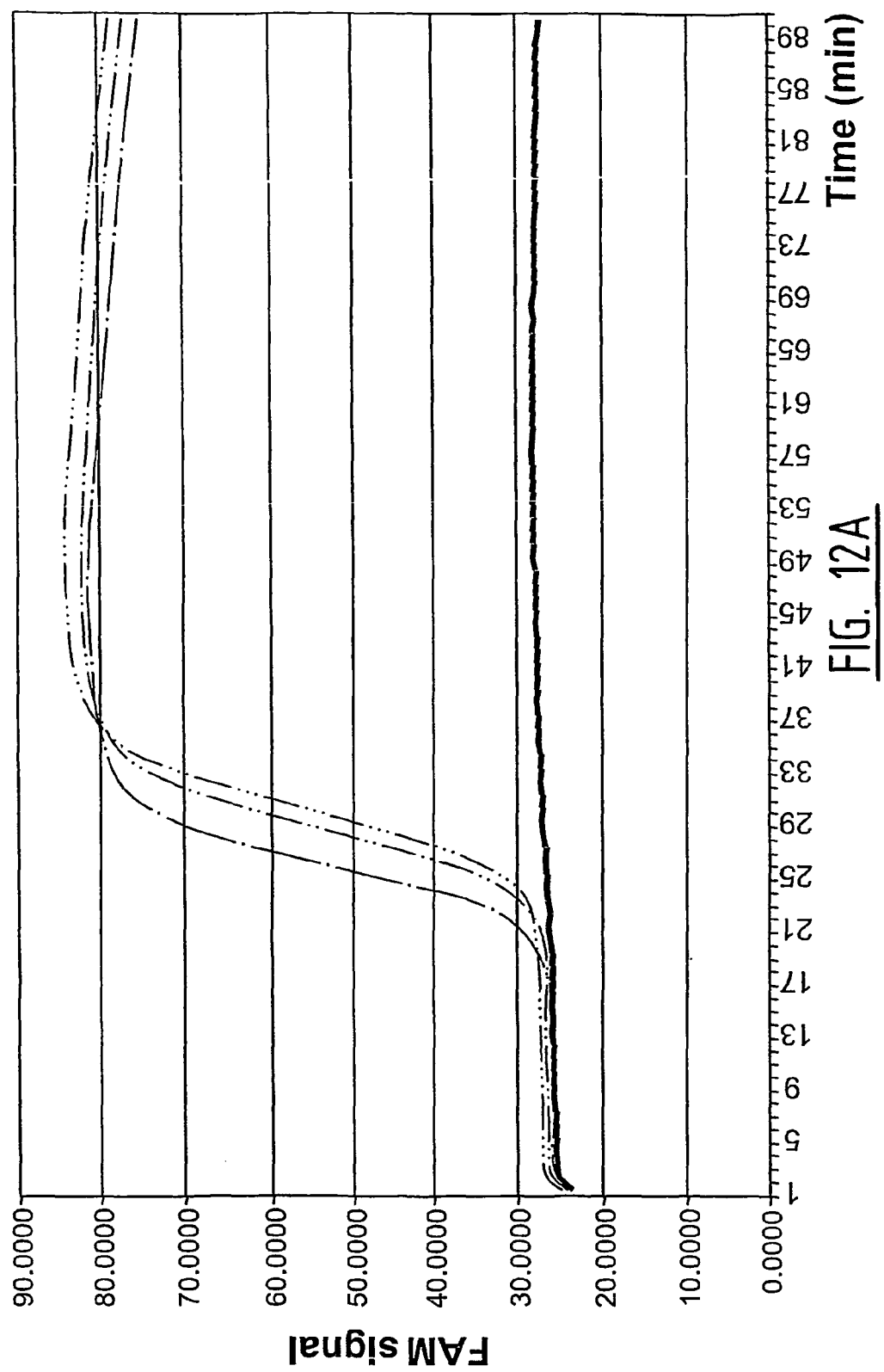
Figure 12B:
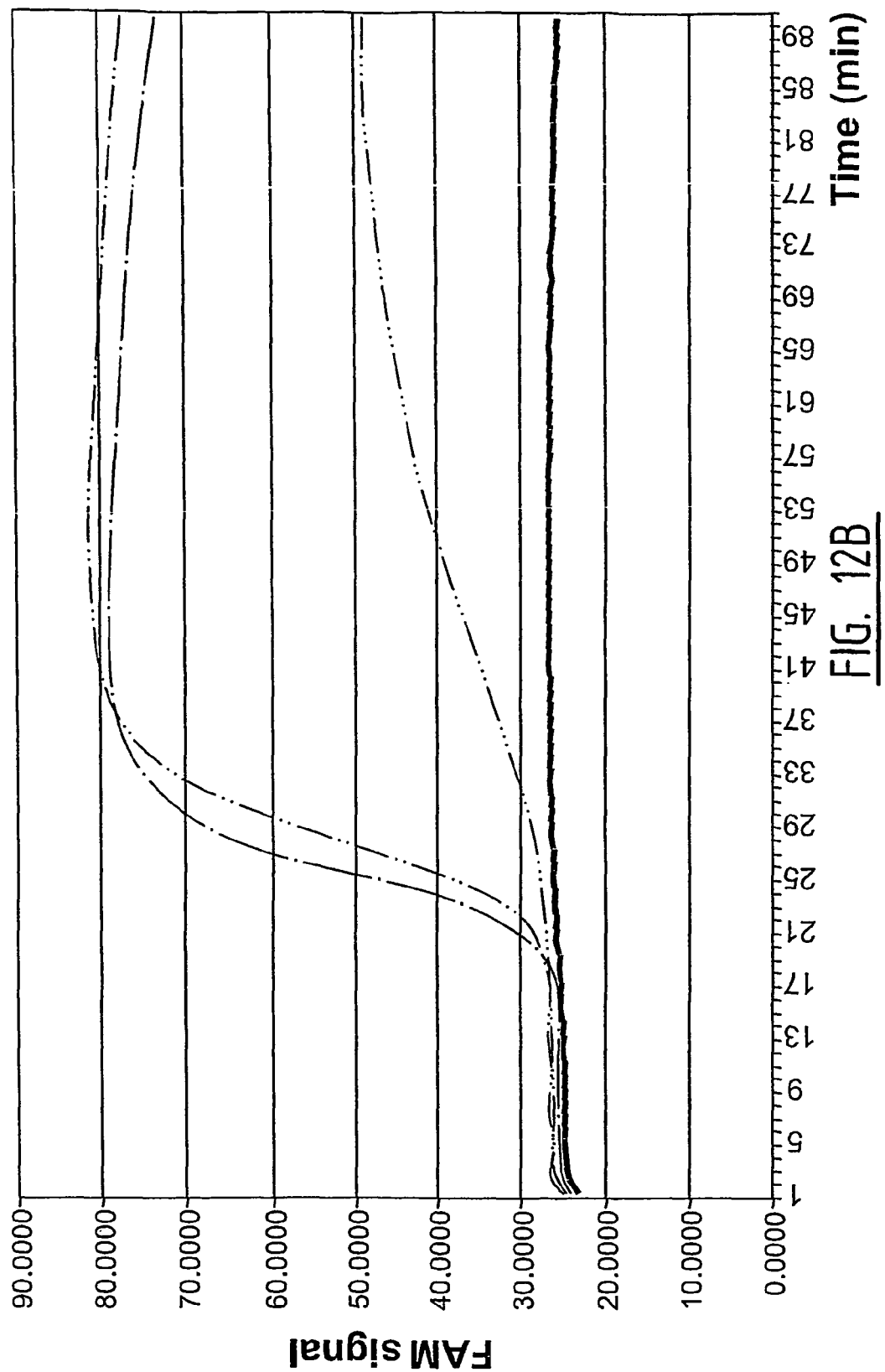
Figure 12C:
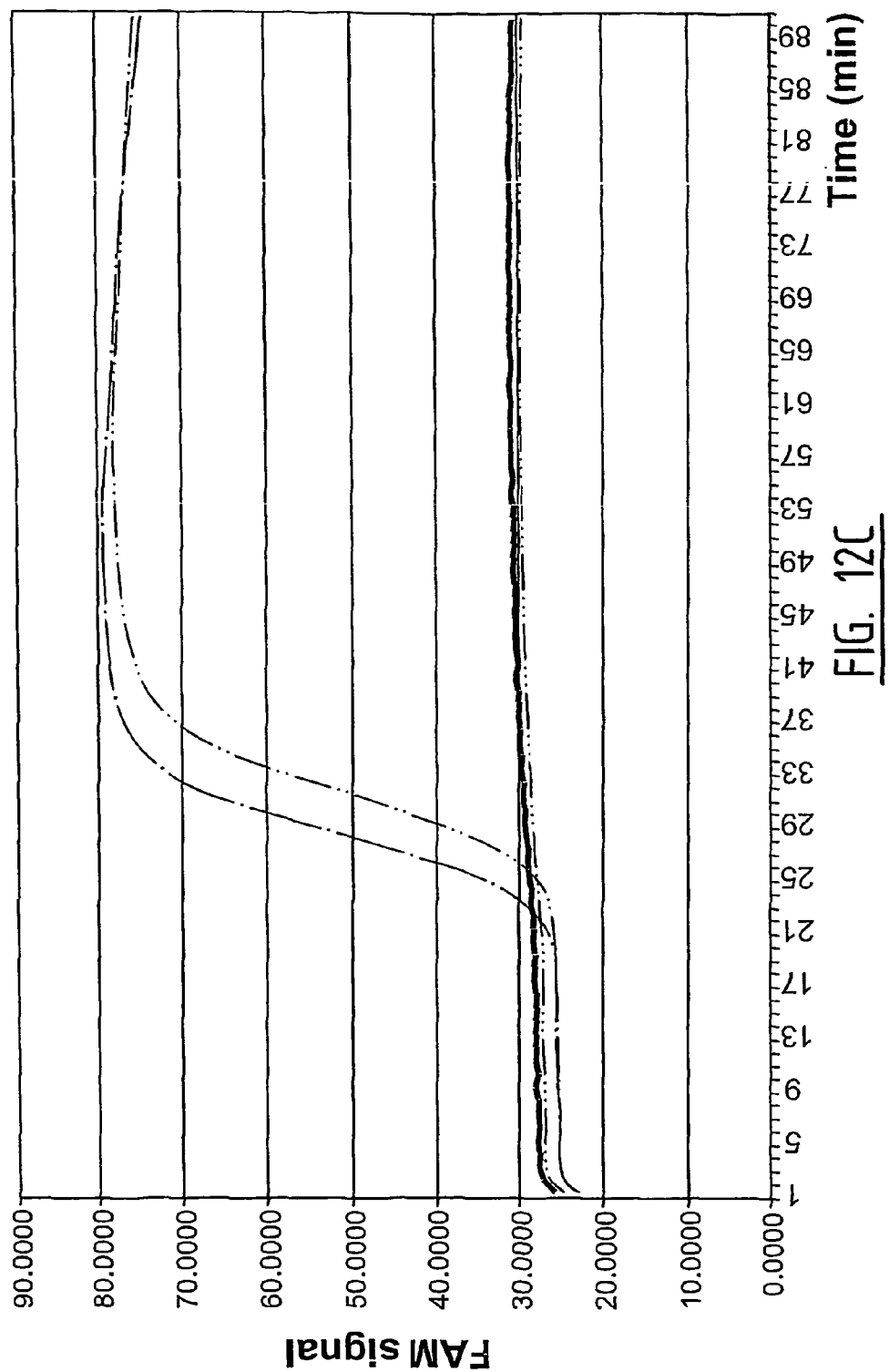
Figure 12D:
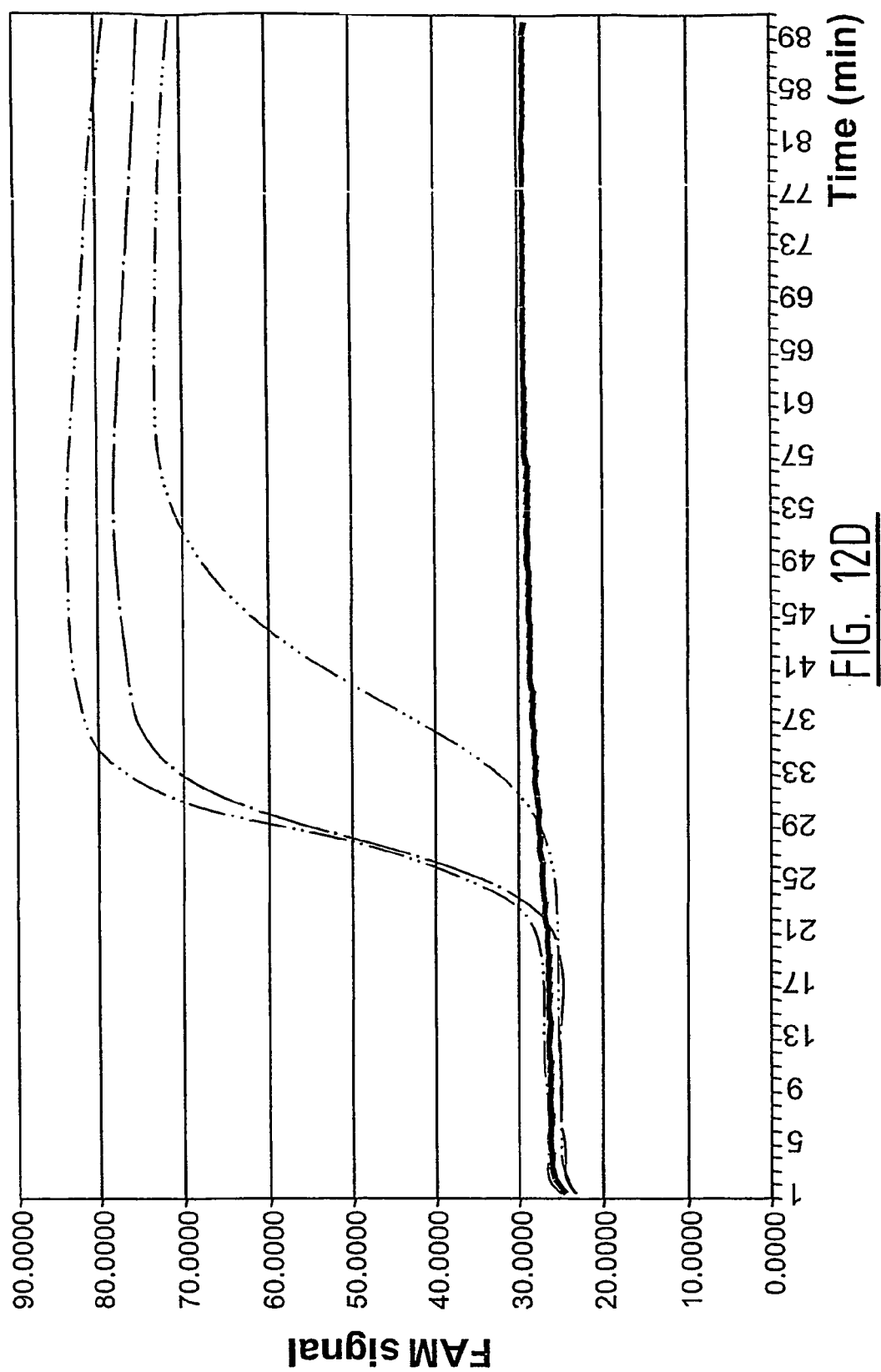
Figure 12E:
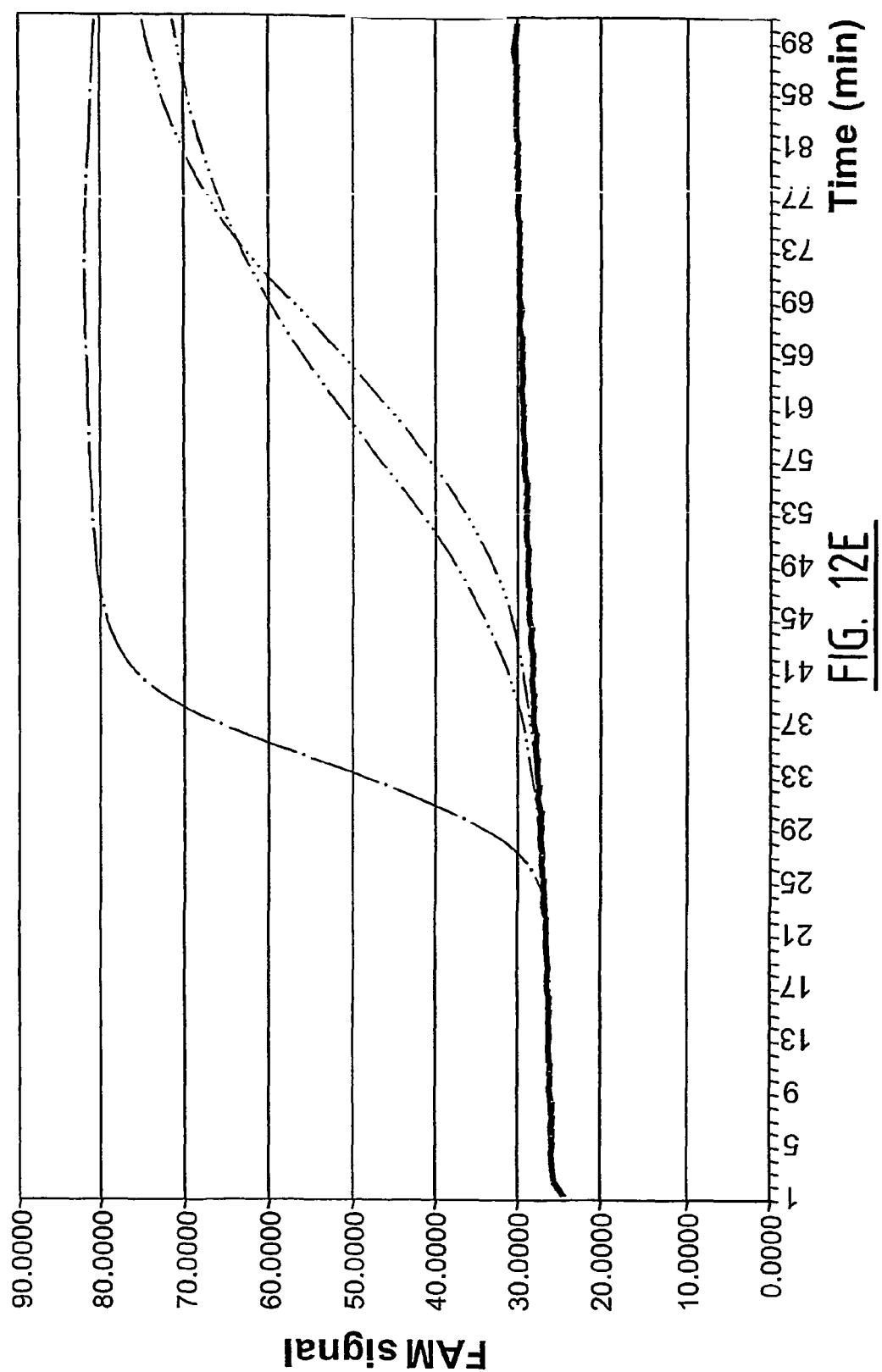
Figure 13A:
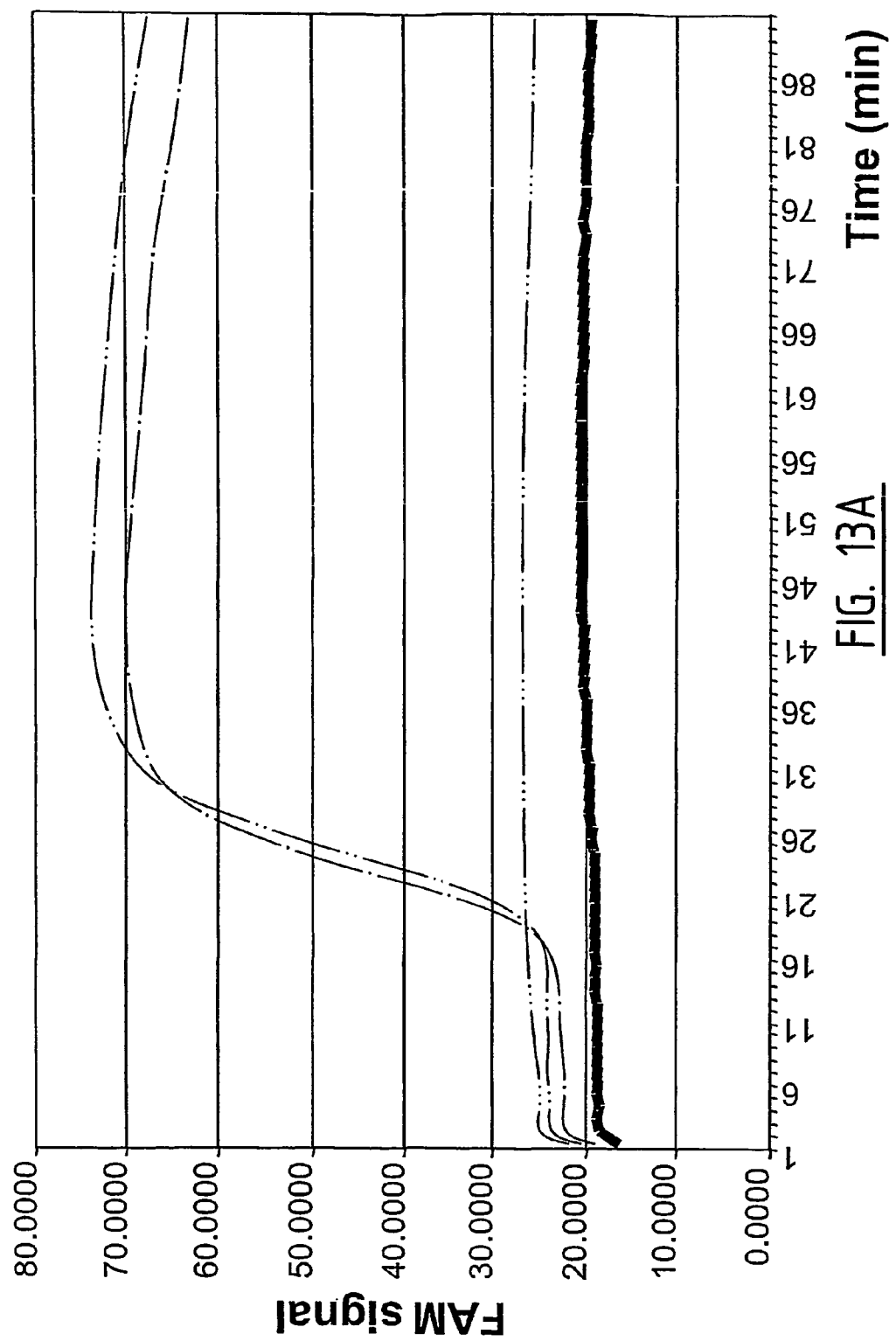
Figure 13B:
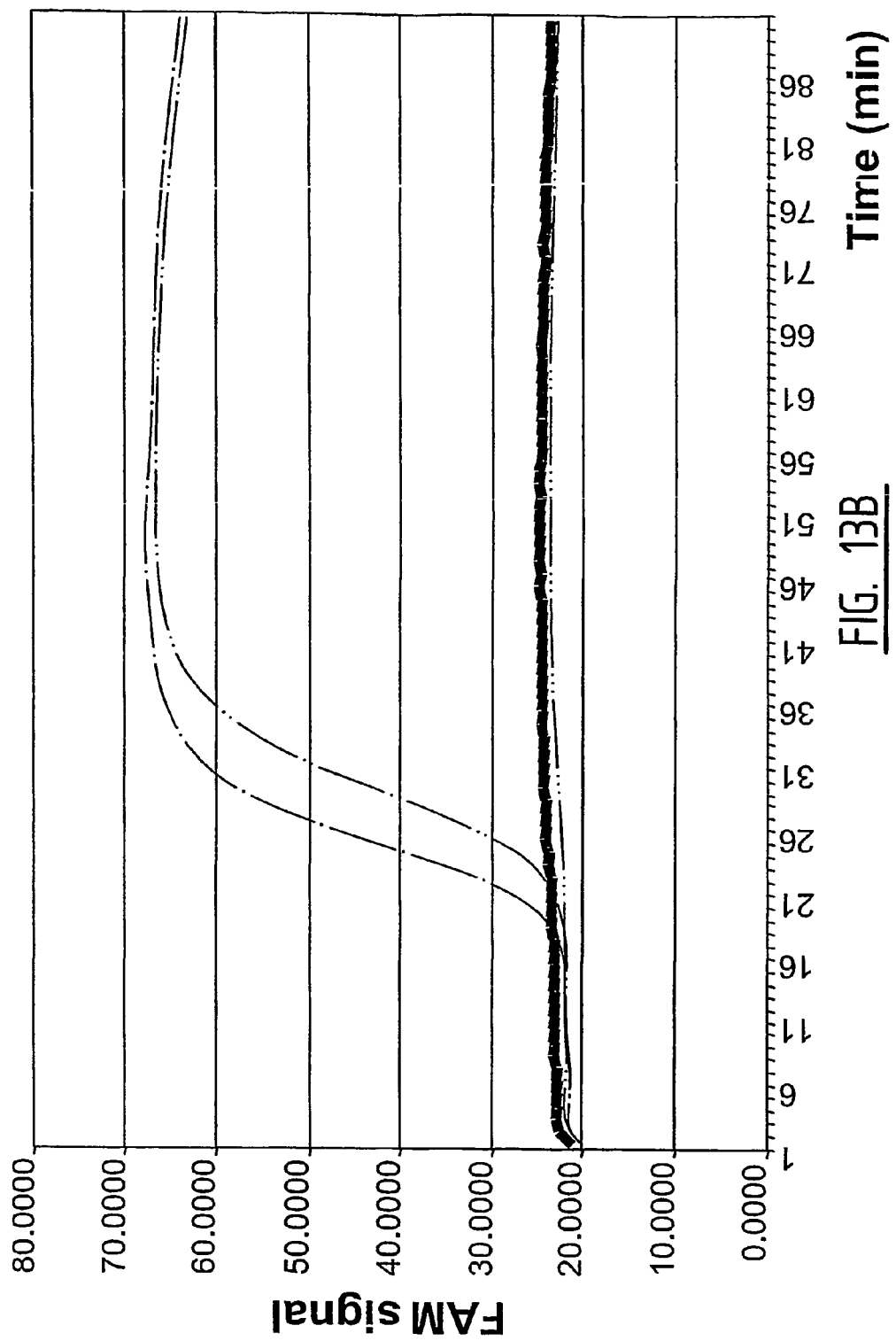
Figure 13C:
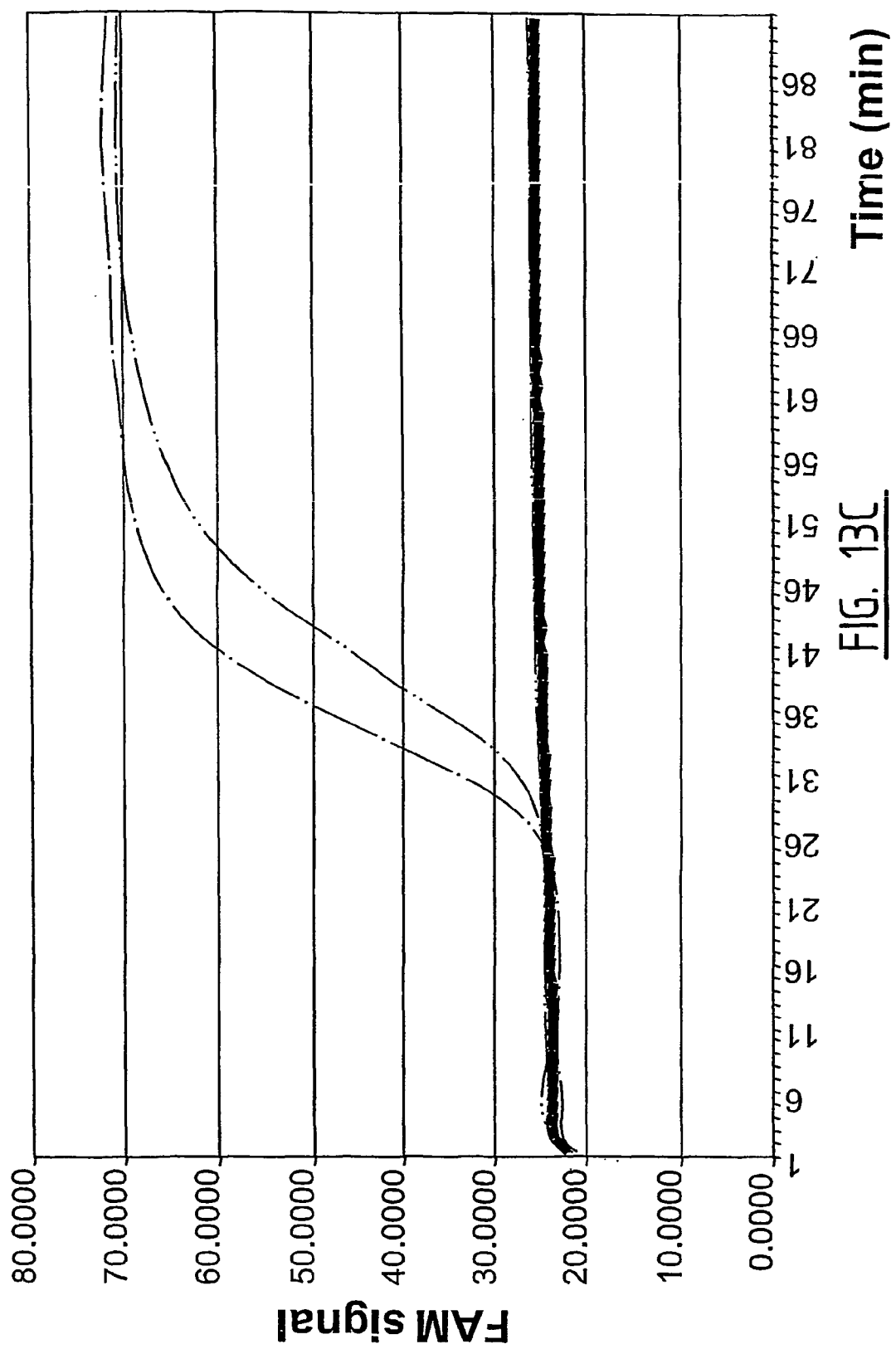
Figure 13D:
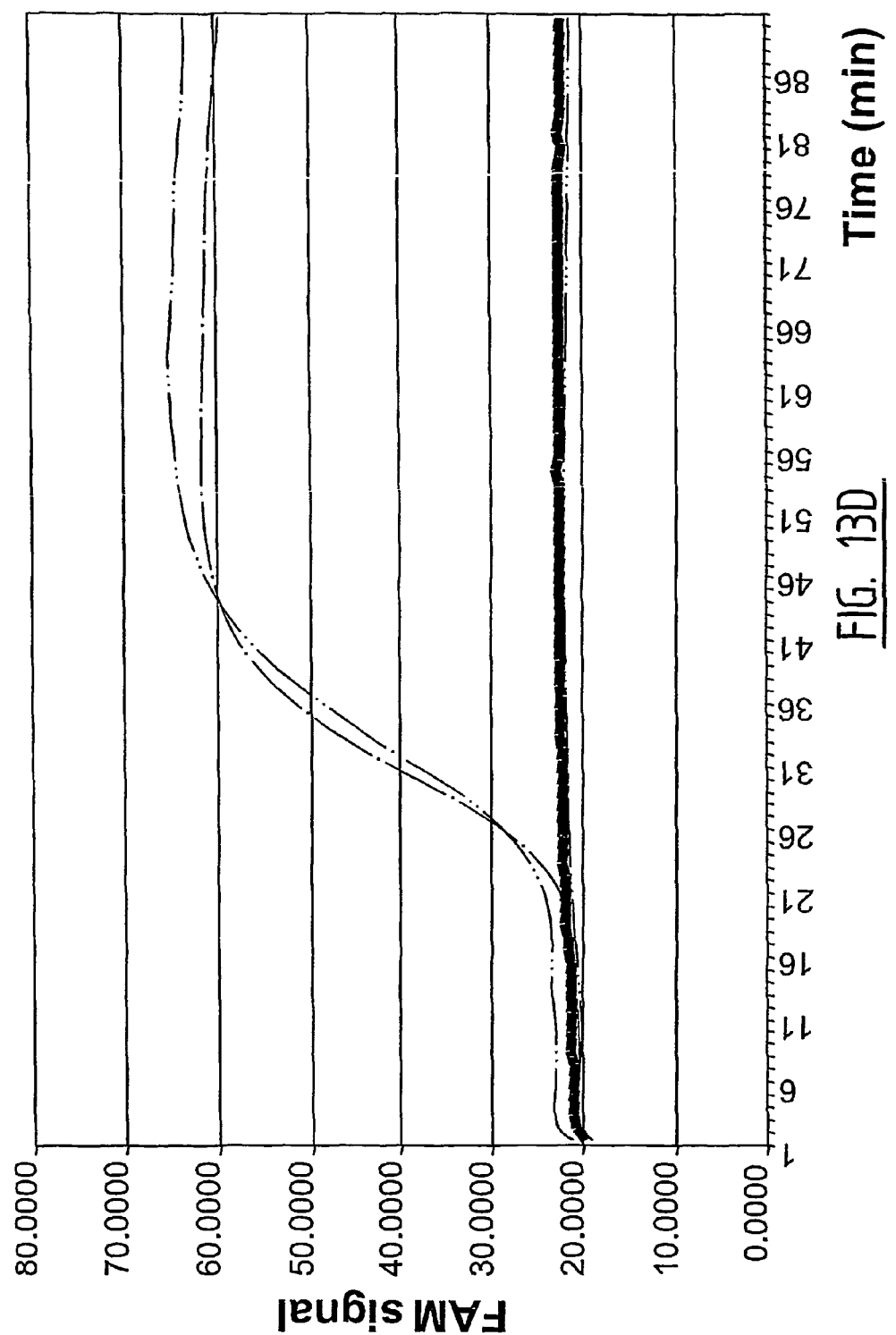

FIG. 6-8: Amplification of HIV RNA (Total viral RNA, 500, 50 and 5 cps) with anchor primers with different anchor lengths varyinq from 14 to 9 nucleotides (HIV17 (FIG. 6A), 20 (FIG. 7A), 21 (FIG. 8A), table 1) and the same primers containing anchors with 2'-O-Methyl nucleotides (HIV17 MET (FIG. 6B), HIV20 METa & b (FIG. 7B and C), HIV21 METa & b (FIG. 8B and C), table 1). All in combination with a standard p2 primer (HIV2) and a molecular beacon (HIV-MB-WT, table 1) as probe. A sample without template (NT) is used as negative control.

FIG. 9: Amplification of HIV RNA (Total viral RNA, 500, 50 and 5 cps) with a standard p1 primer (HIV11, table 1), anchor primers (HIV17 and HIV22, table 1) and p1 primers containing anchors with LNA nucleotides (HIV22 LNA1-4, table 1). All in combination with a standard p2 primer (HIV2, table 1) and a molecular beacon (HIV-MB-WT, table 1) as probe. A sample without template (NT) is used as negative control. FIG. 9A: standard P1 primer HIV11; FIG. 9B: anchor primer HIV22 LNA1; FIG. 9C: anchor primer HIV22 LNA2; FIG. 9D: anchor primer HIV17; FIG. 9E: anchor primer HIV22; FIG. 9F: anchor primer HIV22 LNA3; FIG. 9G: anchor primer HIV22 LNA4.

FIG. 10: Amplification of HIV RNA (Total viral RNA, 500, 50 and 5 cps) with anchor primers (FIG. 10A: HIV17 and FIG. 10C: HIV21, table 1) and p1 primers containing PNA anchors (FIG. 10B: HIV17 PNA and FIG. 10D: HIV21 PNA, table 1). All in combination with a standard p2 primer (HIV2, table 1) and a molecular beacon (HIV-MB-WT, table 1) as probe. A sample without template (NT) is used as negative control.

FIG. 11: Amplification of HIV RNA (Total viral RNA, 500, 50 and 5 cps) with standard p2 primers (HIV2 (FIG. 11A) and HIV26 (FIG. 11B), table 1) and anchor p2 primers (HIV27 (FIG. 1C) and HIV29 (FIG. 1D), table 1). All in combination with a standard p1 primer (HIV11, table 1) and a molecular beacon (HIV-MB-WT, table 1) as probe. A sample without template (NT) is used as negative control.

FIG. 12: Amplification of HIV RNA (Total viral RNA, 500, 50 and 5 cps) with anchor p2 primers with different anchor lengths varying from 22 to 14 nucleotides (HIV27 (FIG. 12A), 31 (FIG. 12C), 32 (FIG. 12D), 33 (FIG. 12E), 29 (FIG. 12B), table 1). All in combination with a standard p1 primer (HIV11, table 1) and a molecular beacon (HIV-MB-WT, table 1) as probe. A sample without template (NT) is used as negative control.

FIG. 13: Amplification of HIV RNA (Total viral RNA, 500, 50 and 5 cps) with an anchor p1 primer (HIV17, table 1) in combination with a standard p2 primer (HIV2, table 1) (FIG. 13B or anchor p2 primers (HIV27 (FIG. 13C) and HIV29 (FIG. 13D), table 1). The standard primer set (HIV1/HIV2, table 1) is used as a reference (FIG. 13A). All in combination with a molecular beacon (HIV-MB-WT, table 1) as probe. A sample without template (NT) is used as negative control.

Figure 14A:
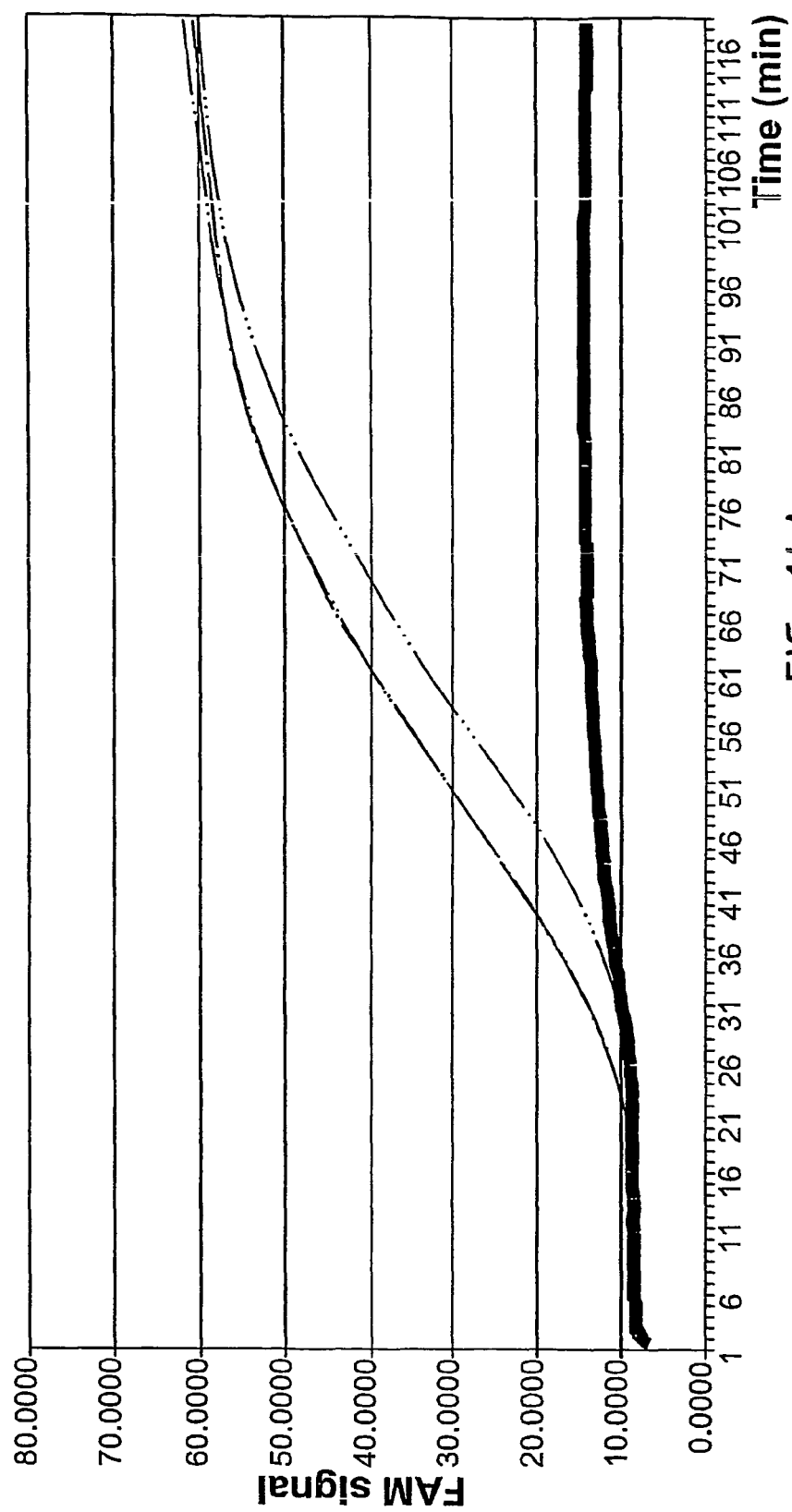
Figure 14B:
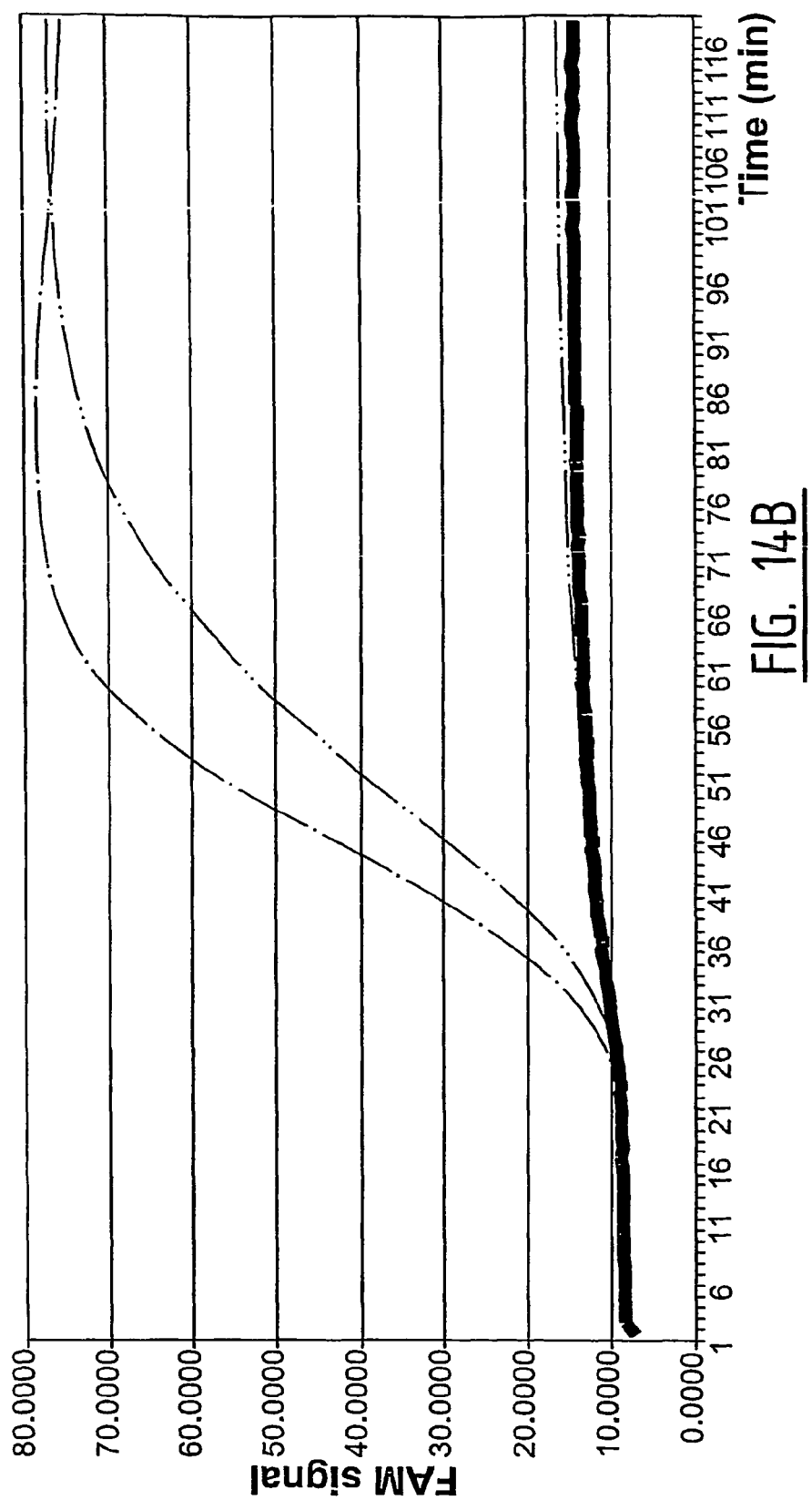
Figure 14C:
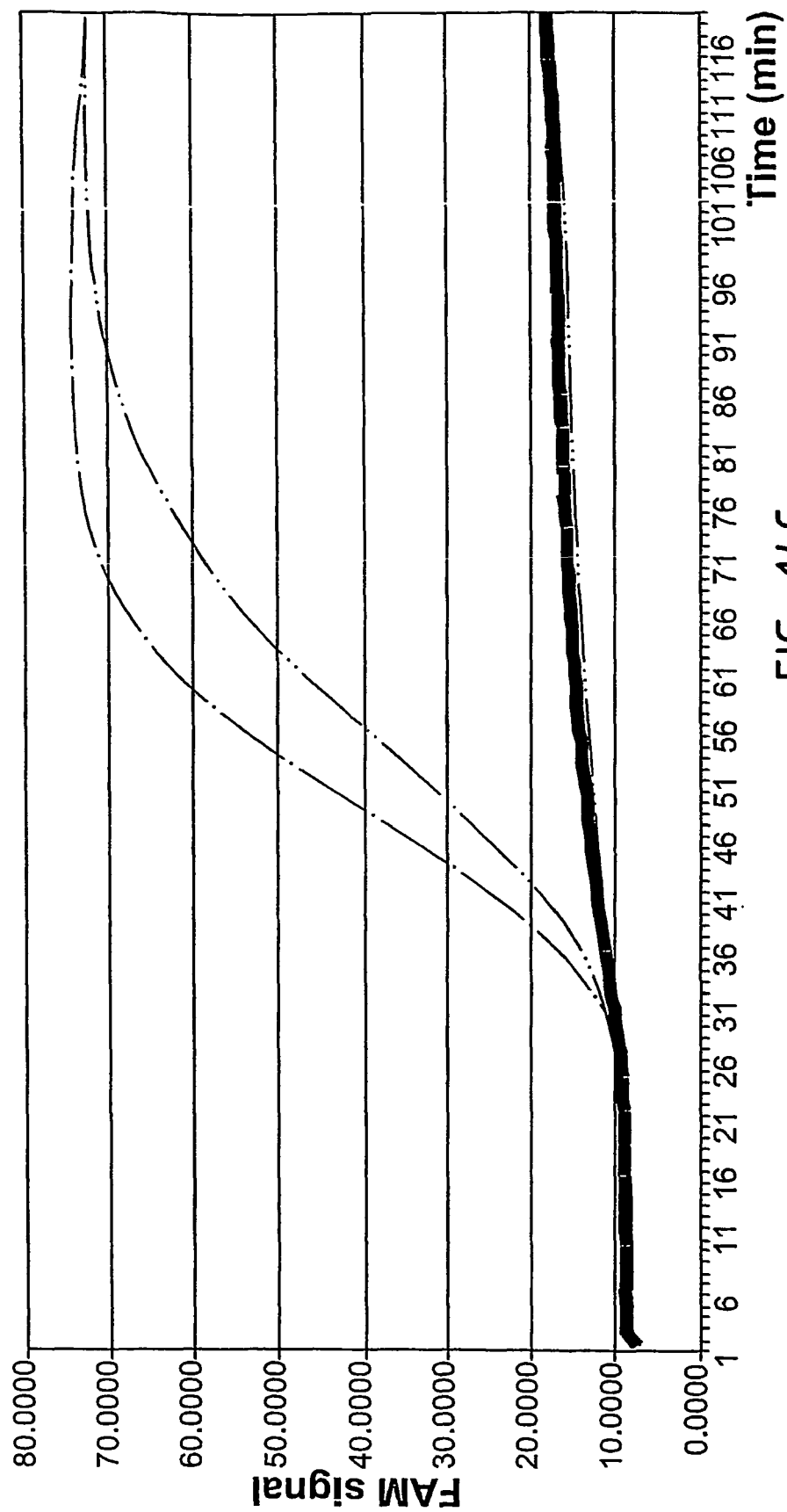

FIG. 14: Amplification of HCV RNA (RNA transcript, 5×10⁵, 5×10⁴ and 5×10³ cps) with an anchor p1 primer (HCV13 (FIG. 14B) or HCV 46 (FIG. 14C), table 2) or a standard p1 primer (HCV1 (FIG. 14A), table 2), both in combination with a standard p2 primer (HCV2, table 2) and a molecular beacon (HCV-WT3, table 2) as probe. A sample without template (NT) is used as negative control.

Figure 15A:
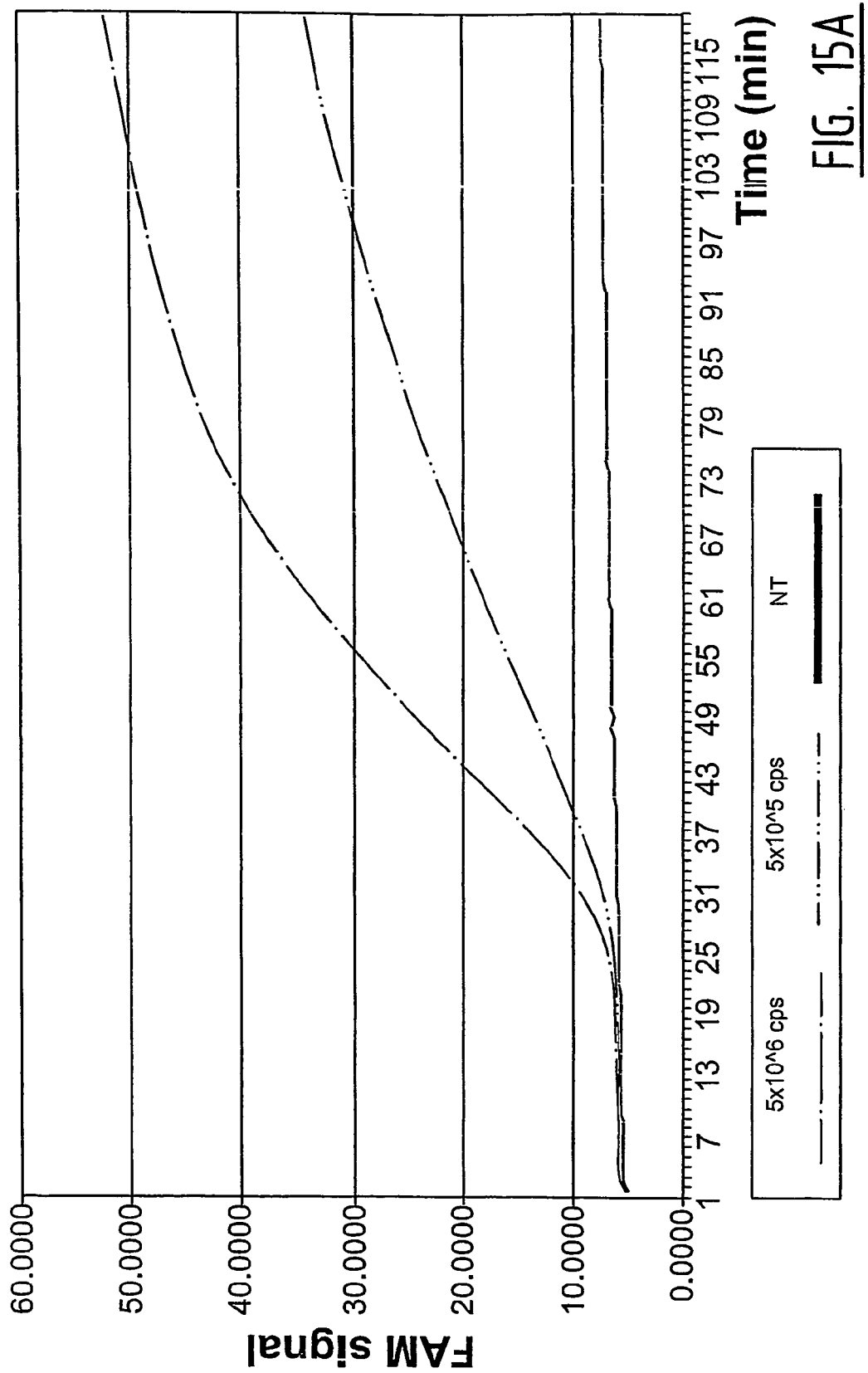
Figure 15B:
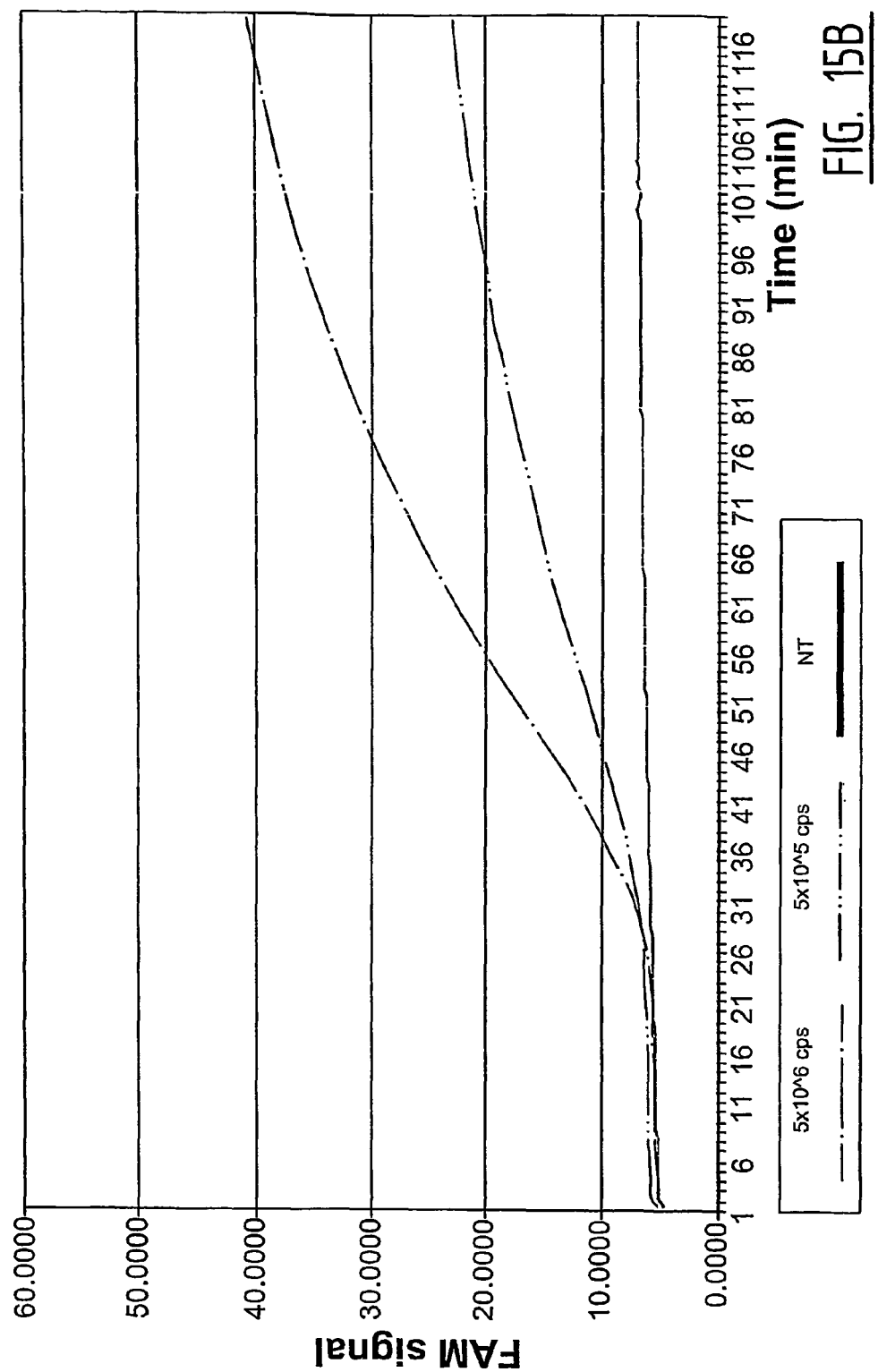

FIG. 15: Amplification of HCV RNA (RNA transcript, 5×10⁶ and 5×10⁵ cps) with an anchor p1 primer (HCV22 (FIG. 15B), table 2), having a 3 nt gap between the anchor sequence and the 3' hybridizing sequence. Anchor p1 primer HCV13 (FIG. 14A)(table 2) is used as reference. Both anchored primers are combined with the standard p2 primer (HCV2, table 2) and molecular beacon (HCV-WT3, table 2). A sample without template (NT) is used as negative control.

FIG. 16: Scheme showing a preferred embodiment of the method according to the invention. P1: first primer; Y; transcription enhancing sequence; T7: T7 promotor sequence, H: hybridizing sequence; P2: second primer; X: amplification enhancing sequence; H: hybridizing sequence.

EXAMPLES

Example 1

Amplification of HIV RNA with Anchor p1 Primer

Scott Layne HIV particles (HIV-infected cells (Layne et al (1992), Virology 189: 695-714) lysed with lysisbuffer (NucliSens, BioMérieux)) or HIV gag RNA transcript were used as input material for amplification. Inputs of 500, 50 and 5 cps were tested. Amplification was performed in NASBA buffer (40 mM Tris-HCl pH 8.5, 12 mM MgCl$_2$, 70 mM KCl, 15% v/v DMSO, 5 mM DTT, 1 mM each DNTP, 2 mM ATP, 2 mM CTP, 2 mM UTP, 1.5 mM GTP, 0.5 mM ITP, 0.2 μM of each primer (forward primer (P1) and reverse primer (P2), table 1), 0.1 μM molecular beacon probe (HIV-MB-WT, table 1). The mixture was incubated for 2 min at 65° C. to denature the RNA and for 2 min at 41° C., to hybridize the P1 primer to the target. Subsequently, NASBA enzymes (0.08 units RNase H, 32 units T7 RNA polymerase, 6.4 units AMV reverse transcriptase and 2.1 μg BSA) were added, the reaction mixture was mixed by gently tapping and short centrifugation, and the amplification and real-time detection was started. The reaction mixture was incubated at 41° C. in the NucliSens EasyQ Analyzer (NucliSens, BioMérieux) for 60 minutes with fluorescence monitoring every minute. The reactions were excited at 485 nm and the emission signal was measured at 518 nm.

Amplification with an anchor p1 primer (HIV12, table 1) was performed in combination with a standard p2 primer (HIV2, table 1). The anchor primers consist of a 22 nt anchor sequence upstream of the T7-promoter sequence and 7 nt hybridizing sequence downstream of the T7-promoter sequence. Amplification with standard p1 primer (HIV11, table 1) and standard p2 primer (HIV2, table 1) was used as reference. The results show that sensitivity of amplification with the anchor primer is comparable to the reference primer (FIG. 2).

Example 2

Amplification of HIV RNA with p1 Primer with Very Short Hybridisation Sequence

Amplification with a p1 primer identical to HIV12, but no anchor sequence (HIV11, table 1, FIG. 3), containing only the 3' hybridizing target specific sequence of 7 nucleotides, was performed in combination with a standard p2 primer (HIV2, table 1). HIV11 and HIV12 (table 1) were used as reference. Amplification was performed as described in example 1. As shown in FIG. 4, no amplification was observed with primer HIV11 (FIG. 4B), indicating that the anchor sequence is required for efficient amplification. The anchor is assumed to be necessary during the initiation of the reaction and not in the cyclic phase. Therefore, addition of a non-anchored primer can be of advantage during the cyclic phase of the reaction. When using both the anchor primer HIV12 and primer HIV11 in one and the same amplification reaction, a slight improvement of the reaction kinetics was observed (FIG. 4D).

Example 3

Amplification of HIV RNA with Anchor p1 Primers with Different Anchor Lengths

To investigate what minimum length of the anchor, still results in a specific amplification, primers with different anchor lengths were designed. Amplification with anchor primers with different anchor lengths (deleted from the 5'end) varying from 22 to 7 nucleotides (HIV12, 15, 16, 17, 20, 21, 22, table 1) was performed in combination with a standard p2 primer (HIV2, table 1). The standard p1 primer HIV1 (table 1) was used as reference. Amplification was performed as described in example 1. Deletion up to 14 nucleotides still results in an efficient amplification as compared to the references (HIV1 standard primer and HIV12 anchor primer) (FIG. 5). However, anchor lengths below 14 nucleotides show very little or no amplification. The hybridization temperature of 14 nucleotides or more is expected to be higher then 41° C. (amplification temperature). Shorter anchors could have hybridization temperatures below 41° C., which may explain inefficient amplification.

Example 4

Amplification of HIV RNA with Anchor p1 Primers Using 2'-O-Methyl Modified Nucleotides in Anchor Sequence In order to increase the binding efficiency of the anchor, 2'-O-Methyl modified nucleotides are incorporated in the anchor. Primers with anchor lengths of 14 nt (HIV17 MET, table 1), 12 nt (HIV20 METa & b, table 1), 9 nt (HIV21 METa & b, table 1) and 7 nt (HIV22 METa & b) were used in amplification. The expected melting temperature increase is about 1.5° C. per incorporated 2'-O-Methyl modified nucleotide. A standard p2 primer (HIV2, table 1) was used as reverse primer. Amplification was performed as described in example 1. Using these anchor primers with 2'-O-Methyl modified nucleotides clearly improves the sensitivity of the amplification reaction (FIGS. 6-8), in particular when using anchors shorter then 14 nucleotides. (12 & 9 nt anchors HIV20 MET and HIV21 MET). 7 nt anchor primers with 2'-O-Methyl modified nucleotides (HIV22 MET) turn out to be too short (result not shown). Probably, 7 nucleotide anchors, even with 2'-O-Methyl modified nucleotides, have hybridization temperatures below 41° C., explaining inefficient amplification.

Example 5

Amplification of HIV RNA with Anchor p1 Primers Using LNA (Locked Nucleic Acid) Nucleotides in Anchor Sequence In order to increase the binding efficiency of the anchor, LNA nucleotides are incorporated in the anchor. The expected Tm increase is about 3-8° C. per incorporated LNA nucleotide. Four different anchor p1 primers with anchor lengths of 7 nt (HIV22 LNA 1 t/m4, table 1) were used in amplification. All these anchor p1 primers were tested in combination with a standard p2 primer. Amplification was performed as described in example 1. Compared to the 7 nt DNA anchor primer HIV22, LNA anchor primers clearly results in an improved sensitivity of amplification (table 1) (FIG. 9). Compared to the 14 nt anchor primer HIV17 (table 1) or the standard p1 primer HIV1 (table 1), the performance of these LNA anchor primers is less. The position of the LNA nucleotides in the anchor sequence seems to effect amplification efficiency as a better sensitivity is obtained using the anchor primers HIV 22 LNA 3 and 4 (table 1) compared to the primers HIV22 LNA1 and 2 (table 1).

Example 6

Amplification of HIV RNA with Anchor Primers Using PNA (Peptide Nucleic Acid) in Anchor Sequence In order to increase the binding stability of the anchor, PNA nucleotides are incorporated in the anchor. Primers with anchor lengths of 14 nt (HIV17 PNA, table 1), 12 nt (HIV20 PNA, table 1), 9 nt (HIV21 PNA, table 1) and 7 nt (HIV22 PNA, table 1) were used in amplification in combination with a standard p2 primer (HIV2, table 1). All the anchors contain complete PNA sequences. Amplification was performed as described in example 1. Although a 10-fold decrease in sensitivity was observed as compared to DNA anchor primers, also the PNA-anchored primers were shown to be functional in NASBA (FIG. 10).

Example 7

Amplification of HIV RNA with Anchor p2 (Reverse) Primers

Amplification with anchor p2 primers (HIV27 and HIV29, table 1) was performed in combination with a standard p1 primer (HIV11, table 1). Standard p2 primers (HIV2 and HIV26, table 1) were used as a reference in combination with standard p1 primer (HIV11, table 1). Amplification was performed as described in example 1. For both amplifications, kinetics and amplification sensitivity was observed to be comparable to the reference amplification (FIG. 11).

Example 8

Amplification of HIV RNA with Anchor p2 Primers with Different Anchor Lengths

Amplification with anchor p2 primers with different anchor lengths varying from 22 to 14 nucleotides (HIV27, 31, 32, 33 and 29, table 1) was performed in combination with the standard p1 primer (HIV11, table 1). Amplification was performed as described in example 1. Shorten the anchor sequence of the p2-primers to 14 nucleotides results in comparable amplification efficiency as compared to the reference (HIV27 anchor primer, table 1) (FIG. 12).

Example 9

Amplification of HIV RNA with Anchor p1 Primer and Anchor p2 Primer

Amplification with anchor p1 primer (HIV17, table 1) and anchor p2 primers (HIV27 and HIV29, table 1) resulted in comparable amplification efficiency compared to the standard primer set (HIV1/ HIV2, table 1) (FIG. 13). Amplification was performed as described in example 1.

Example 10

Amplification of HCV RNA with Anchor p1 Primer

Also for the amplification of HCV RNA a NASBA was designed making use of an anchor p1 primer. Amplification with anchor p1 primer (HCV13 or HCV 49, table 2) and a normal p2 primer (HCV2, table 2) was performed. The anchor primers consist of a 14 nt anchor sequence upstream of the T7-promoter sequence and 7 nt hybridizing sequence downstream of the T7-promoter sequence. Amplification with standard p1 primer (HCV1, table 2) and standard p2 primer (HCV2, table 2) was used as reference. Molecular beacon HCV-WT3 (table 2) is used as probe and in vitro obtained HCV RNA transcript as input. Amplification was performed as described in example 1 except that the denaturing step at 65° C. was performed for 5 minutes instead of 2 minutes. Although differences in sensitivity and kinetics are observed, the results show that anchored primers can be used for amplification of HCV RNA (FIG. 14).

Example 11

Amplification of HCV RNA with Anchor p1 Primer, Having a 3 nt Gap Between the Binding Site of the Anchor and the 3' Hybridizing Sequence Amplification with anchor p1 primer (HCV22, table 2) and a normal p2 primer (HCV2, table 2) was performed. In this anchor, a 3 nt gap separates the binding site of the anchor sequence from that of the 7 nt 3' hybridizing sequence. Amplification with anchor p1 primer HCV13 (table 2) and standard p2 primer (HCV2, table 2) was used as reference. Molecular beacon HCV-WT3 (table 2) is used as probe and in vitro obtained HCV RNA transcript as input. Amplification was performed as described in Example 10. The results show that a 3 nt gap can exist between the binding site of the anchor and that of the 3' hybridizing sequence (FIG. 15), and that these anchored primers can be used to bridge non-conserved nucleotides in the primer-binding site.

TABLE 1

| NR° | Sequence 5'-> 3' | SEQ ID NO: |
|---|---|---|
| | Standard primers | |
| HIV1 (p1) | AATTCTAATACGACTCACTATAGGG TGCTATGTCACTTCCCCTTGGTTCTCTCA | 1 |
| HIV2 (p2) | AGTGGGGGGACATCAAGCAGCCATGCAAA | 2 |
| HIV26 (p2) | AGTGGGGGGACATCAAGCAGC | 3 |
| HIV11 | AATTCTAATACGACTCACTATAGGG AAACGGGCACGAGC TCTCTCA | 4 |
| | Anchor p1 primers | |
| HIV12 | TGCTATGTCACTTCCCCTTGGT AATTCTAATACGACTCACTATAGGG AAACGGGCACGAGC TCTCTCA | 5 |
| HIV15 | CTATGTCACTTCCCCTTGGT AATTCTAATACGACTCACTATAGGG AAACGGGCACGAGC TCTCTCA | 6 |
| HIV16 | TGTCACTTCCCCTTGGT AATTCTAATACGACTCACTATAGGG AAACGGGCACGAGC TCTCTCA | 7 |
| HIV17 | CACTTCCCCTTGGT AATTCTAATACGACTCACTATAGGG AAACGGGCACGAGC TCTCTCA | 8 |
| HIV20 | CTTCCCCTTGGT AATTCTAATACGACTCACTATAGGG AAACGGGCACGAGC TCTCTCA | 9 |
| HIV21 | CCCCTTGGT AATTCTAATACGACTCACTATAGGG AAACGGGCACGAGC TCTCTCA | 10 |
| HIV22 | CCTTGGT AATTCTAATACGACTCACTATAGGG AAACGGGCACGAGC TCTCTCA | 11 |
| | Anchor p1 primers with 2'-O-Methyl nucleotides in anchor | |
| HIV17 MET | CACTTCCCCTTGGT AATTCTAATACGACTCACTATAGGG AAACGGGCACGAGC TCTCTCA | 12 |
| HIV20 METa | CTTCCCCTTGGT AATTCTAATACGACTCACTATAGGG AAACGGGCACGAGC TCTCTCA | 13 |
| HIV20 METb | CTTCCCCTTGGT AATTCTAATACGACTCACTATAGGG AAACGGGCACGAGC TCTCTCA | 14 |
| HIV21 METa | CCCCTTGGT AATTCTAATACGACTCACTATAGGG AAACGGGCACGAGC TCTCTCA | 15 |
| HIV21 METb | CCCCTTGGT AATTCTAATACGACTCACTATAGGG AAACGGGCACGAGC TCTCTCA | 16 |
| HIV22 METa | CCTTGGT AATTCTAATACGACTCACTATAGGG AAACGGGCACGAGC TCTCTCA | 17 |
| HIV22 METb | CCTTGGT AATTCTAATACGACTCACTATAGGG AAACGGGCACGAGC TCTCTCA | 18 |
| | Anchor p1 primers with LNA nucleotides in anchor | |
| HIV22 LNA1 | CCTTGGT AATTCTAATACGACTCACTATAGGG AAACGGGCACGAGC TCTCTCA | 19 |
| HIV22 LNA2 | CCTTGGT AATTCTAATACGACTCACTATAGGG AAACGGGCACGAGC TCTCTCA | 20 |
| HIV22 LNA3 | CCTTGGT AATTCTAATACGACTCACTATAGGG AAACGGGCACGAGC TCTCTCA | 21 |
| HIV22 LNA4 | CCTTGGT AATTCTAATACGACTCACTATAGGG AAACGGGCACGAGC TCTCTCA | 22 |
| | Anchor p1 primers with PNA anchor | |
| HIV17 PNA | CACTTCCCCTTGGT AATTCTAATACGACTCACTATAGGG AAACGGGCACGAGC TCTCTCA | 23 |
| HIV20 PNA | CTTCCCCTTGGT AATTCTAATACGACTCACTATAGGG AAACGGGCACGAGC TCTCTCA | 24 |
| HIV21 PNA | CCCCTTGGT AATTCTAATACGACTCACTATAGGG AAACGGGCACGAGC TCTCTCA | 15 |
| HIV22 PNA | CCTTGGT AATTCTAATACGACTCACTATAGGG AAACGGGCACGAGC TCTCTCA | 16 |
| | Anchor p2 primers | |
| HIV27 | AGTGGGGGGACATCAAGCAGCC GACTTCAGGACTTCAGG ATGCAAA | 27 |
| HIV31 | GGGGGACATCAAGCAGCC GACTTCAGGACTTCAGG ATGCAAA | 28 |
| HIV32 | GGGACATCAAGCAGCC GACTTCAGGACTTCAGG ATGCAAA | 29 |
| HIV33 | GACATCAAGCAGCC GACTTCAGGACTTCAGG ATGCAAA | 30 |
| HIV29 | AGTGGGGGGACATC GACTTCAGGACTTCAGG AAGCAGC | 31 |
| | Molecular beacon for real time detection | |
| HIV MB WT | gcatgc ATCAATGAGGAIGCTGCAGAITGGGA gcatgc (5' FAM/3' dabcyl labeled) | 32 |

Target specific sequence in bold, T7 promoter sequence in italic, Y sequence (p1 primers) or X sequence (p2 primers) in italic and underlined, modified nucleotides in anchor with grey background

TABLE 2

| NR° | Sequence 5' -> 3' |
|---|---|
| | Standard primers |
| HCV1 (p1) | AATTCTAATACGACTCACTATAGGG CAAGCACCCTATCAGGCAGTA |
| HCV2 (p2) | GTCTAGCCATGGCGTTAGTA |
| | Anchor p1 primers |
| HCV13 | CAAGCACCCTATCA AATTCTAATACGACTCACTATAGGG AAGAGGGCACGAGC GGCAGTA |
| HCV22 | TCGCAAGCACCCTA AATTCTAATACGACTCACTATAGGG AAGAGGGCACGAGC GGCAGTA |
| HCV49 | CAAGCACCCTATCA AATTCTAATACGACTCACTATAGGG AAACGAGCACGAGC GGCAGTA |
| | Molecular beacon for real time detection |
| HCV WT3 | gctagc ATTTGGGCGTGCCCCCGCIAGA gctagc (5' FAM/3' dabcyl labeled) |

Target specific sequence in bold, T7 promoter sequence in italic, Y sequence (p1 primers) or X sequence (p2 primers) in italic and underlined

The invention claimed is:

1. A method for amplification of a target RNA sequence comprising the following steps:
   (a) annealing a first primer to the target RNA sequence, said first primer comprising:
   a first hybridizing sequence, comprising 7-14 nucleotides, which is complementary to at least a first segment of the target RNA sequence;
   a transcription enhancing sequence that comprises a promoter sequence that is operatively associated with the first hybridizing sequence; and
   a first oligonucleotide anchor that binds to a second segment of the target RNA sequence,
   wherein the transcription enhancing sequence forms a loop between the first oligonucleotide anchor and the first hybridizing sequence upon annealing of said first primer to the target RNA sequence;
   (b) extending said first primer in a reaction catalyzed by a DNA polymerase, forming a first RNA/cDNA hybrid nucleic acid molecule;
   (c) removing the target RNA sequence of the first RNA/cDNA hybrid nucleic acid molecule to obtain a first single stranded cDNA sequence;
   (d) annealing a second primer to the first single stranded cDNA sequence, said second primer comprising an amplification enhancing sequence having no promoter sequence and a second hybridizing sequence which is complementary to a first segment of the first single stranded cDNA sequence;
   (e) extending said second primer in a reaction catalyzed by a DNA polymerase to form a first double stranded DNA molecule; and
   (f) amplifying the first double stranded DNA molecule of step (e) using a DNA-dependent RNA polymerase with specificity for said promoter sequence of said first primer to produce a plurality of RNA transcripts that are complementary to the target RNA sequence.

2. The method according to claim 1, further comprising the steps of:
   (g) annealing said second primer to the RNA transcripts produced in step (f);
   (h) extending said second primer in a reaction catalyzed by the DNA polymerase to form a second RNA/cDNA hybrid nucleic acid molecule;
   (i) removing the RNA of the second RNA/cDNA hybrid molecule to obtain a second single stranded cDNA molecule;
   (j) annealing said first primer to the second single stranded cDNA sequence;
   (k) extending the 3' end of the second single stranded cDNA molecule in a reaction catalyzed by the DNA polymerase using said first primer as a template to form a second partly double stranded DNA molecule comprising a double stranded promoter site; and
   (l) amplifying the second double stranded DNA molecule of step (k) using said DNA-dependent RNA polymerase with specificity for the promoter sequence of the first primer to produce a plurality of RNA transcripts complementary to the target RNA sequence.

3. The method of claim 1, wherein said first primer comprises, from the 5' end to the 3' end, a first oligonucleotide anchor, a transcription enhancing sequence comprising said promoter, and a first hybridizing sequence of 7 to 14 nucleotides which are complementary to a first segment of the target RNA sequence of 7 to 14 contiguous nucleotides.

4. The method of claim 1, wherein said second primer comprises, from the 5' end to the 3' end, a second oligonucleotide anchor, an amplification enhancing sequence comprising no promoter, and a second hybridizing sequence of 7 to 14 nucleotides which are complementary to a first segment of the first single stranded cDNA sequence of 7 to 14 contiguous nucleotides.

5. The method of claim 1, wherein the first hybridizing sequence of said first primer comprises 7 to 10 nucleotides which are complementary to a first segment of the target RNA sequence of 7 to 10 contiguous nucleotides.

6. The method of claim 1, wherein the first oligonucleotide anchor of said first primer comprises 7 to 22 nucleotides which bind to a second segment of the target RNA sequence.

7. The method of claim 6, wherein the first oligonucleotide anchor comprises 7 to 14 nucleotides.

8. The method of claim 1, wherein the first oligonucleotide anchor comprises DNA, RNA or modified nucleotides.

9. The method of claim 1, wherein the first oligonucleotide anchor comprises PNA.

10. The method of claim 1, wherein said second oligonucleotide anchor of said second primer comprises 7 to 22 nucleotides which bind to a second segment of the first single stranded cDNA molecule.

11. The method of claim 10, wherein the second oligonucleotide anchor comprises 7 to 14 nucleotides.

12. The method of claim 1, wherein the number of nucleotides separating the second segment from the first segment is selected from the group consisting of: 0 to 6 nucleotides, 0 to 4 nucleotides, and 0 to 3 nucleotides.

13. The method of claim 1, wherein the transcription enhancing sequence comprises the nucleotide sequence of SEQ ID NO:39.

14. The method of claim 1, wherein the amplification enhancing sequence comprises the nucleotide sequence of SEQ ID NO:40.

15. The method of claim 1, wherein the promoter sequence is the bacteriophage T7 promoter sequence.

16. The method of claim 1, wherein the DNA polymerase is the avian myeloblastosis virus (AMV) reverse transcriptase.

17. The method of claim 1, wherein the target RNA sequence is a segment of the human immunodeficiency virus (HIV).

18. The method of claim 1, wherein the target nucleic acid is a segment of the human hepatitis C virus.

19. The method of claim 1, wherein the RNA transcripts are detected by one or more sequence-specific probes.

20. The method of claim 19, wherein the sequence-specific probe hybridizes to a sequence identical to the amplification sequence of said second primer.

21. The method of claim 8, wherein the modified nucleotides comprise 2'O-methyl modified nucleotides and/or LNA.

22. The method of claim 11, wherein the second oligonucleotide anchor comprises DNA, RNA or modified nucleotides.

23. The method of claim 22, wherein the modified nucleotides comprise 2'O-methyl modified nucleotides and/or LNA.

24. The method of claim 1, wherein the second oligonucleotide anchor comprises PNA.

25. The method of claim 1, wherein the second hybridizing sequence of said second primer comprises 7 to 10 nucleotides which are complementary to a first segment of the first single stranded cDNA sequence of 7 to 10 contiguous nucleotides.

26. The method of claim 1, wherein the second primer further comprises:
- a second oligonucleotide anchor that binds to a second segment of the first single stranded cDNA; and
- said second hybridizing sequence comprising 7-14 nucleotides which are complementary to a first segment of the first single stranded cDNA sequence,
- further wherein the amplification enhancing sequence forms a loop between the second oligonucleotide anchor and the second hybridizing sequence upon annealing of said second primer to the first single stranded cDNA sequence.

27. The method of claim 6, wherein the first oligonucleotide anchor comprises 9-14 nucleotides.

28. The method of claim 10, wherein the second oligonucleotide anchor comprises 9-14 nucleotides.

* * * * *

UNITED STATES PATENT AND TRADEMARK OFFICE
CERTIFICATE OF CORRECTION

| | |
|---|---|
| PATENT NO. | : 7,794,986 B2 |
| APPLICATION NO. | : 10/578552 |
| DATED | : September 14, 2010 |
| INVENTOR(S) | : Deiman et al. |

Page 1 of 1

It is certified that error appears in the above-identified patent and that said Letters Patent is hereby corrected as shown below:

Column 1, Line 3: Please correct by adding the following paragraph:
-- This application is a 35 U.S.C. §371 national phase application of international application serial number PCT/EP2004/012190, filed October 27, 2004, and published on May 26, 2005 as PCT Publication No. WO2005/047535, which claims priority to European Patent Application Serial No. 03078568.7, filed November 14, 2003, the entire contents of each of which are incorporated by reference herein. --

Column 11, Table 2: Please replace Table 2 with the following Table that includes an additional column providing sequence listing identifiers for the nucleotide sequences therein.

| NR° | Sequence 5' -> 3' | SEQ ID NO |
|---|---|---|
| | *Standard primers* | |
| HCV1 (p1) | AATTCTAATACGACTCACTATAGGG CAAGCACCCTATCAGGCAGTA | 33 |
| HCV2 (p2) | GTCTAGCCATGGCGTTAGTA | 34 |
| | *Anchor p1 primers* | |
| HCV13 | CAAGCACCCTATCA AATTCTAATACGACTCACTATAGGG AAGAGGGCACGAGC GGCAGTA | 35 |
| HCV22 | TCGCAAGCACCCTA AATTCTAATACGACTCACTATAGGG AAGAGGGCACGAGC GGCAGTA | 36 |
| HCV49 | CAAGCACCCTATCA AATTCTAATACGACTCACTATAGGG AAACGAGCACGAGC GGCAGTA | 37 |
| | *Molecular beacon for real time detection* | |
| HCV WT3 | gctagc ATTTGGGCGTGCCCCCGCIAGA gctagc (5' FAM/3' dabcyl labeled) | 38 |

Signed and Sealed this
Seventeenth Day of July, 2012

David J. Kappos
*Director of the United States Patent and Trademark Office*